United States Patent
Chen et al.

(10) Patent No.: US 10,611,748 B2
(45) Date of Patent: Apr. 7, 2020

(54) XANTHONE DERIVATIVES FOR THE TREATMENT OF HEPATITIS B VIRUS DISEASE

(71) Applicant: Hoffmann-La Roche Inc., Little Falls, NJ (US)

(72) Inventors: Dongdong Chen, Shanghai (CN); Wenming Chen, Shanghai (CN); Song Feng, Shanghai (CN); Lu Gao, Shanghai (CN); Hong Shen, Shanghai (CN); Xuefei Tan, Shanghai (CN); Li Wang, Shanghai (CN)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 16/199,534

(22) Filed: Nov. 26, 2018

(65) Prior Publication Data

US 2019/0185444 A1 Jun. 20, 2019

Related U.S. Application Data

(63) Continuation of application No. PCT/EP2017/062320, filed on May 23, 2017.

(51) Int. Cl.

| C07D 311/86 | (2006.01) |
|---|---|
| C07D 493/10 | (2006.01) |
| C07D 409/04 | (2006.01) |
| C07D 405/14 | (2006.01) |
| C07D 491/052 | (2006.01) |
| C07D 311/82 | (2006.01) |
| C07D 405/04 | (2006.01) |
| C07D 487/10 | (2006.01) |
| C07D 407/04 | (2006.01) |
| A61P 31/20 | (2006.01) |
| C07D 493/04 | (2006.01) |
| C07D 495/04 | (2006.01) |

(52) U.S. Cl.
CPC ............ *C07D 311/86* (2013.01); *A61P 31/20* (2018.01); *C07D 311/82* (2013.01); *C07D 405/04* (2013.01); *C07D 405/14* (2013.01); *C07D 407/04* (2013.01); *C07D 409/04* (2013.01); *C07D 487/10* (2013.01); *C07D 491/052* (2013.01); *C07D 493/04* (2013.01); *C07D 493/10* (2013.01); *C07D 495/04* (2013.01)

(58) Field of Classification Search
CPC ...... A61P 31/20; C07D 311/82; C07D 311/86; C07D 405/04; C07D 405/14; C07D 407/04; C07D 409/04; C07D 487/10; C07D 491/052; C07D 493/04; C07D 493/10; C07D 495/04
See application file for complete search history.

(56) References Cited

U.S. PATENT DOCUMENTS

| 2005/0171079 A1 | 8/2005 | Schrimpf et al. |
| 2012/0184578 A1 | 7/2012 | Teow et al. |

FOREIGN PATENT DOCUMENTS

| CN | 104370871 B | * | 2/2013 |
| WO | 2004/085418 A2 | | 10/2004 |
| WO | 2013/184755 A2 | | 12/2013 |
| WO | 2015/030057 A1 | | 3/2015 |

OTHER PUBLICATIONS

"International Preliminary Report on Patentability—PCT/EP2017/062320":1-6 (dated Nov. 27, 2018).
"International Search Report—PCT/EP2017/062320":1-15 (dated Jul. 17, 2017).
Zhang, Fan et al., "A review of non-nucleoside anti-hepatitis B virus agents" European Journal of Medicinal Chemistry 75(30):267-281 (Dec. 30, 2014).

* cited by examiner

*Primary Examiner* — Deepak R Rao
(74) *Attorney, Agent, or Firm* — Genentech, Inc.; Richard G.A. Bone

(57) ABSTRACT

The present invention provides novel compounds having the general formula:

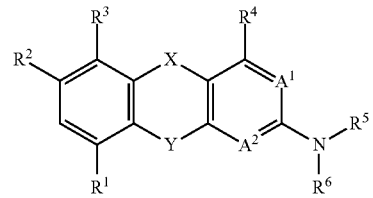

Figure 1:
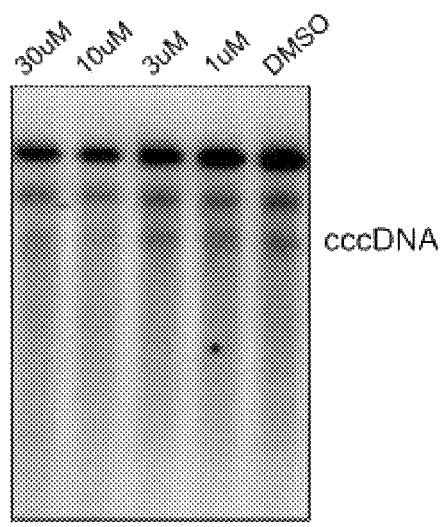

wherein $R^1$ to $R^6$, X, Y, $A^1$ and $A^2$ are as described herein, compositions including the compounds and methods of using the compounds.

31 Claims, 3 Drawing Sheets
Specification includes a Sequence Listing.

Example 2

Example 3

Example 4 cccDNA

Example 5 cccDNA

Example 7 cccDNA

Example 26 cccDNA

SEQUENCE LISTING

```
<160> NUMBER OF SEQ ID NOS: 4

<210> SEQ ID NO 1
<211> LENGTH: 863
<212> TYPE: DNA
<213> ORGANISM: Hepatitis B virus

<400> SEQUENCE: 1
tcctctgccg atccatactg cggaactcct agccgcttgt tttgctcgca gcaggtctgg     60
agcaaacatt atcgggactg ataactctgt tgtcctatcc cgcaaatata catcgtttcc    120
atggctgcta ggctgtgctg ccaactggat cctgcgcggg acgtcctttg tttacgtccc    180
gtcggcgctg aatcctgcgg acgacccttc tcggggtcgc ttgggactct ctcgtcccct    240
tctccgtctg ccgttccgac cgaccacggg gcgcacctct ctttacgcgg actccccgtc    300
tgtgccttct catctgccgg accgtgtgca cttcgcttca cctctgcacg tcgcatggag    360
accaccgtga acgcccacca aatattgccc aaggtcttac ataagaggac tcttggactc    420
tcagcaatgt caacgaccga ccttgaggca tacttcaaag actgtttgtt taaagactgg    480
gaggagttgg gggaggagat taggttaaag gtctttgtac taggaggctg taggcataaa    540
ttggtctgcg caccagcacc atgcaacttt ttcacctctg cctaatcatc tcttgttcat    600
gtcctactgt tcaagcctcc aagctgtgcc ttgggtggct ttggggcatg gacatcgacc    660
cttataaaga atttggagct actgtggagt tactctcgtt tttgccttct gacttctttc    720
cttcagtacg agatcttcta gataccgcct cagctctgta tcgggaagcc ttagagtctc    780
ctgagcattg ttcacctcac catactgcac tcaggcaagc aattctttgc tggggggaac    840
taatgactct agctacctgg gtg                                            863

<210> SEQ ID NO 2
<211> LENGTH: 20
<212> TYPE: DNA
<213> ORGANISM: Hepatitis B virus

<400> SEQUENCE: 2
aagaaaaacc ccgcctgtaa                                                 20

<210> SEQ ID NO 3
<211> LENGTH: 23
<212> TYPE: DNA
<213> ORGANISM: Hepatitis B virus

<400> SEQUENCE: 3
cctgttctga ctactgcctc tcc                                             23

<210> SEQ ID NO 4
<211> LENGTH: 27
<212> TYPE: DNA
<213> ORGANISM: Hepatitis B virus

<400> SEQUENCE: 4
cctgatgtga tgttctccat gttcagc                                         27
```

XANTHONE DERIVATIVES FOR THE TREATMENT OF HEPATITIS B VIRUS DISEASE

RELATED APPLICATIONS

This application is a continuation of International Application No. PCT/EP2017/062320, filed May 23, 2017, which claims priority to Application No. PCT/CN2017/080914 filed, Apr. 18, 2017 and Application No. PCT/CN2016/083472, filed May 26, 2016 each of which are incorporated herein by reference in its entirety.

SEQUENCE LISTING

This application contains a Sequence Listing which has been submitted via EFS-Web and is hereby incorporated by reference in its entirety. Said ASCII copy, created on Oct. 30, 2018, is named Sequence_Listing.txt and is 2,056 bytes in size.

The present invention relates to organic compounds useful for therapy and/or prophylaxis in a mammal, and in particular to cccDNA (covalently closed circular DNA) inhibitors useful for treating HBV infection.

FIELD OF THE INVENTION

The present invention relates to novel xanthone derivatives having pharmaceutical activity, their manufacture, pharmaceutical compositions containing them and their potential use as medicaments.

The present invention relates to compounds of formula I

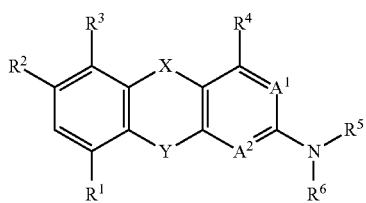

wherein $R^1$ to $R^6$, X, Y, $A^1$ and $A^2$ are as described below, or to pharmaceutically acceptable salts, or enantiomers, or diastereomers thereof.

Hepatitis B virus (HBV) infection is one of the most prevalent viral infections and is a leading cause of chronic liver disease and liver transplants worldwide. It is estimated that worldwide, 2 billion people have evidence of past or present infection with HBV. Over 250 million individualsare currently chronically infected with HBV and are therefore at high risk to develop liver fibrosis, cirrhosis and hepatocellular carcinoma (HCC). There are data to indicate ~800,000 deaths per year are directly linked to HBV infection (Lozano, R. et al., *Lancet* (2012), 380 (9859), 2095-2128; Goldstein, S. T. et al., *Int J Epidemiol* (2005), 34 (6), 1329-1339).

Many countries in the world administer hepatitis B vaccine starting at birth or in early childhood, which has greatly reduced the incidence and prevalence of hepatitis B in most endemic regions over the past few decades. However the vaccine has no impact on people who were infected before the widely use of the vaccine in developing end-stage liver disease or HCC (Chen, D. S., *J Hepatol* (2009), 50 (4), 805-816). Vaccination at birth of infants born to HBV positive mothers is usually not sufficient for protecting vertical transmission and combination with hepatitis B immune globulin is needed (Li, X. M. et al., *World J Gastroenterol* (2003), 9 (7), 1501-1503).

Currently FDA-approved treatments for chronic hepatitis B include two type 1 interferons (IFN) which are IFNalfa-2b and pegylated IFN alfa-2a and five nucleos(t)ide analogues (NAs) which are lamivudine (3TC), tenofovir disoproxil fumarate (TDF), adefovir (ADV), telbivudine (LdT), and entecavir (ETV). IFN treatment is finite, but it is known to have severe side effects, and only a small percentage of patients showed a sustained virological response, measured as loss of hepatitis B surface antigen (HBsAg). NAs are inhibitors of the HBV reverse transcriptase, profoundly reduce the viral load in vast majority of treated patients, and lead to significant improvement of liver function and reduced incidence of liver failure and hepatocellular carcinoma. However, NAs are associated with clinical issues including increasing drug resistance, infinite treatment duration and viral rebound (Ahmed, M. et al., *Drug Discov Today* (2015), 20 (5), 548-561; Zoulim, F. and Locamini, S., *Gastroenterology* (2009), 137 (5), 1593-1608 e1591-1592).

HBV chronic infection is caused by persistence of covalently closed circular (ccc)DNA, which exists as an episomal form in hepatocyte nuclei. cccDNA serves as the template for viral RNA transcription and subsequent viral DNA generation. Only a few copies of cccDNA per liver cell can establish or re-initiate viral replication. Therefore, a cure of chronic hepatitis B will require elimination of cccDNA or permanently silencing of cccDNA. However, cccDNA is intrinsically very stable and currently available therapeutics could not eliminate cccDNA or permanently silence cccDNA (Nassal, M., *Gut* (2015), 64 (12), 1972-1984; Gish, R. G. et al., *Antiviral Res* (2015), 121, 47-58; Levrero, M. et al., *J Hepatol* (2009), 51 (3), 581-592.). While NAs may protect the remaining uninfected hepatocytes, they could not eliminate the cccDNA which are already present in the infected cells. There is an urgent need to discover and develop new anti-HBV reagents to eliminate or permanently silence cccDNA, the source of chronicity (Ahmed, M. et al., *Drug Discov Today* (2015), 20 (5), 548-561; Nassal, M., *Gut* (2015), 64 (12), 1972-1984).

SUMMARY OF THE INVENTION

Objects of the present invention are novel compounds of formula I, their manufacture, medicaments based on a compound in accordance with the invention and their production as well as the use of compounds of formula I as cccDNA inhibitors and for the treatment or prophylaxis of HBV infection. The compounds of formula I show superior anti-HBV activity. In addition, the compounds of formula I also show good PK profiles.

The present invention relates to a compound of formula I

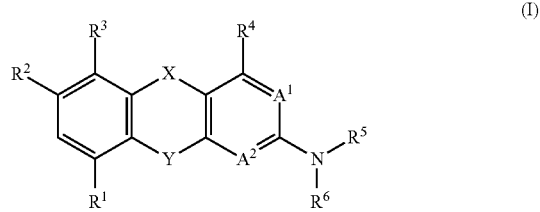

wherein, $R^1$ is halogen or haloC$_{1-6}$alkyl;

$R^2$ is hydrogen or halogen;

$R^3$ is hydrogen, halogen, C$_{1-6}$alkyl, haloC$_{1-6}$alkyl, cyano or hydroxy;

$R^4$ is hydrogen;

$R^5$ and $R^6$ together with nitrogen to which they are attached form pyrrolidinyl, oxopyrrolidinyl, azepanyl, diazepanyl, piperidinyl, hydroxypiperidinyl, carboxypiperidinyl, C$_{1-6}$alkylpiperazinyl, morpholinyl, 2,6-diazaspiro[3.4]octan-6-yl or 2,7-diazaspiro[4.4]nonan-2-yl, wherein pyrrolidinyl is unsubstituted or substituted with one, two or three substituents independently selected from C$_{1-6}$alkyl, C$_{1-6}$alkoxy, hydroxy, carboxy, haloC$_{1-6}$alkyl, carboxyC$_{1-6}$alkyl, hydroxyC$_{1-6}$alky, amino, C$_{1-6}$alkoxycarbonyl, halophenyl, pyridinyl, (diC$_{1-6}$alkylamino)carbonyl and morpholinylcarbonyl;

X is —C(=O)— or —C($R^9$)($R^{10}$)—, wherein $R^9$ and $R^{10}$ are independently selected from hydrogen, C$_{1-6}$alkyl, haloC$_{1-6}$alkyl, C$_{1-6}$alkoxy, hydroxy, oxetanyl and halophenylCH(—O-carbonylC$_{1-6}$alkyl)-; or $R^9$ and $R^{10}$ together with carbon to which they are attached form

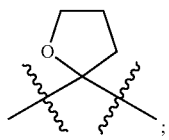 [SMILES: *C1(*)CCCO1 ; ";"]

$A^1$ is N or CR$^7$, wherein R$^7$ is hydrogen, halogen or C$_{1-6}$alkyl;

$A^2$ is N or CR$^8$, wherein R$^8$ is hydrogen or halogen;

Y is O or S;

with the provision that 1-[5-fluoro-9-(oxetan-3-yl)-9H-xanthen-3-yl]pyrrolidine is excluded; or pharmaceutically acceptable salts, or enantiomers, or diastereomers thereof.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

As used herein, the term "C$_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "C$_{1-6}$alkyl" groups are methyl, ethyl, isopropyl and tert-butyl. More particularly, "C$_{1-6}$alkyl" group is methyl.

The term "C$_{1-6}$alkoxy" alone or in combination signifies a group C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy. More particularly, "C$_{1-6}$alkoxy" group is methoxy.

The term "halogen" means fluorine, chlorine, bromine or iodine.

The term "haloC$_{1-6}$alkyl" denotes a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "haloC$_{1-6}$alkyl" group is difluoromethyl or trifluoromethyl.

The term "amino" denotes a group of the formula —NR'R" wherein R' and R" are independently hydrogen, C$_{1-6}$alkyl, C$_{1-6}$alkoxy, C$_{3-7}$cycloalkyl, heteroC$_{3-7}$cycloalkyl, aryl or heteroaryl. Alternatively, R' and R", together with the nitrogen to which they are attached, can form a heteroC$_{3-7}$cycloalkyl.

The term "carbonyl" alone or in combination refers to the group —C(O)—.

The term "cyano" alone or in combination refers to the group —CN.

The term "halophenyl" denotes a phenyl substituted once, twice or three times by halogen. Examples of halophenyl include, but not limited to, bromophenyl, chlorophenyl, difluorophenyl, fluorophenyl and fluorochlorophenyl. Particular "halophenyl" group is fluorophenyl or chlorophenyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & *Development* 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

As used herein, "PHH", an abbreviation for primary human hepatocytes, is the host cell infected by HBV in vivo, and commonly considered to be the ideal cellular model for HBV infection.

As used herein, "cryopreservation" is a process where organelles, cells, tissues, extracellular matrix, organs or any other biological constructs are preserved by cooling to very low temperatures (Pegg, David E. (2007 Jan. 1). "Principles of cryopreservation". Methods in Molecular Biology (Clifton, N.J.) 368: 39-57.) (typically −80° C. using solid carbon dioxide or −196° C. using liquid nitrogen).

As used herein, "cryopreserved PHH" means the primary human hepatocytes that are preserved by cryopreservation. Cryopreserved PHH is commercially available, e.g., from Life Technologies, Corning Gentest, IVAL (In Vitro ADMET Laboratories) or Bioreclamation IVT.

As used herein, a "PHH culture medium" is a medium that is used for maintaining viability and biological activity of PHH. The PHH culture medium usually comprises the essential medium, some essential factors, such as human epidermal growth factor, dexamethasone, human recombinant insulin that is needed for the growth of hepatocytes, and some antibiotics such as penicillin and streptomycin.

cccDNA Inhibitors

The present invention provides (i) a compound having the general formula I:

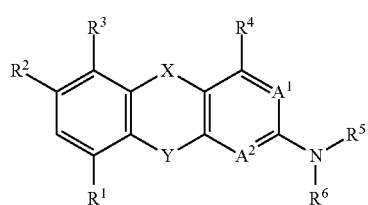

wherein, $R^1$ is halogen or haloC$_{1-6}$alkyl;

$R^2$ is hydrogen or halogen;

$R^3$ is hydrogen, halogen, C$_{1-6}$alkyl, haloC$_{1-6}$alkyl, cyano or hydroxy;

$R^4$ is hydrogen;

$R^5$ and $R^6$ together with nitrogen to which they are attached form pyrrolidinyl, oxopyrrolidinyl, azepanyl, diazepanyl, piperidinyl, hydroxypiperidinyl, carboxypiperidinyl, C$_{1-6}$alkylpiperazinyl, morpholinyl, 2,6-diazaspiro[3.4]octan-6-yl or 2,7-diazaspiro[4.4]nonan-2-yl, wherein pyrrolidinyl is unsubstituted or substituted with one, two or three substituents independently selected from C$_{1-6}$alkyl, C$_{1-6}$alkoxy, hydroxy, carboxy, haloC$_{1-6}$alkyl, carboxy C$_{1-6}$alkyl, hydroxyC$_{1-6}$alky, amino, C$_{1-6}$alkoxycarbonyl, halophenyl, pyridinyl, (diC$_{1-6}$alkylamino)carbonyl and morpholinylcarbonyl;

X is —C(═O)— or —C($R^9$)($R^{10}$)—, wherein $R^9$ and $R^{10}$ are independently selected from hydrogen, C$_{1-6}$alkyl, haloC$_{1-6}$alkyl, C$_{1-6}$alkoxy, hydroxy, oxetanyl and halophenylCH(—O-carbonylC$_{1-6}$alkyl)-; or

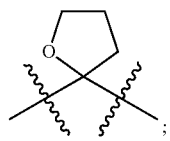

$R^9$ and $R^{10}$ together with carbon to which they are attached form $A^1$ is N or CR$^7$, wherein $R^7$ is hydrogen, halogen or C$_{1-6}$alkyl;

$A^2$ is N or CR$^8$, wherein $R^8$ is hydrogen or halogen;

Y is O or S;

with the provision that 1-[5-fluoro-9-(oxetan-3-yl)-9H-xanthen-3-yl]pyrrolidine is excluded; or pharmaceutically acceptable salts, or enantiomers, or diastereomers thereof.

A further embodiment of the present invention is (ii) a compound of formula I, wherein, $R^1$ is halogen or haloC$_{1-6}$alkyl;

$R^2$ is hydrogen or halogen;

$R^3$ is hydrogen, halogen, C$_{1-6}$alkyl, haloC$_{1-6}$alkyl, cyano or hydroxy;

$R^4$ is hydrogen;

$R^5$ and $R^6$ together with nitrogen to which they are attached form pyrrolidinyl, oxopyrrolidinyl, azepanyl, diazepanyl, piperidinyl, hydroxypiperidinyl, carboxypiperidinyl, C$_{1-6}$alkylpiperazinyl, morpholinyl, 2,6-diazaspiro[3.4]octan-6-yl or 2,7-diazaspiro[4.4]nonan-2-yl, wherein pyrrolidinyl is unsubstituted or substituted with one, two or three substituents independently selected from C$_{1-6}$alkyl, C$_{1-6}$alkoxy, hydroxy, carboxy, haloC$_{1-6}$alkyl, carboxy C$_{1-6}$alkyl, hydroxyC$_{1-6}$alky, amino, C$_{1-6}$alkoxycarbonyl, halophenyl, pyridinyl, (diC$_{1-6}$alkylamino)carbonyl and morpholinylcarbonyl;

X is —C(═O)—;

$A^1$ is N or CR$^7$, wherein $R^7$ is hydrogen, halogen or C$_{1-6}$alkyl;

$A^2$ is N or CH;

Y is O;

or pharmaceutically acceptable salts, or enantiomers, or diastereomers thereof.

Another embodiment of the present invention is (iii) a compound of formula I, wherein,
$R^1$ is halogen or haloC$_{1-6}$alkyl;
$R^2$ is hydrogen or halogen;
$R^3$ is hydrogen, halogen, C$_{1-6}$alkyl, haloC$_{1-6}$alkyl, cyano or hydroxy;
$R^4$ is hydrogen;
$R^5$ and $R^6$ together with nitrogen to which they are attached form pyrrolidinyl unsubstituted or substituted with one, two or three substituents independently selected from C$_{1-6}$alkyl, C$_{1-6}$alkoxy, hydroxy, carboxy, haloC$_{1-6}$alkyl, carboxyC$_{1-6}$alkyl, hydroxyC$_{1-6}$alky, amino, C$_{1-6}$alkoxycarbonyl, halophenyl, pyridinyl, (diC$_{1-6}$alkylamino)carbonyl and morpholinylcarbonyl;
X is —C(=O)—;
$A^1$ is N or CR$^7$, wherein $R^7$ is hydrogen, halogen or C$_{1-6}$alkyl;
$A^2$ is N or CH;
Y is O;
or pharmaceutically acceptable salts, or enantiomers, or diastereomers thereof.

Another embodiment of the present invention is (iv) a compound of formula I, wherein,
$R^1$ is halogen or haloC$_{1-6}$alkyl;
$R^2$ is hydrogen or halogen;
$R^3$ is hydrogen, halogen, C$_{1-6}$alkyl, haloC$_{1-6}$alkyl, cyano or hydroxy;
$R^4$ is hydrogen;
$R^5$ and $R^6$ together with nitrogen to which they are attached form pyrrolidinyl, hydroxypyrrolidinyl, C$_{1-6}$alkoxypyrrolidinyl, carboxypyrrolidinyl or C$_{1-6}$alkoxycarbonylpyrrolidinyl;
X is —C(=O)—;
$A^1$ is CR$^7$, wherein $R^7$ is hydrogen, halogen or C$_{1-6}$alkyl;
$A^2$ is CH;
Y is O;
or pharmaceutically acceptable salts, or enantiomers, or diastereomers thereof.

A further embodiment of the present invention is (v) a compound of formula I, wherein,
$R^1$ is fluoro, chloro, bromo or trifluoromethyl;
$R^2$ is hydrogen, fluoro or chloro;
$R^3$ is hydrogen, fluoro, chloro, methyl, trifluoromethyl, cyano or hydroxy;
$R^4$ is hydrogen;
$R^5$ and $R^6$ together with nitrogen to which they are attached form pyrrolidinyl, hydroxypyrrolidinyl, methoxyprrolidinyl, carboxypyrrolidinyl or methoxycarbonylpyrrolidinyl;
X is —C(=O)—;
$A^1$ is CR$^7$, wherein $R^7$ is hydrogen, fluoro, chloro or methyl;
$A^2$ is CH;
Y is O; or pharmaceutically acceptable salts, or enantiomers, or diastereomers thereof.

A further embodiment of the present invention is (vi) a compound of formula I, wherein,
$R^1$ is fluoro, chloro, bromo or trifluoromethyl;
$R^2$ is hydrogen or chloro;
$R^3$ is hydrogen, fluoro, chloro, methyl, trifluoromethyl, cyano or hydroxy;
$R^4$ is hydrogen;
$R^5$ and $R^6$ together with nitrogen to which they are attached form pyrrolidinyl, hydroxypyrrolidinyl, methoxyprrolidinyl, carboxypyrrolidinyl or methoxycarbonylpyrrolidinyl;
X is —C(=O)—;
$A^1$ is CR$^7$, wherein $R^7$ is hydrogen, fluoro, chloro or methyl;
$A^2$ is CH;
Y is O; or pharmaceutically acceptable salts, or enantiomers, or diastereomers thereof.

A further embodiment of the present invention is (vii) a compound of formula I, or pharmaceutically acceptable salts, or enantiomers, or diastereomers thereof, wherein $R^1$ is fluoro or chloro, and all remaining substituents have the significances given herein before.

Another further embodiment of the present invention is (viii) a compound of formula I, or pharmaceutically acceptable salts, or enantiomers, or diastereomers thereof, wherein $R^2$ is hydrogen, and all remaining substituents have the significances given herein before.

Another further embodiment of the present invention is (ix) a compound of formula I, or pharmaceutically acceptable salts, or enantiomers, or diastereomers thereof, wherein $R^3$ is hydrogen, fluoro, chloro or trifluoromethyl, and all remaining substituents have the significances given herein before.

Another further embodiment of the present invention is (x) a compound of formula I, or pharmaceutically acceptable salts, or enantiomers, or diastereomers thereof, wherein $R^5$ and $R^6$ together with nitrogen to which they are attached form pyrrolidinyl or carboxypyrrolidinyl, and all remaining substituents have the significances given herein before.

Another further embodiment of the present invention is (xi) a compound of formula I, or pharmaceutically acceptable salts, or enantiomers, or diastereomers thereof, wherein $A^1$ is CH, and all remaining substituents have the significances given herein before.

Another embodiment of the present invention is (xii) a compound of formula I, wherein,
$R^1$ is halogen;
$R^2$ is hydrogen;
$R^3$ is hydrogen, halogen or haloC$_{1-6}$alkyl;
$R^4$ is hydrogen;
$R^5$ and $R^6$ together with nitrogen to which they are attached form pyrrolidinyl or carboxypyrrolidinyl;
X is —C(=O)—;
$A^1$ is CH;
$A^2$ is CH;
Y is O;
or pharmaceutically acceptable salts, or enantiomers, or diastereomers thereof.

A further embodiment of the present invention is (xiii) a compound of formula I, wherein,
$R^1$ is fluoro or chloro;
$R^2$ is hydrogen;
$R^3$ is hydrogen, fluoro, chloro or trifluoromethyl;
$R^4$ is hydrogen;
$R^5$ and $R^6$ together with nitrogen to which they are attached form pyrrolidinyl or carboxypyrrolidinyl;
X is —C(=O)—;
$A^1$ is CH;
$A^2$ is CH;
Y is O;
or pharmaceutically acceptable salts, or enantiomers, or diastereomers thereof.

In another embodiment (xiv) of the present invention, particular compounds of the present invention are selected from
5-chloro-3-pyrrolidin-1-yl-xanthen-9-one;
1-(5-chloro-9-oxo-xanthen-3-yl)pyrrolidine-3-carboxylic acid;
(3R)-1-(5-chloro-9-oxo-xanthen-3-yl)pyrrolidine-3-carboxylic acid;

(3S)-1-(5-chloro-9-oxo-xanthen-3-yl)pyrrolidine-3-carboxylic acid;
1-(5-fluoro-9-oxo-xanthen-3-yl)pyrrolidine-3-carboxylic acid;
1-(5-bromo-9-oxo-xanthen-3-yl)pyrrolidine-3-carboxylic acid;
methyl 1-(5-chloro-9-oxo-xanthen-3-yl)pyrrolidine-3-carboxylate;
5-fluoro-3-pyrrolidin-1-yl-xanthen-9-one;
1-chloro-4-fluoro-6-pyrrolidin-1-yl-xanthen-9-one;
5-fluoro-3-(3-hydroxypyrrolidin-1-yl)xanthen-9-one;
5-fluoro-2-methyl-3-pyrrolidin-1-yl-xanthen-9-one;
1-(5,8-dichloro-9-oxo-xanthen-3-yl)pyrrolidine-3-carboxylic acid;
5-chloro-3-[(3S)-3-hydroxypyrrolidin-1-yl]xanthen-9-one;
2,5-difluoro-3-pyrrolidin-1-yl-xanthen-9-one;
5-chloro-3-[(3R)-3-hydroxypyrrolidin-1-yl]xanthen-9-one;
5-fluoro-3-[(3S)-3-hydroxypyrrolidin-1-yl]xanthen-9-one;
5-fluoro-3-[(3R)-3-hydroxypyrrolidin-1-yl]xanthen-9-one;
5-fluoro-3-(3-methoxypyrrolidin-1-yl)xanthen-9-one;
2-chloro-4-fluoro-6-pyrrolidin-1-yl-xanthen-9-one;
1-(5-chloro-9-oxo-xanthen-3-yl)pyrrolidine-2-carboxylic acid;
1-[9-oxo-5-(trifluoromethyl)xanthen-3-yl]pyrrolidine-3-carboxylic acid;
1-(5-chloro-2-methyl-9-oxo-xanthen-3-yl)pyrrolidine-3-carboxylic acid;
1-(5-chloro-8-methyl-9-oxo-xanthen-3-yl)pyrrolidine-3-carboxylic acid;
1-(5-chloro-2-fluoro-9-oxo-xanthen-3-yl)pyrrolidine-3-carboxylic acid;
1-(2,5-dichloro-9-oxo-xanthen-3-yl)pyrrolidine-3-carboxylic acid;
1-(5-chloro-8-cyano-9-oxo-xanthen-3-yl)pyrrolidine-3-carboxylic acid;
1-(5-chloro-8-hydroxy-9-oxo-xanthen-3-yl)pyrrolidine-3-carboxylic acid;
1-(5-chloro-8-fluoro-9-oxo-xanthen-3-yl)pyrrolidine-3-carboxylic acid;
1-[5-chloro-9-oxo-8-(trifluoromethyl)xanthen-3-yl]pyrrolidine-3-carboxylic acid;
2-chloro-5-fluoro-3-pyrrolidin-1-yl-xanthen-9-one;
(3R)-1-(5,8-dichloro-9-oxo-xanthen-3-yl)pyrrolidine-3-carboxylic acid;
1-(5,7-dichloro-9-oxo-xanthen-3-yl)pyrrolidine-3-carboxylic acid;
1-(5-chloro-7-fluoro-9-oxo-xanthen-3-yl)pyrrolidine-3-carboxylic acid; and
(3R)-1-(5-chloro-2-methyl-9-oxo-xanthen-3-yl)pyrrolidine-3-carboxylic acid;
or pharmaceutically acceptable salts, or enantiomers, or diastereomers thereof.

In a further embodiment (xv) of the present invention, particular compounds of the present invention are selected from
5-chloro-3-pyrrolidin-1-yl-xanthen-9-one;
1-(5-chloro-9-oxo-xanthen-3-yl)pyrrolidine-3-carboxylic acid;
(3R)-1-(5-chloro-9-oxo-xanthen-3-yl)pyrrolidine-3-carboxylic acid;
(3S)-1-(5-chloro-9-oxo-xanthen-3-yl)pyrrolidine-3-carboxylic acid;
5-fluoro-3-pyrrolidin-1-yl-xanthen-9-one;
1-(5-chloro-8-fluoro-9-oxo-xanthen-3-yl)pyrrolidine-3-carboxylic acid;
1-[5-chloro-9-oxo-8-(trifluoromethyl)xanthen-3-yl]pyrrolidine-3-carboxylic acid;
1-(5,8-dichloro-9-oxo-xanthen-3-yl)pyrrolidine-3-carboxylic acid; and
(3R)-1-(5,8-dichloro-9-oxo-xanthen-3-yl)pyrrolidine-3-carboxylic acid;
or pharmaceutically acceptable salts, or enantiomers, or diastereomers thereof.

Another embodiment of the present invention is (xvi) a compound of formula I, or pharmaceutically acceptable salts, or enantiomers, or diastereomers thereof, wherein $R^5$ and $R^6$ together with nitrogen to which they are attached form aminopyrrolidinyl, carboxy(methyl)pyrrolidinyl, carboxy(dimethyl)pyrrolidinyl, carboxy(trifluoromethyl)pyrrolidinyl, carboxy(fluorophenyl)pyrrolidinyl, carboxy(chlorophenyl)pyrrolidinyl, carboxy(pyridinyl)pyrrolidinyl, carboxymethylpyrrolidinyl, dimethylaminocarbonylprrolidinyl, hydroxymethylpyrrolidinyl, morpholinylcarbonylpyrrolidinyl or pyridinylpyrrolidinyl, and all remaining substituents have the significances given herein before.

In another embodiment (xvii) of the present invention, particular compounds of the present invention are selected from
2-[1-(5-chloro-9-oxo-xanthen-3-yl)pyrrolidin-3-yl]acetic acid;
5-chloro-3-[3-(hydroxymethyl)pyrrolidin-1-yl]xanthen-9-one;
(3R,4S)-1-(5-chloro-9-oxo-xanthen-3-yl)-4-(4-fluorophenyl)pyrrolidine-3-carboxylic acid;
1-(5-chloro-9-oxo-xanthen-3-yl)-3-methyl-pyrrolidine-3-carboxylic acid;
1-(5-chloro-9-oxo-xanthen-3-yl)-4,4-dimethyl-pyrrolidine-3-carboxylic acid;
(3R,4S)-1-(5-chloro-9-oxo-xanthen-3-yl)-4-(3-pyridyl)pyrrolidine-3-carboxylic acid;
1-(5-chloro-9-oxo-xanthen-3-yl)-3-(trifluoromethyl)pyrrolidine-3-carboxylic acid;
(3S,4R)-1-(5-chloro-9-oxo-xanthen-3-yl)-4-(4-chlorophenyl)pyrrolidine-3-carboxylic acid;
5-fluoro-3-[3-(4-pyridyl)pyrrolidin-1-yl]xanthen-9-one;
1-(5-chloro-9-oxo-xanthen-3-yl)-N,N-dimethyl-pyrrolidine-3-carboxamide;
3-[(3S)-3-aminopyrrolidin-1-yl]-5-fluoro-xanthen-9-one;
3-[(3R)-3-aminopyrrolidin-1-yl]-5-fluoro-xanthen-9-one; and
5-chloro-3-[3-(morpholine-4-carbonyl)pyrrolidin-1-yl]xanthen-9-one;
or pharmaceutically acceptable salts, or enantiomers, or diastereomers thereof.

Another embodiment of the present invention is (xviii) a compound of formula I, or pharmaceutically acceptable salts, or enantiomers, or diastereomers thereof, wherein one of A1 and A2 is N, the other one is CH, and all remaining substituents have the significances given herein before.

In another embodiment (xix) of the present invention, particular compounds of the present invention are selected from
1-(6-chloro-10-oxo-chromeno[3,2-c]pyridin-3-yl)pyrrolidine-3-carboxylic acid;
6-fluoro-3-pyrrolidin-1-yl-chromeno[3,2-c]pyridin-10-one;
9-chloro-2-pyrrolidin-1-yl-chromeno[2,3-b]pyridin-5-one; and
5-chloro-3-[3-(morpholine-4-carbonyl)pyrrolidin-1-yl]xanthen-9-one;
or pharmaceutically acceptable salts, or enantiomers, or diastereomers thereof.

Another embodiment of the present invention is (xx) a compound of formula I, or pharmaceutically acceptable salts, or enantiomers, or diastereomers thereof, wherein $R^5$ and R$^6$ together with nitrogen to which they are attached form oxopyrrolidinyl, azepanyl, diazepanyl, piperidinyl, hydroxypiperidinyl, carboxypiperidinyl, C$_{1-6}$alkylpiperazinyl, morpholinyl, 2,6-diazaspiro[3.4]octan-6-yl or 2,7-diazaspiro[4.4]nonan-2-yl, and all remaining substituents have the significances given herein before.

In another embodiment (xxi) of the present invention, particular compounds of the present invention are selected from
5-fluoro-3-(1-piperidyl)xanthen-9-one;
5-chloro-3-(3-hydroxy-1-piperidyl)xanthen-9-one;
3-(azepan-1-yl)-5-fluoro-xanthen-9-one;
1-(5-chloro-9-oxo-xanthen-3-yl)piperidine-3-carboxylic acid;
1-(5-fluoro-9-oxo-xanthen-3-yl)pyrrolidin-2-one;
5-fluoro-3-morpholino-xanthen-9-one;
5-fluoro-3-(4-methylpiperazin-1-yl)xanthen-9-one;
3-(2,6-diazaspiro[3.4]octan-6-yl)-5-fluoro-xanthen-9-one;
3-(2,7-diazaspiro[4.4]nonan-2-yl)-5-fluoro-xanthen-9-one; and
3-(1,4-diazepan-1-yl)-5-fluoro-xanthen-9-one;
or pharmaceutically acceptable salts, or enantiomers, or diastereomers thereof.

Another embodiment of the present invention is (xxii) a compound of formula I, wherein,
R$^1$ is halogen;
R$^2$, R$^3$ and R$^4$ are hydrogen;
R$^5$ and R$^6$ together with nitrogen to which they are attached form pyrrolidinyl or 3-carboxypyrrolidinyl;
X is —C(R$^9$)(R$^{10}$)—, wherein
    R$^9$ and R$^{10}$ are independently selected from hydrogen, C$_{1-6}$alkyl, haloC$_{1-6}$alkyl, C$_{1-6}$alkoxy, hydroxy, oxetanyl and halophenylCH(—O-carbonylC$_{1-6}$alkyl)-; or
    R$^9$ and R$^{10}$ together with carbon to which they are attached form

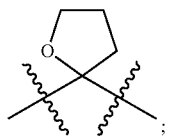 [SMILES: *C1(*)CCCO1 ; ";"]
;

A$^1$ CR$^7$, wherein R$^7$ is hydrogen or halogen;
A$^2$ CR$^8$, wherein R$^8$ is hydrogen or halogen;
Y is O;
or pharmaceutically acceptable salts, or enantiomers, or diastereomers thereof.

A further embodiment of the present invention is (xxiii) a compound of formula I, wherein,
R$^1$ is fluoro or chloro;
R$^2$, R$^3$ and R$^4$ are hydrogen;
R$^5$ and R$^6$ together with nitrogen to which they are attached form pyrrolidinyl or 3-carboxypyrrolidinyl;
X is —C(R$^9$)(R$^{10}$)—, wherein
    R$^9$ and R$^{10}$ are independently selected from hydrogen, methyl, trifluoromethyl, methoxy, hydroxy, oxetanyl and fluorochlorophenyl-CH(—O-carbonylmethyl)-; or
    R$^9$ and R$^{10}$ together with carbon to which they are attached form

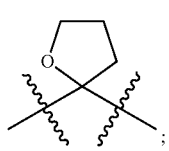 [SMILES: *C1(*)CCCO1 ; ";"]
;

A$^1$ is CR$^7$, wherein R$^7$ is hydrogen or chloro;
A$^2$ is CR$^8$, wherein R$^8$ is hydrogen or chloro;
Y is O;
or pharmaceutically acceptable salts, or enantiomers, or diastereomers thereof.

Another embodiment of the present invention is a (xxiii) compound of formula I, wherein,
R$^1$ is halogen;
R$^2$, R$^3$ and R$^4$ are hydrogen;
R$^5$ and R$^6$ together with nitrogen to which they are attached form pyrrolidinyl;
X is —C(R$^9$)(R$^{10}$)—, wherein
    R$^9$ and R$^{10}$ are independently selected from hydrogen, C$_{1-6}$alkyl, haloC$_{1-6}$alkyl, C$_{1-6}$alkoxy, hydroxy, oxetanyl and halophenylCH(—O-carbonylC$_{1-6}$alkyl)-; or
    R$^9$ and R$^{10}$ together with carbon to which they are attached form

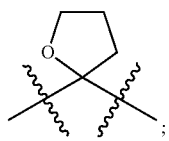 [SMILES: *C1(*)CCCO1 ; ";"]
;

A$^1$ CR$^7$, wherein R$^7$ is hydrogen or halogen;
A$^2$ CR$^8$, wherein R$^8$ is hydrogen or halogen;
Y is O;
or pharmaceutically acceptable salts, or enantiomers, or diastereomers thereof.

A further embodiment of the present invention is (xxiv) a compound of formula I, wherein,
R$^1$ is fluoro or chloro;
R$^2$, R$^3$ and R$^4$ are hydrogen;
R$^5$ and R$^6$ together with nitrogen to which they are attached form pyrrolidinyl;
X is —C(R$^9$)(R$^{10}$)—, wherein
    R$^9$ and R$^{10}$ are independently selected from hydrogen, methyl, trifluoromethyl, methoxy, hydroxy, oxetanyl and fluorochlorophenyl-CH(—O-carbonylmethyl)-; or
    R$^9$ and R$^{10}$ together with carbon to which they are attached form

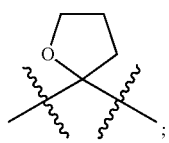 [SMILES: *C1(*)CCCO1 ; ";"]
;

A$^1$ is CR$^7$, wherein R$^7$ is hydrogen or chloro;
A$^2$ is CR$^8$, wherein R$^8$ is hydrogen or chloro;
Y is O;
or pharmaceutically acceptable salts, or enantiomers, or diastereomers thereof.

In another embodiment (xxv) of the present invention, particular compounds of the present invention are selected from
1-(5'-fluorospiro[tetrahydrofuran-2,9'-xanthene]-3'-yl)pyrrolidine;
1-(5-chloro-9-methyl-9H-xanthen-3-yl)pyrrolidine;
1-(5-chloro-9H-xanthen-3-yl)pyrrolidine;
1-(2,4,5-trichloro-9H-xanthen-3-yl)pyrrolidine;
1-[5-chloro-9-(oxetan-3-yl)-9H-xanthen-3-yl]pyrrolidine;
[(2-chloro-3-fluoro-phenyl)-(5-chloro-3-pyrrolidin-1-yl-9H-xanthen-9-yl)methyl]acetate;
5-chloro-3-pyrrolidin-1-yl-9-(trifluoromethyl)xanthen-9-ol;
1-[5-chloro-9-methoxy-9-(trifluoromethyl)xanthen-3-yl] pyrrolidine;
1-[5-chloro-9-(trifluoromethyl)-9H-xanthen-3-yl]pyrrolidine;
1-(5-fluoro-9H-xanthen-3-yl)pyrrolidine; and
1-(5-chloro-9-methyl-9H-xanthen-3-yl)pyrrolidine-3-carboxylic acid;
or pharmaceutically acceptable salts, or enantiomers, or diastereomers thereof.

In another embodiment (xxvi) of the present invention, a compound is selected from:
1-(5-chloro-9-oxo-thioxanthen-3-yl)pyrrolidine-3-carboxylic acid;
(3S)-1-(5-chloro-9-oxo-thioxanthen-3-yl)pyrrolidine-3-carboxylic acid; and
(3R)-1-(5-chloro-9-oxo-thioxanthen-3-yl)pyrrolidine-3-carboxylic acid;
or pharmaceutically acceptable salts, or enantiomers, or diastereomers thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^6$, X, Y, $A^1$ and $A^2$ are as defined above unless otherwise indicated. Furthermore, and unless explicitly otherwise stated, all reactions, reaction conditions, abbreviations and symbols have the meanings well known to a person of ordinary skill in organic chemistry.

General synthetic route for Compound Ia (Scheme 1)

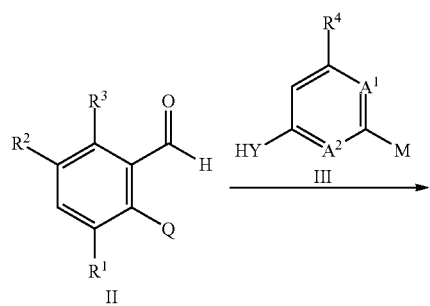

The compound of formula Ia can be prepared according to Scheme 1, wherein Q and M are independently selected from F, Cl, Br and I.

Coupling of substituted benzaldehyde II with aryl halide III affords benzaldehyde IV. The reaction can be carried out in the presence of a metal catalyst such as $CuCl_2$, and $Pd(dppf)_2Cl_2$, a ligand such as $PPh_3$ and Sphos and a suitable base such as $K_3PO_4$, in a suitable solvent such as NMP and DMF. Treatment of compound IV with an appropriate oxidant such as 2,3-dichloro-5,6-dicyano-1,4-benzoquinone and a suitable Lewis acid such as $FeCl_3$ in a suitable solvent such as 1,2-dichloroethane affords cyclized intermediate V. Coupling of intermediate V with compound $NHR^6R^7$ in the presence of a catalyst such as $CuCl_2$ and $Pd(dppf)_2Cl_2$, a ligand such as $PPh_3$ and Sphos and a suitable base such as $K_3PO_4$ and $Cs_2CO_3$ in a suitable solvent such as NMP and DMF affords compound Ia.

Alternative general synthetic route for Compound Ia (Scheme 2)

Scheme 2

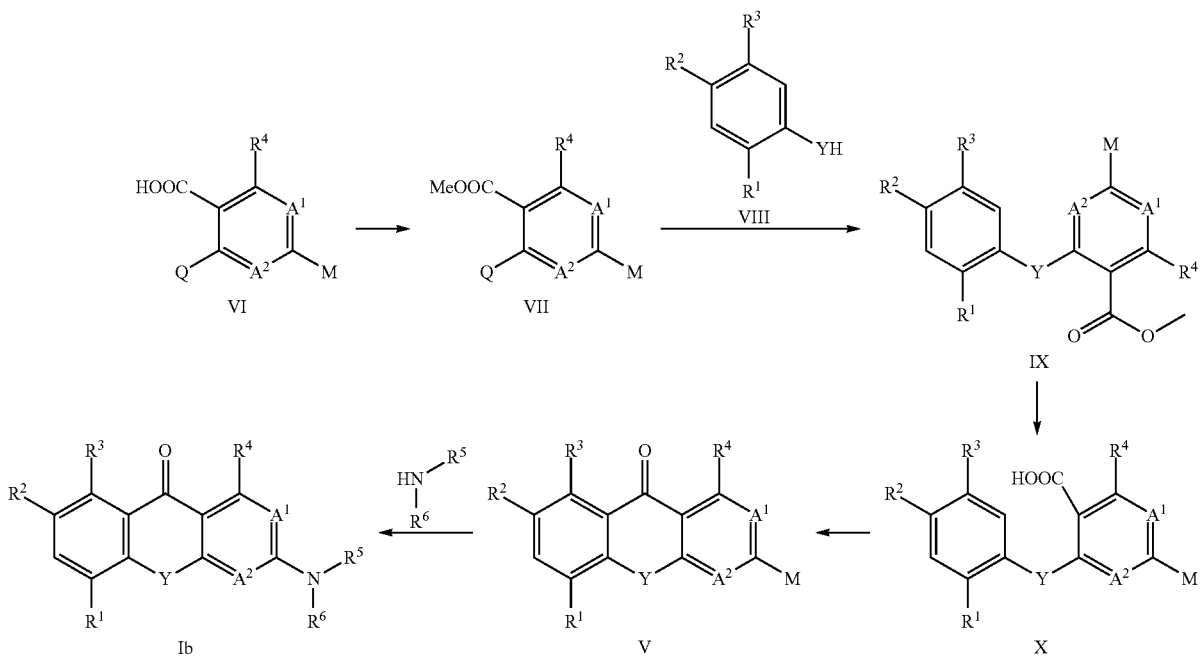

The compound of formula Ib can also be prepared according to Scheme 2, wherein Q and M are independently selected from F, Cl, Br and I.

Esterification of substituted acid VI with alcohol in the presence of suitable reagents such as $SOCl_2$ affords ester VII. Coupling of ester VII with intermediate VIII in the presence of a metal catalyst such as $CuCl_2$ and $Pd(dppf)_2Cl_2$, a ligand such as $PPh_3$ and Sphos and a suitable base such as $K_3PO_4$ and $Cs_2CO_3$, in a suitable solvent such as NMP and DMF, affords intermediate IX. Hydrolysis of compound IX with a suitable base such as NaOH affords acid X. Cyclization of acid X in the presence of a Lewis acid such as condensed sulfuric acid affords intermediate V. Coupling of intermediate V with compound $NHR^6R^7$ in the presence of a catalyst such as $CuCl_2$ and $Pd(dppf)_2Cl_2$, a ligand such as $PPh_3$, Sphos and a suitable base such as $K_3PO_4$ and $Cs_2CO_3$ in a suitable solvent such as NMP and DMF affords final compound Ib.

This invention also relates to a process for the preparation of a compound of formula I comprising the following step:

(a) coupling of a compound of formula (A)

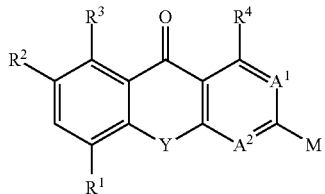

(A)

with a compound of formula (B)

$NHR^5R^6$ (B)

in the presence of a catalyst, a ligand and a base; wherein $R^1$ to $R^6$, Y, $A^1$ and $A^2$ are defined as above, M is F, Cl, Br or I;

the metal catalyst can be for example $CuCl_2$, or $Pd(dppf)_2Cl_2$;

the ligand can be for example $PPh_3$ or Sphos;

the base can be for example $K_3PO_4$ or $Cs_2CO_3$;

A compound of formula I when manufactured according to the above process is also an object of the invention.

Pharmaceutical Compositions and Administration

The invention also relates to a compound of formula I for use as therapeutically active substance. Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit cccDNA in HBV patients, consequently lead to the reduction of HBsAg and HBeAg (HBV e antigen) in serum. For example, such amount may be below the amount that is toxic to normal cells, or the mammal as a whole.

In one example, the pharmaceutically effective amount of the compound of the invention administered parenterally per dose will be in the range of about 0.1 to 100 mg/kg, alternatively about 0.1 to 50 mg/kg of patient body weight per day, with the typical initial range of compound used being 0.3 to 15 mg/kg/day. In another embodiment, oral unit dosage forms, such as tablets and capsules, preferably contain from about 25 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 to 500 mg of the compound of the invention compounded with about 90 to 300 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or pharmaceutically acceptable salts or enantiomers or diastereomers thereof.

In a further embodiment includes a pharmaceutical composition comprising a compound of Formula I, or pharmaceutically acceptable salts or enantiomers or diastereomers thereof, together with a pharmaceutically acceptable carrier or excipient.

Another embodiment includes a pharmaceutical composition comprising a compound of Formula I, or pharmaceutically acceptable salts or enantiomers or diastereomers thereof for use in the treatment of HBV infection.

Indications and Methods of Treatment

The compounds of the invention can inhibit cccDNA and have anti-HBV activity. Accordingly, the compounds of the invention are useful for the treatment or prophylaxis of HBV infection.

The invention relates to the use of a compound of formula I for the inhibition of cccDNA.

The invention also relates to the use of a compound of formula I for the inhibition of HBeAg.

The invention further relates to the use of a compound of formula I for the inhibition of HBsAg.

The invention relates to the use of a compound of formula I for the inhibition of HBV DNA.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, or enantiomers, diastereomers, prodrugs or pharmaceutically acceptable salts thereof.

BRIEF DESCRIPTION OF THE FIGURE(S)

FIG. 1: the result of Example 2 in cccDNA Southern Blot assay, it indicates that Example 2 dose-dependently reduced cccDNA level in HepDES19 cells.

Figure 2:
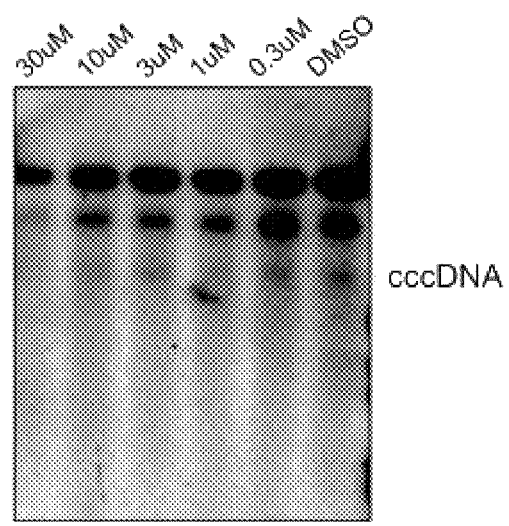

FIG. 2: the result of Example 3 in cccDNA Southern Blot assay, it indicates that Example 3 dose-dependently reduced cccDNA level in HepDES19 cells.

Figure 3:
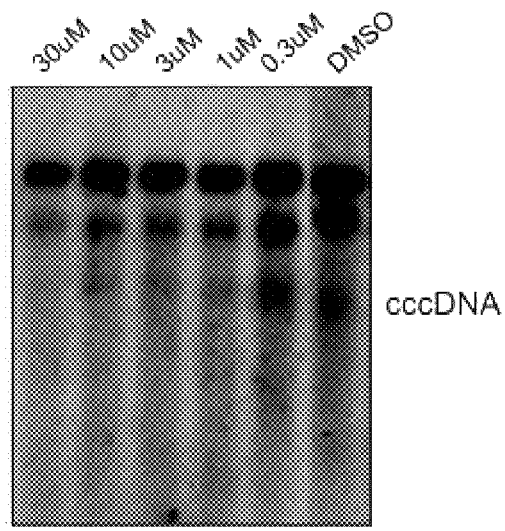

FIG. 3: the result of Example 4 in cccDNA Southern Blot assay, it indicates that Example 4 dose-dependently reduced cccDNA level in HepDES19 cells.

Figure 4:
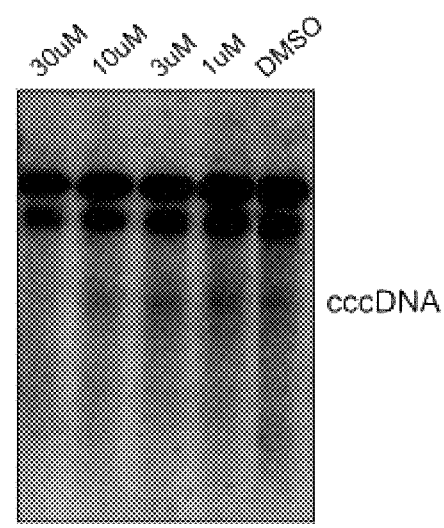

FIG. 4: the result of Example 5 in cccDNA Southern Blot assay, it indicates that Example 5 dose-dependently reduced cccDNA level in HepDES19 cells.

Figure 5:
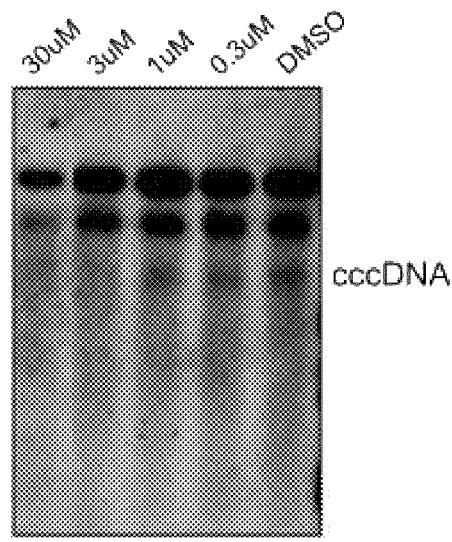

FIG. 5: the result of Example 7 in cccDNA Southern Blot assay, it indicates that Example 7 dose-dependently reduced cccDNA level in HepDES19 cells.

Figure 6:
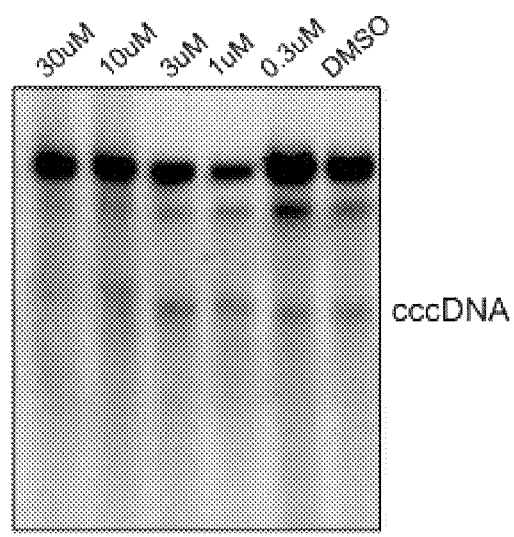

FIG. 6: the result of Example 26 in cccDNA Southern Blot assay, it indicates that Example 26 dose-dependently reduced cccDNA level in HepDES19 cells.

EXAMPLES

The invention will be more fully understood by reference to the following examples. They should not, however, be construed as limiting the scope of the invention.
Abbreviations used herein are as follows:
μL: microliter
μm: micrometer
μM: micromoles per liter
M: molarity
MHz: megahertz
min: minute
hr(s): hour(s)
mM: millimole per liter
nM: Nanomolar per liter
rt: room temperature
TFA: trifluoroacetic acid
Sphos: 2-dicyclohexylphosphino-2',6'-dimethoxybiphenyl
NMP: N-methyl-2-pyrrolidone
$PPh_3$: triphenylphosphine
PE: petroleum ether
DDQ: 2,3-Dichloro-5,6-dicyano-1,4-benzoquinone
DBU: 1,8-Diazabicyclo[5.4.0]undec-7-ene
DMAP: 4-dimethylaminopyridine
DMF: N,N-dimethylformamide
EtOAc: ethyl acetate
FBS: fetal bovine serum
HPLC: high performance liquid chromatography
MS (ESI): mass spectroscopy (electron spray ionization)
NMR: nuclear magnetic resonance
δ: chemical shift
obsd.: observed
TEA: triethylamine
$IC_{50}$: the concentration of a compound, which produces 50% of the inhibition effect for that target
HATU: 1-[bis(dimethylamino)methylene]-1H-1,2,3-triazolo[4,5-b]pyridinium 3-oxid hexafluorophosphate
NCS: N-chlorosuccinimide
Tet: Tetracycline
DMEM-F12: Dulbecco's Modified Eagle Medium: Nutrient Mixture F-12
NEAA: Non-Essential Amino Acids
PS: Penicillin Streptomycin
G418: Geneticin
DMSO: Dimethyl sulfoxide
EDTA: ethylenediaminetetraacetic acid
SDS: sodium dodecyl sulfate
RPM: revolutions per minute
TAE: tris-acetate electrophoresis
DIG: Digoxigenin
PHH: primary human hepatocytes
CLIA: Chemiluminescence Immuno Assay
PEG: polyethylene glycol
RCF: relative centrifugal force

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere.

Reagents were used as received from commercial suppliers without further purification unless otherwise noted.

PREPARATIVE EXAMPLES

Intermediate 1: 3-bromo-5-chloro-xanthen-9-one

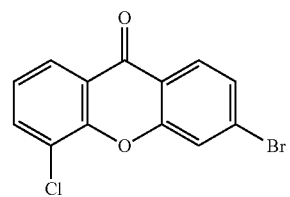

int-1

Intermediate 1 was prepared according to Scheme 3.

Scheme 3

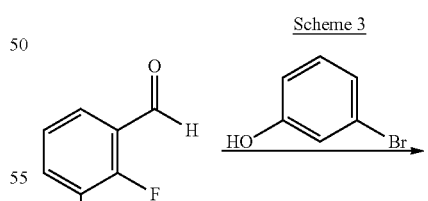

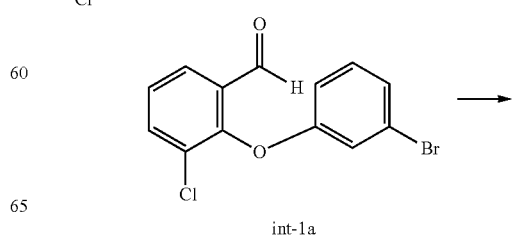

int-1a

Step 1: Preparation of 2-(3-bromophenoxy)-3-chloro-benzaldehyde

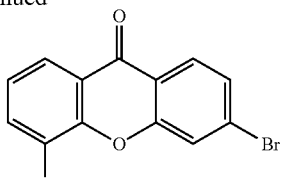

int-1

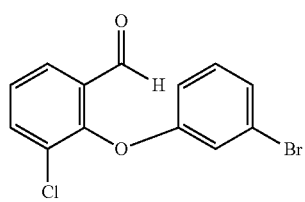

int-1a

To a solution of 3-chloro-2-fluoro-benzaldehyde (10.0 g, 63.29 mmol) in NMP (100 mL) was added 3-bromophenol (13.1 g, 75.95 mmol), CuCl$_2$ (0.42 g, 3.165 mmol), K$_3$PO$_4$ (26.8 g, 126.6 mmol) and PPh$_3$ (1.24 g, 4.747 mmol) at 25° C., then the mixture was stirred at 120° C. for 16 h. The reaction was quenched by addition of water (500 mL) and the resulting mixture was extracted with EtOAc (500 mL) for three times. The combined organic phase was washed with brine, dried over anhydrous Na$_2$SO$_4$ and concentrated under reduced pressure. The residue was purified by column chromatography on silica gel (elution with PE:EtOAc=20:1) to give 2-(3-bromophenoxy)-3-chloro-benzaldehyde (14.1 g, 71%) as oil. MS obsd. (ESI$^+$) [(M+H)$^+$]: 311.0.

Step 2: Preparation of 3-bromo-5-chloro-xanthen-9-one int-1

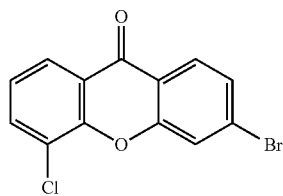

To a mixture of 2-(3-bromophenoxy)-3-chloro-benzaldehyde (12.0 g, 38.72 mmol) in 1,2-dichloroethane (200 mL) was added 2,3-dichloro-5,6-dicyano-1,4-benzoquinone (26.2 g, 116.2 mmol) and FeCl$_3$.6H$_2$O (31.2 g, 116.2 mmol) at 25° C. Then the mixture was stirred at 100° C. for 16 hours. The resulting reaction mixture was poured into water (250 mL) and extracted with DCM (500 mL) for three times. The combined organic phase was dried with anhydrous Na$_2$SO$_4$ and concentrated under reduced pressure. The residue was purified by column chromatography on silica gel (elution with PE:EtOAc=20:1) to give 3-bromo-5-chloro-xanthen-9-one (7.6 g, 63.0%) as a pale green solid, MS obsd. (ESI$^+$) [(M+H)$^+$]: 309.0.

Intermediate 2: 3-bromo-5-fluoro-2-methyl-xanthen-9-one int-2

Intermediate 2 was prepared according to Scheme 4.

Scheme 4

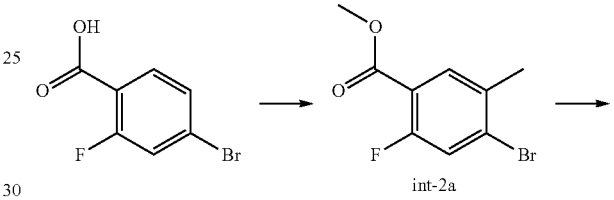

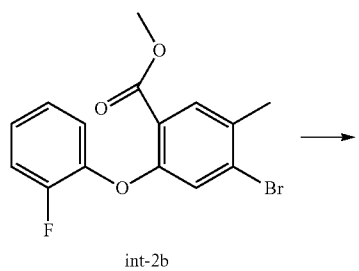

int-2b

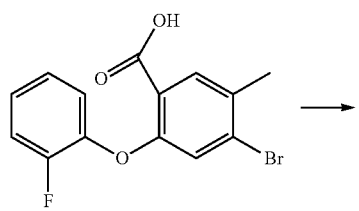

int-2c

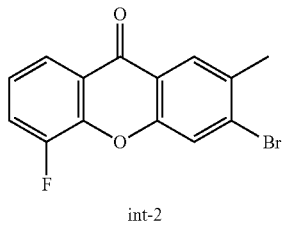

int-2

Step 1: Preparation of Methyl 4-bromo-2-fluoro-5-methyl-benzoate

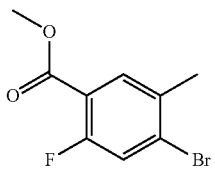
int-2a

To a mixture of 4-bromo-2-fluoro-5-methyl-benzoic acid (1.5 g, 6.44 mmol) in MeOH (25 mL) was added SOCl$_2$ (2.3 g, 19.31 mmol) dropwise at 0° C. and the mixture was then stirred at 70° C. for 2 hours. After the reaction was complete, the mixture was concentrated under reduced pressure to afford the crude of methyl 4-bromo-2-fluoro-5-methyl-benzoate (1.6 g, 100%) as a pale solid, which was used in the next step without further purification.

Step 2: Preparation of Methyl 4-bromo-2-(2-fluorophenoxy)-5-methyl-benzoate

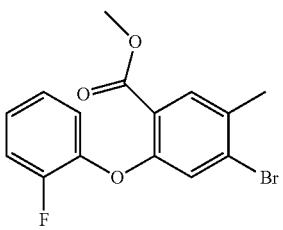
int-2b

To a solution of methyl 4-bromo-2-fluoro-5-methyl-benzoate (1.9 g, 7.69 mmol) in DMF (25 mL) was added 2-fluorophenol (1.0 g, 9.23 mmol), Cu powder (2.9 g, 46.14 mmol) and K$_2$CO$_3$ (2.1 g, 15.38 mmol) at 20° C., the mixture was then stirred at 100° C. for 16 hours. The resulting mixture was cooled to 20° C. and filtered, the obtained cake was washed with EtOAc (100 mL). The combined filtrate was washed with water (50 mL) and brine (100 mL), dried over anhydrous Na$_2$SO$_4$ and concentrated under reduced pressure. The residue was purified by column chromatography on silica gel (elution with PE:EtOAc=100:1 to 5:1) to afford methyl 4-bromo-2-(2-fluorophenoxy)-5-methyl-benzoate (600.0 mg, yield: 23.08%) and recycled 4-bromo-2-fluoro-5-methyl-benzoate (890.0 mg). Methyl 4-bromo-2-(2-fluorophenoxy)-5-methyl-benzoate, MS obsd. (ESI$^+$) [(M+H)$^+$]: 339.0.

Step 3: Preparation of 4-bromo-2-(2-fluorophenoxy)-5-methyl-benzoic acid

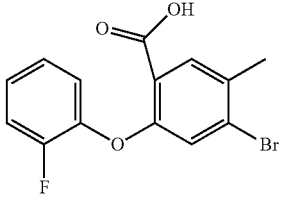
int-2c

A mixture of methyl 4-bromo-2-(2-fluorophenoxy)-5-methyl-benzoate (0.5 g, 1.47 mmol), NaOH (180.0 mg, 4.42 mmol) in MeOH/H$_2$O (20 mL/4 mL) was stirred at 60° C. for 4 hours. The resulting mixture was concentrated under reduced pressure and the residue was redissolved in water (20 mL). The solution was adjusted to pH=3-4 by addition of 1N HCl dropwise and the resulting mixture was extracted with EtOAc (80 mL) three times. The combined organic layer was dried over anhydrous Na$_2$SO$_4$ and concentrated under reduced pressure to afford 4-bromo-2-(2-fluorophenoxy)-5-methyl-benzoic acid (550.0 mg, crude) as a pale-white solid, which was used in the next step without further purification. MS obsd. (ESI$^+$) [(M+H)$^+$]: 324.8.

Step 4: Preparation of 3-bromo-5-fluoro-2-methyl-xanthen-9-one

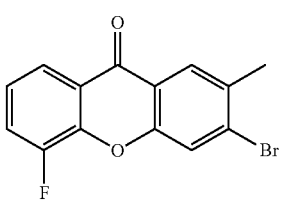
int-2

A solution of 4-bromo-2-(2-fluorophenoxy)-5-methyl-benzoic acid (0.45 g, 0.308 mmol) in condensed sulfuric acid (20 mL) was stirred at 90° C. for 15 hours under N$_2$ atmosphere. The reaction mixture was poured into ice and stirred for 15 min. The resulting mixture was extracted with EtOAc (60 mL) and the organic layer was dried over anhydrous Na$_2$SO$_4$ and concentrated under reduced pressure to afford 3-bromo-5-fluoro-2-methyl-xanthen-9-one (0.4 g, 61.54%) as a pale-white solid. MS obsd. (ESI$^+$) [(M+H)$^+$]: 312.4.

Intermediate 3: 3-bromo-5-fluoro-xanthen-9-one

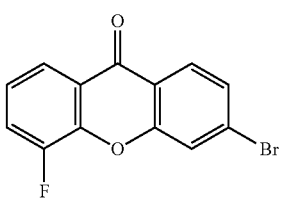
int-3

Intermediate 3 was prepared according to Scheme 5.

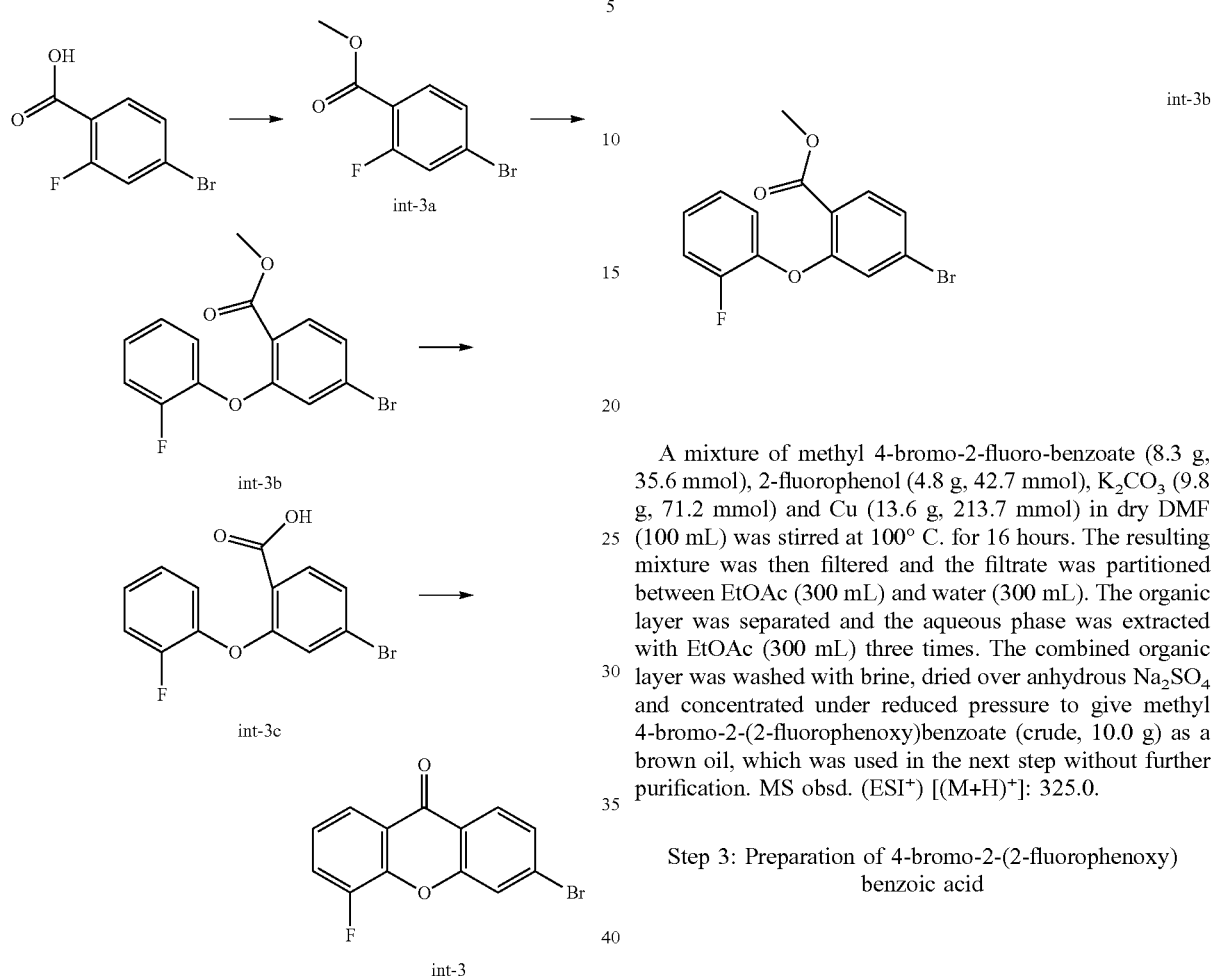

Step 1: Preparation of Methyl 4-bromo-2-fluoro-benzoate

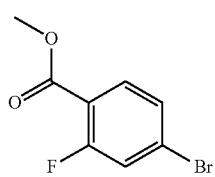

int-3a

To a mixture of 4-bromo-2-fluoro-benzoic acid (1.5 g, 6.44 mmol) in MeOH (25 mL) was added $SOCl_2$ (2.3 g, 19.31 mmol) dropwise at 0° C. and the mixture was then stirred at 70° C. for 2 hours. After the reaction was complete, the mixture was concentrated under reduced pressure to afford the crude of methyl 4-bromo-2-fluoro-benzoate (1.6 g, 100%, crude) as a pale solid, which was used in the next step without further purification.

Step 2: Preparation of Methyl 4-bromo-2-(2-fluorophenoxy)benzoate

A mixture of methyl 4-bromo-2-fluoro-benzoate (8.3 g, 35.6 mmol), 2-fluorophenol (4.8 g, 42.7 mmol), $K_2CO_3$ (9.8 g, 71.2 mmol) and Cu (13.6 g, 213.7 mmol) in dry DMF (100 mL) was stirred at 100° C. for 16 hours. The resulting mixture was then filtered and the filtrate was partitioned between EtOAc (300 mL) and water (300 mL). The organic layer was separated and the aqueous phase was extracted with EtOAc (300 mL) three times. The combined organic layer was washed with brine, dried over anhydrous $Na_2SO_4$ and concentrated under reduced pressure to give methyl 4-bromo-2-(2-fluorophenoxy)benzoate (crude, 10.0 g) as a brown oil, which was used in the next step without further purification. MS obsd. (ESI$^+$) [(M+H)$^+$]: 325.0.

Step 3: Preparation of 4-bromo-2-(2-fluorophenoxy) benzoic acid

A mixture of methyl 4-bromo-2-(2-fluorophenoxy)benzoate (9.75 g, 30.0 mmol, crude prepared above), NaOH (3.6 g, 90.0 mmol) in a mixed solvent of methanol (100 mL) and water (20 mL) was stirred at 60° C. for 4 hours. The resulting mixture was adjusted to pH 4 with concentrated HCl to yield a suspension. The solid was collected by filtration and dried to give 4-bromo-2-(2-fluorophenoxy) benzoic acid (crude, 5.1 g) as a white solid, which was used in the next step without further purification. MS obsd. (ESI$^+$) [(M+H)$^+$]: 311.0.

Step 4: Preparation of 3-bromo-5-fluoro-xanthen-9-one

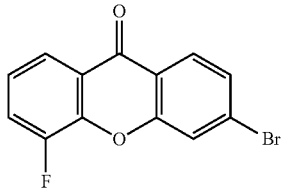

int-3

A mixture of 4-bromo-2-(2-fluorophenoxy) benzoic acid (5.1 g, 16.4 mmol, crude prepared above) and $H_2SO_4$ (50.0 mL) was stirred at 100° C. for 16 hours. The mixture was poured into ice (100.0 g) and extracted with EtOAc (400 mL) three times. The combined organic layer was washed with brine, dried over anhydrous $Na_2SO_4$ and concentrated under reduced pressure to give 3-bromo-5-fluoro-xanthen-9-one (3.2 g, crude) as a white solid, which was used in next step without further purification. MS obsd. (ESI$^+$) [(M+H)$^+$]: 293.0.

Intermediate 4:
3-bromo-5-chloro-2-methyl-xanthen-9-one

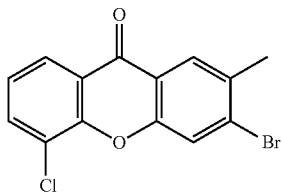

int-4

Intermediate 4 was prepared in analogy to the procedure described for the preparation of intermediate 3 by using methyl 3-chloro-2-fluoro-benzoate and 3-bromo-4-methyl-phenol as the starting materials instead of methyl 4-bromo-2-fluoro-benzoate and 2-fluorophenol in Step 2.

Intermediate 5:
3-bromo-2-chloro-5-fluoro-xanthen-9-one

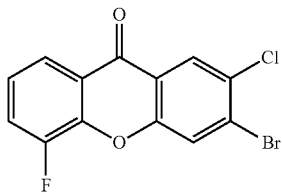

int-5

Intermediate 5 was prepared in analogy to the procedure described for the preparation of intermediate 2 by using 4-bromo-5-chloro-2-fluoro-benzoic acid as the starting material instead of 4-bromo-2-fluoro-5-methyl-benzoic acid in Step 1.

Intermediate 6:
6-bromo-2-chloro-4-fluoro-xanthen-9-one

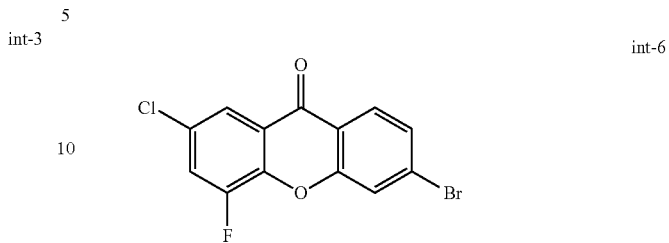

int-6

Intermediate 6 was prepared in analogy to the procedure described for the preparation of intermediate 3 by using 4-chloro-2-fluoro-phenol as the starting material instead of 2-fluorophenol in Step 2.

Intermediate 7:
3-bromo-5-(trifluoromethyl)xanthen-9-one

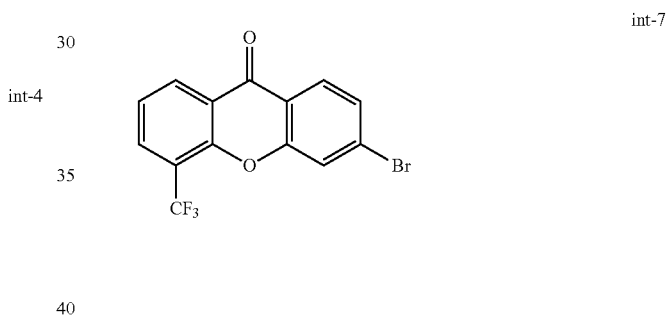

int-7

Intermediate 7 was prepared in analogy to the procedure described for the preparation of intermediate 3 by using 2-(trifluoromethoxy)phenol as the starting material instead of 2-fluorophenol in Step 2.

Intermediate 8:
6-bromo-4-chloro-1-methoxy-xanthen-9-one

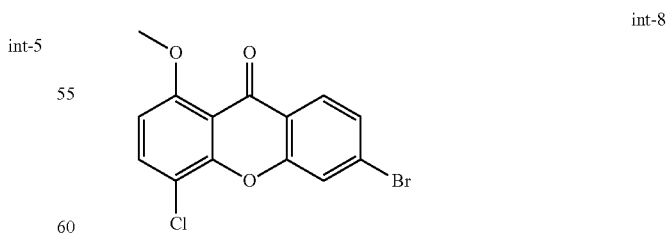

int-8

Intermediate 8 was prepared in analogy to the procedure described for the preparation of intermediate 3 by using 2-chloro-5-methoxy-phenol as the starting material instead of 2-fluorophenol in Step 2.

Intermediate 9:
6-bromo-1-chloro-4-fluoro-xanthen-9-one

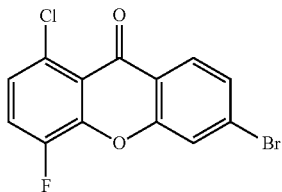

int-9

Intermediate 9 was prepared in analogy to the procedure described for the preparation of intermediate 3 by using 5-chloro-2-fluoro-phenol as the starting material instead of 2-fluorophenol in Step 2.

Intermediate 10:
6-bromo-1,4-dichloro-xanthen-9-one

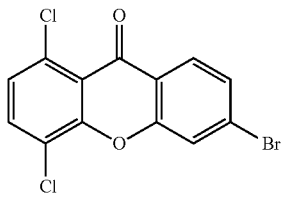

int-10

Intermediate 10 was prepared in analogy to the procedure described for the preparation of intermediate 3 by using 2,5-dichlorophenol as the starting material instead of 2-fluorophenol in Step 2.

Intermediate 11:
6-bromo-4-chloro-1-methyl-xanthen-9-one

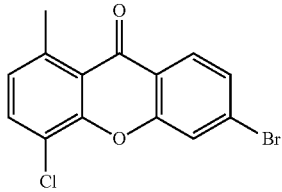

int-11

Intermediate 11 was prepared in analogy to the procedure described for the preparation of intermediate 3 by using 2-dichloro-5-methyl-phenol as the starting material instead of 2-fluorophenol in Step 2.

Intermediate 12: 3,6-dichlorochromeno[3,2-c]pyridin-10-one

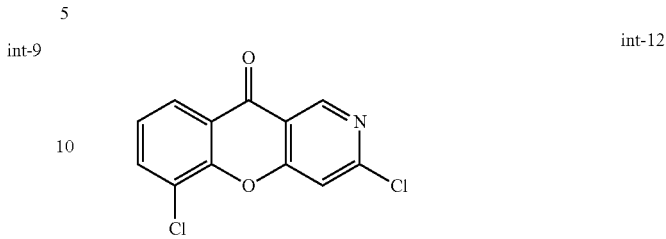

int-12

Intermediate 12 was prepared in analogy to the procedure described for the preparation of intermediate 3 by using methyl 4,6-dichloropyridine-3-carboxylate and 2-chlorophenol as the starting materials instead of methyl 4-bromo-2-fluoro-benzoate and 2-fluorophenol in Step 2.

Intermediate 13:
3-bromo-5-chloro-2-fluoro-xanthen-9-one

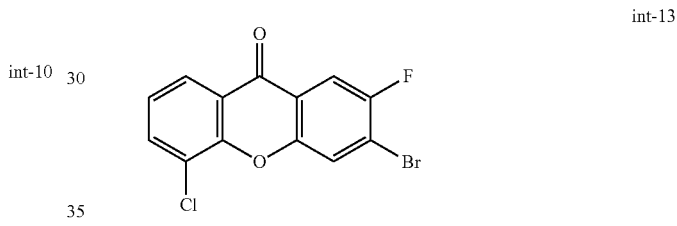

int-13

Intermediate 13 was prepared in analogy to the procedure described for the preparation of intermediate 3 by using 4-bromo-2,5-difluoro-benzoic acid as the starting material instead of 4-bromo-2-fluoro-5-methyl-benzoic acid in Step 1 and using 2-chlorophenol as the starting material instead of 2-fluorophenol in Step 2.

Intermediate 14:
3-bromo-2,5-dichloro-xanthen-9-one

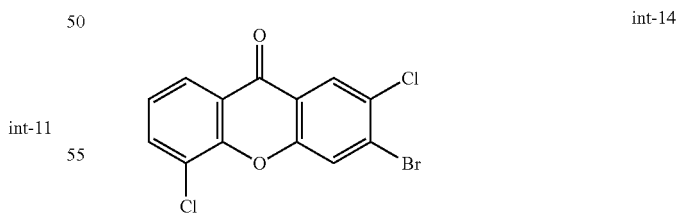

int-14

Intermediate 14 was prepared in analogy to the procedure described for the preparation of intermediate 3 by using 3-chloro-2-fluoro-benzoic acid as the starting material instead of 4-bromo-2-fluoro-5-methyl-benzoic acid in Step 1 and using 3-bromo-4-chloro-phenol as the starting material instead of 2-fluorophenol in Step 2.

Intermediate 15:
6-bromo-4-chloro-9-oxo-xanthene-1-carbonitrile

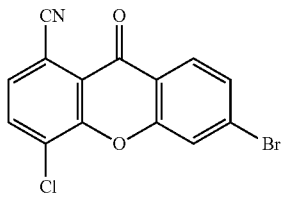

int-15

Step 1: Preparation of 6-bromo-4-chloro-1-fluoro-xanthen-9-one

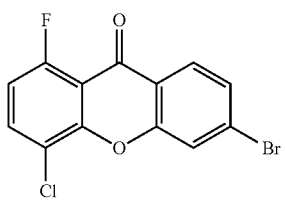

int-15a

6-Bromo-4-chloro-1-fluoro-xanthen-9-one was prepared in analogy to the procedure described for the preparation of intermediate 3 by using 2-chloro-5-fluoro-phenol as the starting material instead of 2-fluorophenol in Step 2.

Step 2: Preparation of 6-bromo-4-chloro-9-oxo-xanthene-1-carbonitrile

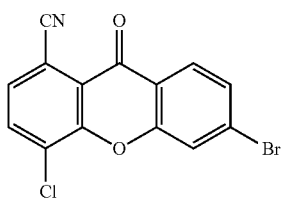

int-15

To a mixture of methyl 4-bromo-2-fluoro-5-methyl-benzoate (0.3 g, 0.920 mmol) in DMSO (3.0 mL) was added NaCN (30.0 mg, 0.612 mmol) at 25° C. After being stirred at 90° C. for 16 hours, the resulting mixture was poured into water (20.0 mL) and then extracted with EtOAc (50.0 mL). The organic phase was dried over $Na_2SO_4$ and concentrated under reduced pressure. The residue was purified by column chromatograph on silica gel (elution with PE:EtOAc=20:1 to 5:1) to give 6-bromo-4-chloro-9-oxo-xanthene-1-carbonitrile (0.1 g, 32.6%) as a yellow solid. MS obsd. (ESI+) [(M+H)+]: 323.9.

Intermediate 16:
3-bromo-2,5-difluoro-xanthen-9-one

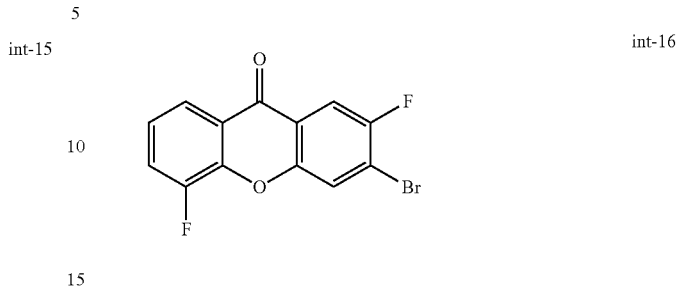

int-16

Intermediate 16 was prepared in analogy to the procedure described for the preparation of intermediate 2 by using 4-bromo-2,5-difluoro-benzoic acid as the starting material instead of 4-bromo-2-fluoro-5-methyl-benzoic acid in Step 1.

Intermediate 17: 2-chloro-9-fluoro-chromeno[2,3-b]pyridin-5-one

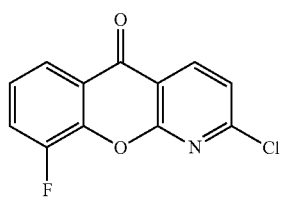

int-17

Intermediate 17 was prepared in analogy to the procedure described for the preparation of intermediate 2 by using 4,6-dichloropyridine-3-carboxylic acid as starting material instead of 4-bromo-2-fluoro-5-methyl-benzoic acid in the Step 1.

Intermediate 18:
6-bromo-4-chloro-1-(trifluoromethyl)xanthen-9-one

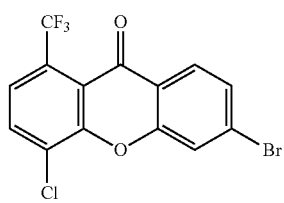

int-18

Intermediate 18 was prepared in analogy to the procedure described for the preparation of intermediate 3 by using 2-chloro-5-(trifluoromethyl)phenol as the starting material instead of 2-fluorophenol in Step 2.

Intermediate 19: 3-bromo-2-chloro-5-fluoro-xanthen-9-one

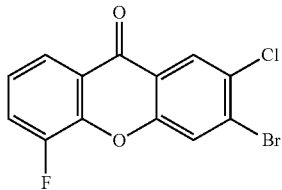

int-19

Intermediate 19 was prepared in analogy to the procedure described for the preparation of intermediate 1 by using 2,3-difluorobenzaldehyde and 3-bromo-4-chloro-phenol as the starting materials instead of 3-chloro-2-fluoro-benzaldehyde and 3-bromophenol in Step 1.

Example 1: 5-chloro-3-pyrrolidin-1-yl-xanthen-9-one

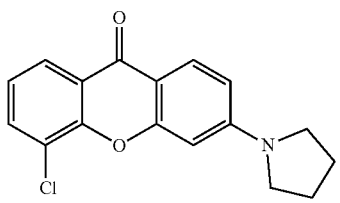

1

To a mixture of 3-bromo-5-chloro-xanthen-9-one (intermediate 1, 0.1 g, 0.325 mmol) in NMP (2 mL) was added pyrrolidine (46.2 mg, 0.650 mmol) and K$_3$PO$_4$ (0.14 g, 0.650 mmol) at 25° C. Then the mixture was stirred at 90° C. for 16 hours. The resulting mixture was poured into water (30 mL) and extracted with EtOAc (50 mL) for three times. The combined organic layer was washed with brine, dried over anhydrous Na$_2$SO$_4$ and concentrated under reduced pressure. The residue was purified by recrystallization (EtOAc, 10 mL) to give 5-chloro-3-pyrrolidin-1-yl-xanthen-9-one (33.0 mg, 33.8%) as a yellow solid. $^1$H NMR (400 MHz, DMSO-d$_6$): δ ppm 8.091-8.071 (d, J=8.0 Hz, 1H), 7.973-7.933 (m, 2H), 7.425-7.386 (m, 1H), 6.784-6.757 (m, 1H), 6.509-6.505 (d, J=1.6 Hz, 1H), 3.449-3.418 (t, J=6.8 Hz, 4H), 2.032-1.998 (t, J=6.5 Hz, 4H). MS obsd. (ESI$^+$) [(M+H)$^+$]: 300.1.

Example 2: 1-(5-chloro-9-oxo-xanthen-3-yl)pyrrolidine-3-carboxylic acid

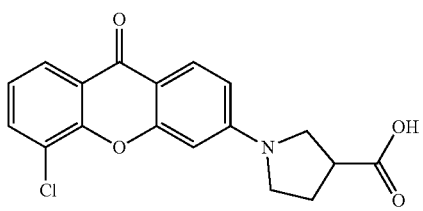

2

To a mixture of 3-bromo-5-chloro-xanthen-9-one (intermediate 1, 0.07 g, 0.226 mmol) in NMP (2.0 mL) was added pyrrolidine-3-carboxylic acid (39.1 mg, 0.339 mmol, vendor: Accela ChemBio Inc., CAS #: 59378-87-9, Cat.#: as SY008997) and K$_3$PO$_4$ (0.096 g, 0.452 mmol) at 25° C. Then the mixture was stirred at 90° C. for 16 hours. The resulting mixture was poured into water (30 mL) and extracted with EtOAc (50 mL) for three times. The combined organic phase was washed with brine, dried over anhydrous Na$_2$SO$_4$ and concentrated under reduced pressure. The residue was purified by preparative HPLC to give 1-(5-chloro-9-oxo-xanthen-3-yl)pyrrolidine-3-carboxylic acid (35.0 mg, 45.0%) as a yellow solid. $^1$H NMR (DMSO-d$_6$, 400 MHz): δ ppm 12.61 (br s, 1H), 8.08 (dd, J=7.9, 1.6 Hz, 1H), 7.83-8.01 (m, 2H), 7.41 (t, J=7.8 Hz, 1H), 6.78 (dd, J=9.0, 2.3 Hz, 1H), 6.54 (d, J=2.3 Hz, 1H), 3.56-3.76 (m, 2H), 3.42-3.56 (m, 2H), 3.22-3.31 (m, 1H), 2.12-2.40 (m, 2H). MS obsd. (ESI$^+$) [(M+H)$^+$]: 344.1.

Example 3: (3R)-1-(5-chloro-9-oxo-xanthen-3-yl)pyrrolidine-3-carboxylic acid

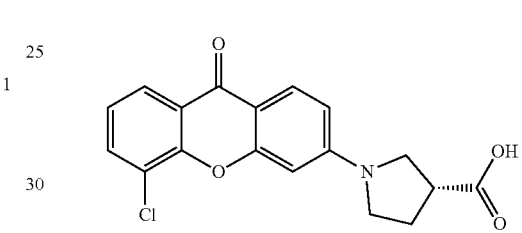

3

To a mixture of 3-bromo-5-chloro-xanthen-9-one (intermediate 1, 0.12 g, 0.388 mmol) in NMP (5.0 mL) was added (R)-pyrrolidine-3-carboxylic acid (89.3 mg, 0.775 mmol, vendor: Accela ChemBio Inc., CAS #: 72580-54-2, Cat.#: as SY010178) and K$_3$PO$_4$ (0.165 g, 0.452 mmol) at 25° C. Then the mixture was stirred at 90° C. for 16 hours. The resulting mixture was poured into water (30 mL) and extracted with EtOAc (50 mL) for three times. The combined organic phase was washed with brine, dried over anhydrous Na$_2$SO$_4$ and concentrated under reduced pressure. The residue was purified by preparative HPLC to give (3R)-1-(5-chloro-9-oxo-xanthen-3-yl)pyrrolidine-3-carboxylic acid (48.0 mg, 36.0%) as a yellow solid. $^1$H NMR (DMSO-d$_6$, 400 MHz): δ ppm 12.60 (br s, 1H), 8.07 (dd, J=1.59, 7.95 Hz, 1H), 7.94 (t, J=9.51 Hz, 2H), 7.40 (t, J=7.89 Hz, 1H), 6.77 (dd, J=2.26, 8.99 Hz, 1H), 6.52 (d, J=2.20 Hz, 1H), 3.57-3.68 (m, 2H), 3.37-3.54 (m, 2H), 3.23-3.31 (m, 1H), 2.16-2.33 (m, 2H). MS obsd. (ESI$^+$) [(M+H)$^+$]: 343.9.

Example 4: (3S)-1-(5-chloro-9-oxo-xanthen-3-yl)pyrrolidine-3-carboxylic acid

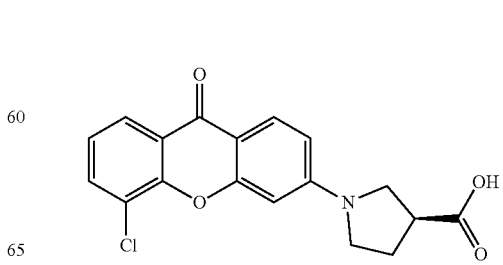

4

To a mixture of 3-bromo-5-chloro-xanthen-9-one (intermediate 1, 0.10 g, 0.323 mmol) in NMP (5.0 mL) was added (S)-pyrrolidine-3-carboxylic acid (74.4 mg, 0.646 mmol, vendor: Accela ChemBio Inc., CAS #: 72580-53-1, Cat.#: as SY010177) and $K_3PO_4$ (0.137 g, 0.646 mmol) at 25° C. Then the mixture was stirred at 90° C. for 16 hours. The resulting mixture was poured into water (30 mL) and extracted with EtOAc (50 mL) for three times. The combined organic phase was washed with brine, dried over anhydrous $Na_2SO_4$ and concentrated under reduced pressure. The residue was purified by preparative HPLC to give (3S)-1-(5-chloro-9-oxo-xanthen-3-yl)pyrrolidine-3-carboxylic acid (48.0 mg, 30.6%) as a yellow solid. $^1$H NMR (methanol-$d_4$, 400 MHz): δ ppm 8.15 (dd, J=1.51, 8.03 Hz, 1H), 8.06 (d, J=8.78 Hz, 1H), 7.84 (dd, J=1.51, 7.78 Hz, 1H), 7.36 (t, J=7.91 Hz, 1H), 6.78 (dd, J=2.26, 9.03 Hz, 1H), 6.57 (d, J=2.26 Hz, 1H), 3.72 (d, J=6.78 Hz, 2H), 3.42-3.66 (m, 2H), 3.34-3.40 (m, 1H), 2.29-2.57 (m, 2H). MS obsd. (ESI$^+$) [(M+H)$^+$]: 344.0.

Example 5: 1-(5-fluoro-9-oxo-xanthen-3-yl)pyrrolidine-3-carboxylic acid

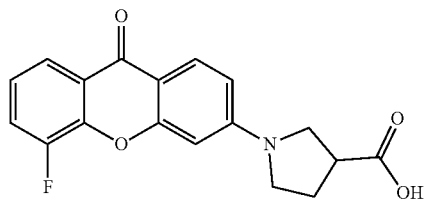

5

Step 1: Preparation of Methyl 1-(5-fluoro-9-oxo-xanthen-3-yl)pyrrolidine-3-carboxylate

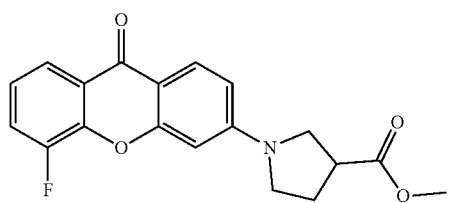

5a

A mixture of 3-bromo-5-fluoro-xanthen-9-one (intermediate 3, 0.2 g, 0.68 mmol), methyl pyrrolidine-3-carboxylate hydrochloride (0.264 g, 2.05 mmol, vendor: Accela ChemBio Inc., CAS #: 198959-37-4, Cat.#: as SY008084), $K_2CO_3$ (0.189 g, 1.36 mmol), Cu (0.26 g, 4.09 mmol) in DMF (4.0 mL) was stirred at 140° C. for 10 hours. The mixture was cooled to room temperature and filtered, and the filtrate was partitioned between ethyl acetate (20 mL) and water (20 mL). The organic phase was separated out and the aqueous phase was extracted with EtOAc (30 mL) three times. The combined organic layer was washed with brine, dried over anhydrous $Na_2SO_4$ and concentrated under reduced pressure to give the crude of methyl 1-(5-fluoro-9-oxo-xanthen-3-yl) pyrrolidine-3-carboxylate (0.12 g) as a brown oil, which was used in the next step without further purification. MS obsd. (ESI$^+$) [(M+H)$^+$]: 342.2.

Step 2: Preparation of 1-(5-fluoro-9-oxo-xanthen-3-yl)pyrrolidine-3-carboxylic acid

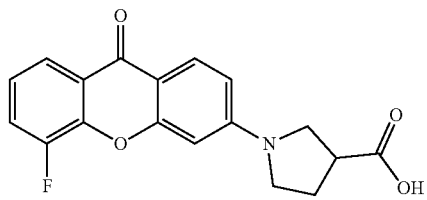

5

A mixture of methyl 1-(5-fluoro-9-oxo-xanthen-3-yl)pyrrolidine-3-carboxylate (0.12 g, 0.35 mmol, crude, prepared above), NaOH (0.07 g, 1.76 mmol) in a mixed solvent of THF (2 mL), MeOH (2 mL) and water (0.5 mL) was stirred at 50° C. for 3 hours. The resulting mixture was adjusted to pH around 4 with 2N HCl and then extracted with EtOAc (25 mL). The organic layer was washed with brine, dried over anhydrous $Na_2SO_4$ and concentrated under reduced pressure to give the crude of 1-(5-fluoro-9-oxo-xanthen-3-yl)pyrrolidine-3-carboxylic acid, which was recrystallized in MeOH to give 1-(5-fluoro-9-oxo-xanthen-3-yl)pyrrolidine-3-carboxylic acid (0.024 g, 20.8%) as a yellow solid. $^1$H NMR (DMSO-$d_6$, 400 MHz): δ ppm 12.43-12.81 (m, 1H), 7.88-7.98 (m, 2H), 7.68-7.77 (m, 1H), 7.32-7.41 (m, 1H), 6.72-6.79 (m, 1H), 6.55 (d, J=1.5 Hz, 1H), 3.56-3.68 (m, 2H), 3.44-3.51 (m, 2H), 3.22-3.28 (m, 1H), 2.16-2.31 (m, 2H). MS obsd. (ESI$^+$) [(M+H)$^+$]: 328.2.

Example 6: 1-(5-chloro-9-oxo-thioxanthen-3-yl)pyrrolidine-3-carboxylic acid

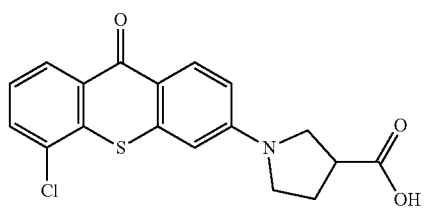

6

Example 6 was prepared according to Scheme 6:

Scheme 6

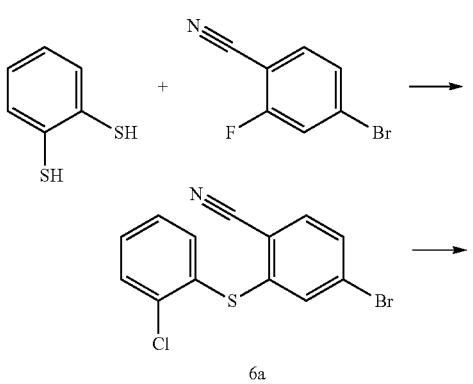

6a

-continued

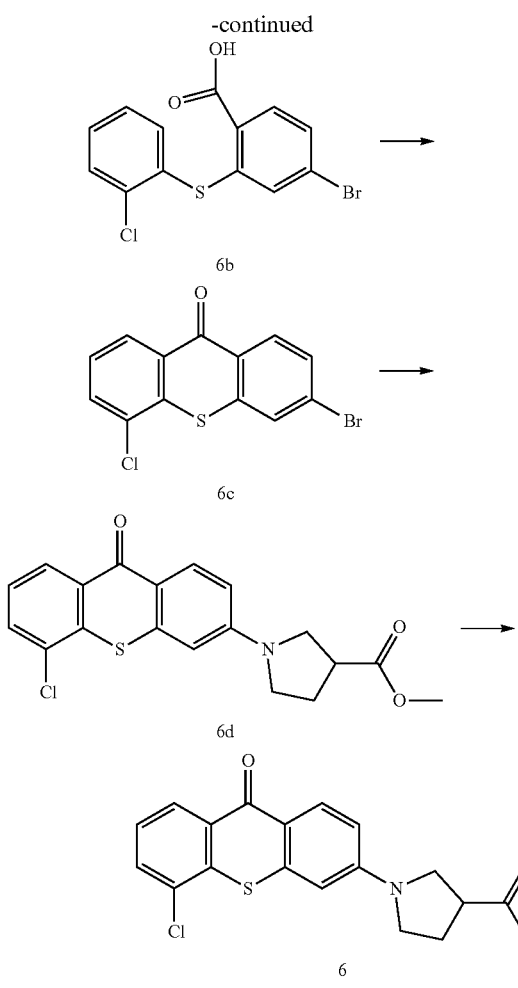

Step 1: Preparation of 4-bromo-2-(2-chlorophenyl)sulfanyl-benzonitrile

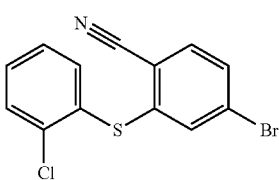

To a solution of 4-bromo-2-fluoro-benzonitrile (0.8 g, 4.0 mmol), 2-chlorobenzenethiol (0.58 g, 4.0 mmol) in dioxane (15 mL) was added K₂CO₃ (1.7 g, 12.0 mmol) at 25° C. After being stirred at 60° C. for 10 hours, the resulting mixture was filtered and the filtrate was concentrated under reduced pressure. The residue was stirred with petroleum ether (30 mL) and then filtered to give 4-bromo-2-(2-chlorophenyl)sulfanyl-benzonitrile (0.7 g, 54.3%) as a white solid. MS obsd. (ESI⁺) [(M+H)⁺]: 324.1.

Step 2: Preparation of 4-bromo-2-(2-chlorophenyl)sulfanyl-benzoic acid

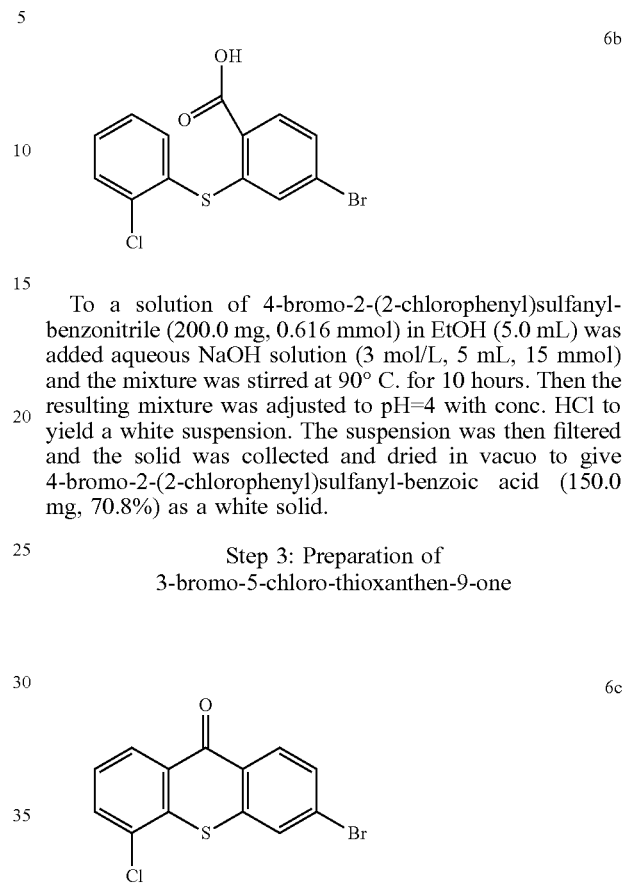

To a solution of 4-bromo-2-(2-chlorophenyl)sulfanyl-benzonitrile (200.0 mg, 0.616 mmol) in EtOH (5.0 mL) was added aqueous NaOH solution (3 mol/L, 5 mL, 15 mmol) and the mixture was stirred at 90° C. for 10 hours. Then the resulting mixture was adjusted to pH=4 with conc. HCl to yield a white suspension. The suspension was then filtered and the solid was collected and dried in vacuo to give 4-bromo-2-(2-chlorophenyl)sulfanyl-benzoic acid (150.0 mg, 70.8%) as a white solid.

Step 3: Preparation of 3-bromo-5-chloro-thioxanthen-9-one

A solution of 4-bromo-2-(2-chlorophenyl)sulfanyl-benzoic acid (100 mg, 0.29 mmol) in condensed sulfuric acid (5 mL) was stirred at 90° C. for 8 hours under N₂ atmosphere. The reaction mixture was poured into water (25 mL). The resulting mixture was extracted with EtOAc (30 mL) three times. The combined organic layer was washed by brine (20 mL), dried over anhydrous Na₂SO₄ and concentrated under reduced pressure to afford the crude of 3-bromo-5-chloro-thioxanthen-9-one (100 mg, 100%) as a white solid. The crude product was used in the next step directly without further purification. MS obsd. (ESI⁺) [(M+H)⁺]: 326.9.

Step 4: Preparation of Methyl 1-(5-chloro-9-oxo-thioxanthen-3-yl)pyrrolidine-3-carboxylate

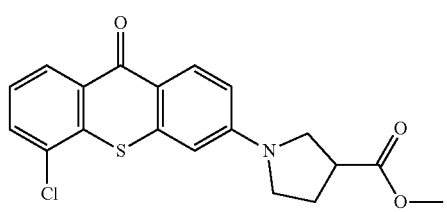

To a solution of 3-bromo-5-chloro-thioxanthen-9-one (50.0 mg, 0.154 mmol) in DMF (2.0 mL) was added methyl pyrrolidine-3-carboxylate (50.0 mg, 0.3 mmol) and Na$_2$CO$_3$ (163.0 mg, 1.54 mmol), then the mixture was stirred at 110° C. for 12 hours. The reaction mixture was then filtered and the filtrate was concentrated under reduced pressure to give the crude of methyl 1-(5-chloro-9-oxo-thioxanthen-3-yl)pyrrolidine-3-carboxylate (50.0 mg, 86.8%), which was used in the next step without further purification.

Step 5: Preparation of 1-(5-chloro-9-oxo-thioxanthen-3-yl)pyrrolidine-3-carboxylic acid

6

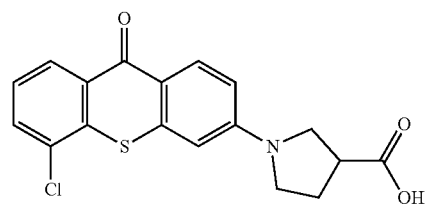

To a solution of methyl 1-(5-chloro-9-oxo-thioxanthen-3-yl)pyrrolidine-3-carboxylate (50.0 mg, 0.154 mmol) in H$_2$O (1.0 mL) and DMF (5.0 mL) was added NaOH (61.6 mg, 1.54 mmol) and the mixture was stirred at 25° C. for 12 hours. The mixture was poured into water (50 mL) and adjusted to pH=5-6 by addition of hydrochloric acid (2 mol/L). The resulting mixture was extracted with DCM (50 mL) three times. The combined organic layer was concentrated under reduced pressure. The residue was purified by column chromatography on silica gel (elution with DCM: MeOH=20:1) to give 1-(5-chloro-9-oxo-thioxanthen-3-yl)pyrrolidine-3-carboxylic acid (31.0 mg, 55.9%) as a yellow solid. $^1$H NMR (methanol-d$_4$, 400 MHz): δ ppm 8.39-8.51 (m, 1H), 8.30 (d, J=9.0 Hz, 1H), 7.73 (s, 1H), 7.46 (t, J=8.0 Hz, 1H), 6.81 (dd, J=9.2, 2.3 Hz, 1H), 6.69 (d, J=2.3 Hz, 1H), 3.67 (d, J=7.0 Hz, 2H), 3.43-3.61 (m, 2H), 3.34-3.38 (m, 1H), 2.27-2.44 (m, 2H). MS obsd. (ESI$^+$) [(M+H)$^+$]: 360.0.

Example 7: 1-(5-bromo-9-oxo-xanthen-3-yl)pyrrolidine-3-carboxylic acid

7

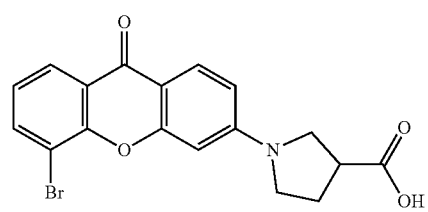

Example 7 was prepared according to Scheme 7.

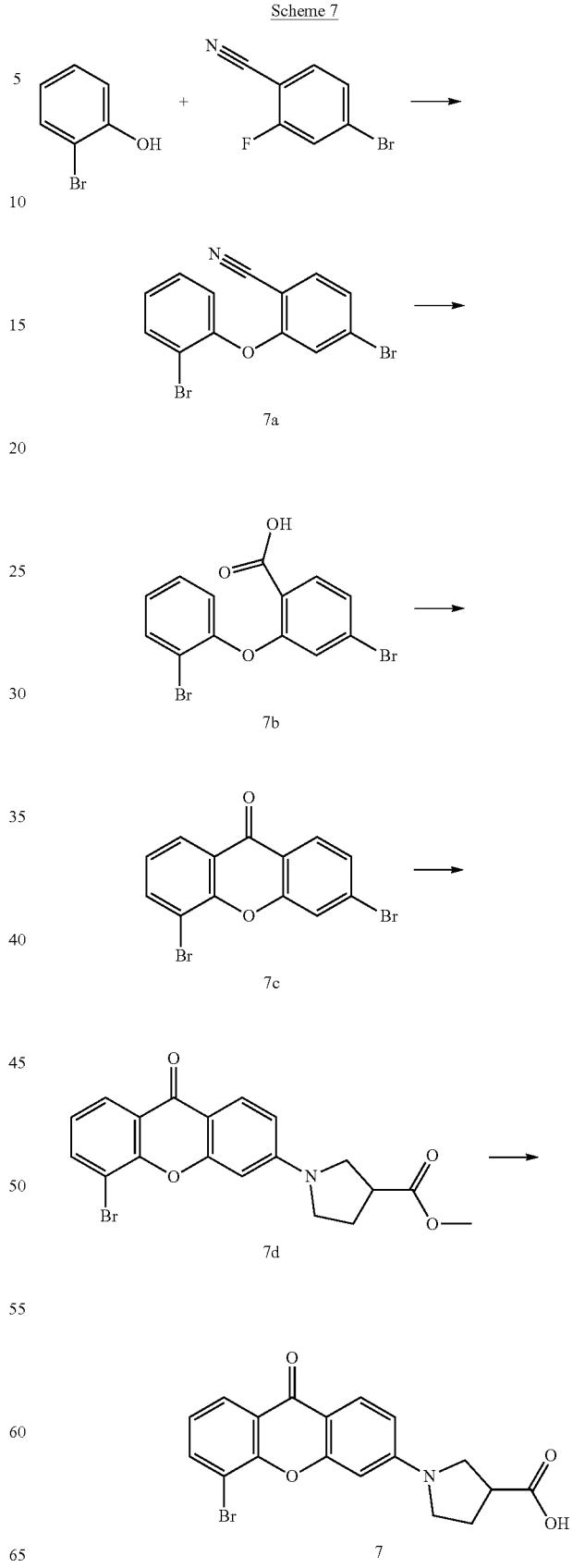

Step 1: Preparation of 4-bromo-2-(2-bromophenoxy)benzonitrile

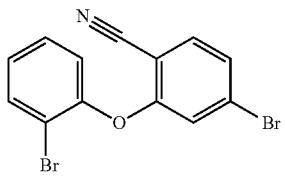

7a

To a mixture of 2-bromophenol (3.0 g, 15.08 mmol) and 4-bromo-2-fluoro-benzonitrile (2.85 g, 16.59 mmol) in DMF (40 mL) was added K$_2$CO$_3$ (4.17 g, 30.16 mmol) and Cu (5.8 g, 90.48 mmol) at 25° C. After being stirred at 60° C. for 16 hours, the resulting mixture was poured into water (50 mL) and extracted with EtOAc (100 mL) three times. The combined organic layer was dried over anhydrous Na$_2$SO$_4$ and concentrated under reduced pressure to give the crude of 4-bromo-2-(2-bromophenoxy)benzonitrile (4.2 g, 78.7%) as a yellow oil, which was used in the next step directly without further purification. MS obsd. (ESI$^+$) [(M+H)$^+$]: 353.9.

Step 2: Preparation of 4-bromo-2-(2-bromophenoxy)benzoic acid

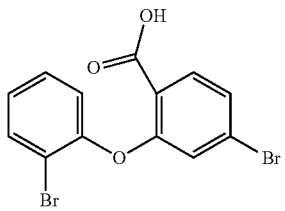

7b

To a mixture of 4-bromo-2-(2-bromophenoxy)benzonitrile (2.0 g, 5.7 mmol) in dioxane (15 mL) and H$_2$O (15 mL) was added NaOH (0.68 g, 17.1 mmol) at 25° C. After being stirred at 90° C. for 16 hours, the resulting mixture was poured into water (50 mL) and adjusted to pH=7 with conc. HCl and then extracted with EtOAc (100 mL) three times. The combined organic layer was dried over anhydrous Na$_2$SO$_4$ and concentrated under reduced pressure to give the crude of 4-bromo-2-(2-bromophenoxy)benzoic acid (1.5 g, 70.5%) as a brown oil, which was used in the next step directly without further purification. MS obsd. (ESI$^+$) [(M+H)$^+$]: 373.0.

Step 3: Preparation of 3,5-dibromoxanthen-9-one

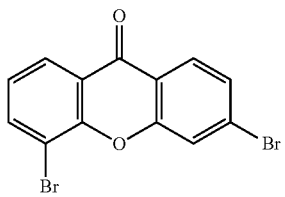

7c

A solution of 4-bromo-2-(2-bromophenoxy)benzoic acid (0.5 g, 1.352 mmol) in condensed sulfuric acid (10 mL) was stirred at 90° C. for 15 hours under N$_2$ atmosphere. The reaction mixture was poured into water (50 mL). The resulting mixture was extracted with EtOAc (60 mL) three times. The combined organic layer was dried over anhydrous Na$_2$SO$_4$ and concentrated under reduced pressure to afford the crude of 3,5-dibromoxanthen-9-one (0.4 g, 65.8%) as a yellow solid, which was used in the next step directly without further purification. MS obsd. (ESI$^+$) [(M+H)$^+$]: 354.1.

Step 4: Preparation of Methyl 1-(5-bromo-9-oxo-xanthen-3-yl)pyrrolidine-3-carboxylate

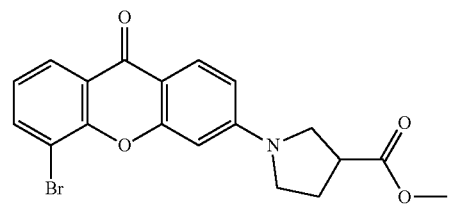

7d

To a mixture of 3,5-dibromoxanthen-9-one (0.2 g, 0.568 mmol) and methyl pyrrolidine-3-carboxylate (73.4 mg, 0.568 mmol) in DMF (3 mL) was added K$_2$CO$_3$ (0.12 g, 0.853 mmol) at 25° C. After being stirred at 90° C. for 16 hours, the resulting mixture was poured into water (50 mL) and extracted with EtOAc (300 mL). The organic phase was dried over anhydrous Na$_2$SO$_4$ and concentrated under reduced pressure to give the crude of methyl 1-(5-bromo-9-oxo-xanthen-3-yl)pyrrolidine-3-carboxylate (0.2 g, 87.5%) as a yellow solid, which was used in the next step without further purification. MS obsd. (ESI$^+$) [(M+H)$^+$]: 402.1.

Step 5: Preparation of 1-(5-bromo-9-oxo-xanthen-3-yl)pyrrolidine-3-carboxylic acid

7

To a mixture of methyl 1-(5-bromo-9-oxo-xanthen-3-yl)pyrrolidine-3-carboxylate (0.2 g, 0.499 mmol, crude, prepared above) in a mixed solvent of THF (3 mL) and H$_2$O (2 mL) was added LiOH.H$_2$O (62.9 mg, 1.496 mmol) at 25° C. and the mixture was then stirred at 25° C. for 16 hours. The resulting mixture was poured into water (50 mL) and adjusted to pH=5-6 by addition of hydrochloric acid (2 mol/L). The resulting mixture was extracted with EtOAc (300 mL). The organic phase washed with brine, dried over anhydrous Na$_2$SO$_4$ and concentrated under reduced pressure to give the crude of 1-(5-fluoro-9-oxo-xanthen-3-yl)pyrrolidine-3-carboxylic acid, which was recrystallized in EtOAc (20 mL) to give 1-(5-bromo-9-oxo-xanthen-3-yl)pyrrolidine-3-carboxylic acid (0.07 g, 36.0%) as a yellow solid. $^1$H NMR (DMSO-d$_6$, 400 MHz): δ ppm 8.12-8.06 (m, 2H), 7.96-7.94 (d, J=8.8 Hz, 1H), 7.36-7.32 (t, 1H), 6.78-6.75 (t, 1H), 6.50-6.50 (d, J=2.0 Hz, 1H), 3.66-3.61 (m, 2H), 3.50-3.47 (m, 2H), 3.27-3.25 (m, 1H), 2.29-2.20 (m, 2H). MS obsd. (ESI$^+$) [(M+H)$^+$]: 389.1.

Example 8: 2-[1-(5-chloro-9-oxo-xanthen-3-yl)pyrrolidin-3-yl]acetic Acid

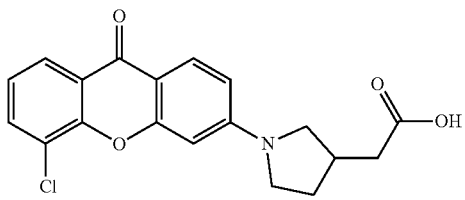

Example 8 was prepared in analogy to the procedure described for the preparation of Example 2 by using 2-pyrrolidin-3-ylacetic acid as the starting material instead of pyrrolidine-3-carboxylic acid in Step 1. $^1$H NMR (DMSO-d$_6$, 400 MHz): δ ppm 12.12-12.39 (m, 1H), 8.04-8.12 (m, 1H), 7.89-8.00 (m, 2H), 7.35-7.46 (m, 1H), 6.68-6.78 (m, 1H), 6.41-6.50 (m, 1H), 3.61-3.70 (m, 1H), 3.49-3.59 (m, 1H), 3.37-3.48 (m, 1H), 3.06-3.16 (m, 1H), 2.61-2.73 (m, 1H), 2.43-2.48 (m, 2H), 2.16-2.28 (m, 1H), 1.64-1.82 (m, 1H). MS obsd. (ESI$^+$) [(M+H)$^+$]: 358.0.

Example 9: 5-fluoro-3-(1-piperidyl)xanthen-9-one

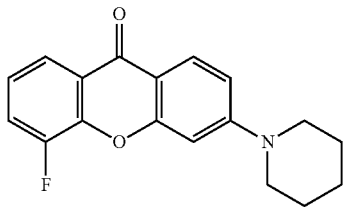 [SMILES: O=c1c2ccc(N3CCCCC3)cc2oc2c(F)cccc12]

Example 9 was prepared in analogy to the procedure described for the preparation of Example 1 by using 3-bromo-5-fluoro-xanthen-9-one (intermediate 3) and piperidine as the starting materials instead of 3-bromo-5-chloro-xanthen-9-one (intermediate 1) and pyrrolidine in Step 1. $^1$H NMR (DMSO-d$_6$, 400 MHz): δ ppm 7.86-8.03 (m, 2H), 7.75 (ddd, J=11.04, 8.03, 1.25 Hz, 1H), 7.39 (td, J=8.03, 4.52 Hz, 1H), 7.11 (dd, J=9.29, 2.26 Hz, 1H), 6.93 (d, J=2.26 Hz, 1H), 3.47-3.59 (m, 4H), 1.53-1.70 (m, 6H). MS obsd. (ESI$^+$) [(M+H)$^+$]: 298.1.

Example 10: 5-chloro-3-[3-(hydroxymethyl)pyrrolidin-1-yl]xanthen-9-one

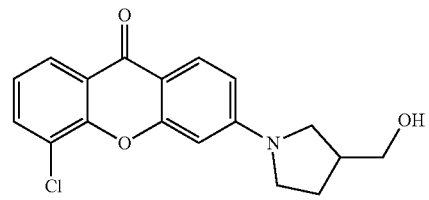

Example 10 was prepared in analogy to the procedure described for the preparation of Example 1 by using pyrrolidin-3-ylmethanol as the starting material instead of pyrrolidine in Step 1. $^1$H NMR (DMSO-d$_6$, 400 MHz): δ ppm 8.08 (dd, J=7.9, 1.6 Hz, 1H), 7.88-8.01 (m, 2H), 7.40 (t, J=7.8 Hz, 1H), 6.76 (dd, J=9.0, 2.3 Hz, 1H), 6.39-6.56 (m, 1H), 4.78 (t, J=5.3 Hz, 1H), 3.38-3.60 (m, 4H), 3.23 (dd, J=10.2, 6.7 Hz, 1H), 2.44-2.48 (m, 1H), 1.97-2.19 (m, 1H), 1.83 (br dd, J=12.2, 7.2 Hz, 1H). MS obsd. (ESI$^+$) [(M+H)$^+$]: 330.1.

Example 11: Methyl 1-(5-chloro-9-oxo-xanthen-3-yl)pyrrolidine-3-carboxylate

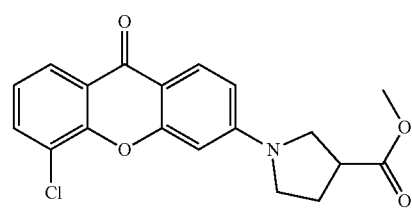

Example 11 was prepared in analogy to the procedure described for the preparation of Example 1 by using methyl pyrrolidine-3-carboxylate as the starting material instead of pyrrolidine in Step 1. $^1$H NMR (DMSO-d$_6$, 400 MHz): δ ppm 8.08 (dd, J=1.63, 7.91 Hz, 1H), 7.92-8.00 (m, 2H), 7.38-7.44 (m, 1H), 6.76-6.82 (m, 1H), 6.55 (d, J=2.26 Hz, 1H), 3.70-3.75 (m, 1H), 3.68 (s, 3H), 3.58-3.65 (m, 1H), 3.46-3.57 (m, 2H), 3.37-3.43 (m, 1H), 2.27-2.36 (m, 1H), 2.17-2.27 (m, 1H). MS obsd. (ESI$^+$) [(M+H)$^+$]: 358.1.

Example 12: 5-chloro-3-(3-hydroxy-1-piperidyl)xanthen-9-one

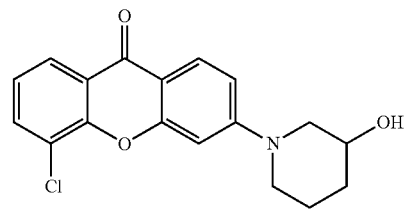

Example 12 was prepared in analogy to the procedure described for the preparation of Example 1 by using piperidin-3-ol as the starting material instead of pyrrolidine in Step 1. $^1$H NMR (DMSO-$d_6$, 400 MHz): δ ppm 8.08 (dd, J=8.0, 1.5 Hz, 1H), 7.87-7.99 (m, 2H), 7.41 (t, J=7.8 Hz, 1H), 7.09 (dd, J=9.2, 2.4 Hz, 1H), 6.86 (d, J=2.5 Hz, 1H), 4.93 (d, J=4.0 Hz, 1H), 3.70-3.95 (m, 2H), 3.60 (td, J=8.3, 4.0 Hz, 1H), 3.08-3.23 (m, 1H), 3.03 (dd, J=12.8, 8.5 Hz, 1H), 1.84-1.99 (m, 1H), 1.69-1.84 (m, 1H), 1.37-1.60 (m, 2H). MS obsd. (ESI$^+$) [(M+H)$^+$]: 330.1.

Example 13:
3-(azepan-1-yl)-5-fluoro-xanthen-9-one

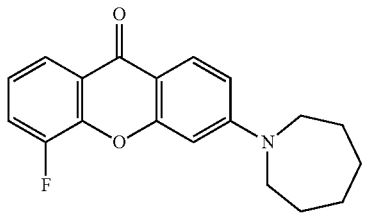

13

Example 13 was prepared in analogy to the procedure described for the preparation of Example 1 by using 3-bromo-5-fluoro-xanthen-9-one (intermediate 3) and azepane as the starting materials instead of 3-bromo-5-chloro-xanthen-9-one (intermediate 1) and pyrrolidine in Step 1. $^1$H NMR (DMSO-$d_6$, 400 MHz): δ ppm 8.02 (d, J=9.3 Hz, 1H), 7.97 (dt, J=8.0, 1.4 Hz, 1H), 7.55 (ddd, J=10.8, 8.0, 1.5 Hz, 1H), 7.27-7.37 (m, 1H), 6.90 (dd, J=9.2, 2.4 Hz, 1H), 6.67 (d, J=2.5 Hz, 1H), 3.57-3.71 (m, 3H), 3.33 (dt, J=3.3, 1.6 Hz, 3H), 1.87 (br s, 3H), 1.54-1.69 (m, 3H). MS obsd. (ESI$^+$) [(M+H)$^+$]: 312.1.

Example 14: 1-(5-chloro-9-oxo-xanthen-3-yl)piperidine-3-carboxylic acid

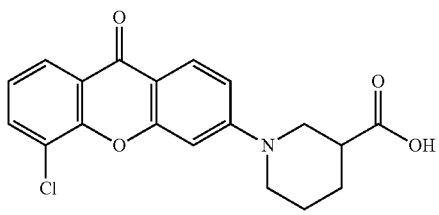

14

Example 14 was prepared in analogy to the procedure described for the preparation of Example 2 by using piperidine-3-carboxylic acid as the starting material instead of pyrrolidine-3-carboxylic acid in Step 1. $^1$H NMR (DMSO-$d_6$, 400 MHz): δ ppm 12.47 (s, 1H), 8.08 (dd, J=7.9, 1.6 Hz, 1H), 7.87-7.98 (m, 2H), 7.40 (t, J=7.9 Hz, 1H), 7.13 (dd, J=9.2, 2.4 Hz, 1H), 6.91 (d, J=2.3 Hz, 1H), 4.01 (dd, J=13.4, 3.4 Hz, 1H), 3.86 (br d, J=13.1 Hz, 1H), 3.25-3.41 (m, 1H), 3.09-3.24 (m, 1H), 2.53-2.61 (m, 1H), 1.91-2.04 (m, 1H), 1.67-1.80 (m, 2H), 1.46-1.63 (m, 1H). MS obsd. (ESI$^+$) [(M+H)$^+$]: 358.1.

Example 15: (3R,4S)-1-(5-chloro-9-oxo-xanthen-3-yl)-4-(4-fluorophenyl)pyrrolidine-3-carboxylic Acid

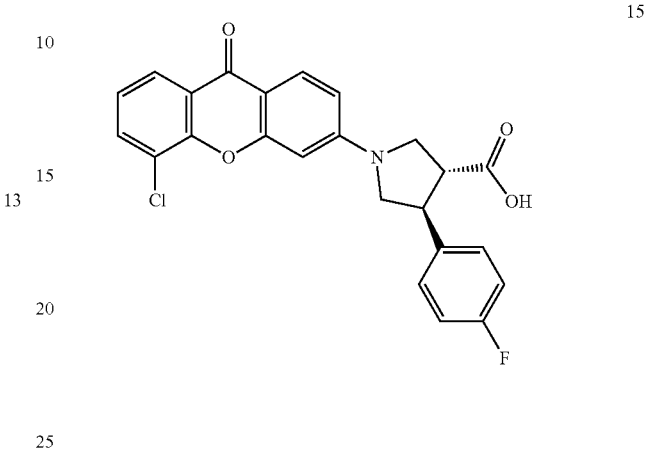

15

Example 15 was prepared in analogy to the procedure described for the preparation of Example 2 by using (3S, 4R)-4-(4-fluorophenyl)pyrrolidine-3-carboxylic acid (CAS #: 1047651-77-3) as the starting material instead of pyrrolidine-3-carboxylic acid in Step 1. $^1$H NMR (DMSO-$d_6$, 400 MHz): δ ppm 8.15 (br d, J=6.52 Hz, 1H), 8.09 (br d, J=8.78 Hz, 1H), 7.81-7.86 (m, 1H), 7.41-7.49 (m, 2H), 7.36 (s, 1H), 7.06-7.12 (m, 2H), 6.80-6.86 (m, 1H), 6.60-6.64 (m, 1H), 3.88-4.08 (m, 4H), 3.79 (m, 1H), 3.57 (m, 1H). MS obsd. (ESI$^+$) [(M+H)$^+$]: 438.0.

Example 16: 1-(5-chloro-9-oxo-xanthen-3-yl)-3-methyl-pyrrolidine-3-carboxylic Acid

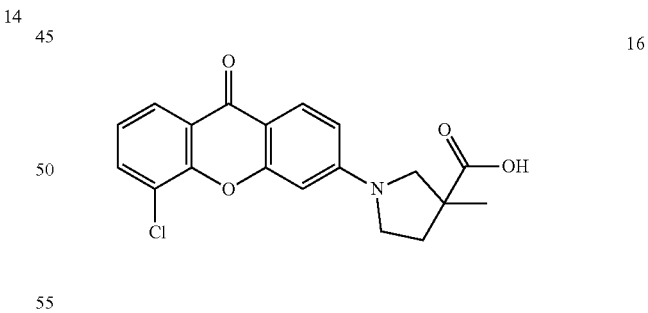

16

Example 16 was prepared in analogy to the procedure described for the preparation of Example 2 by using 3-methylpyrrolidine-3-carboxylic acid (CAS #: 885953-27-5) as the starting material instead of pyrrolidine-3-carboxylic acid in Step 1. $^1$H NMR (DMSO-$d_6$, 400 MHz): δ ppm 12.68 (br s, 1H), 8.08 (dd, J=7.9, 1.6 Hz, 1H), 7.80-8.01 (m, 2H), 7.41 (t, J=7.9 Hz, 1H), 6.77 (dd, J=8.9, 2.1 Hz, 1H), 6.53 (d, J=2.3 Hz, 1H), 3.85 (d, J=10.5 Hz, 1H), 3.37-3.69 (m, 3H), 2.36-2.48 (m, 1H), 1.86-2.05 (m, 1H), 1.36 (s, 3H). MS obsd. (ESI$^+$) [(M+H)$^+$]: 358.1.

Example 17: 1-(5-chloro-9-oxo-xanthen-3-yl)-4,4-dimethyl-pyrrolidine-3-carboxylic Acid

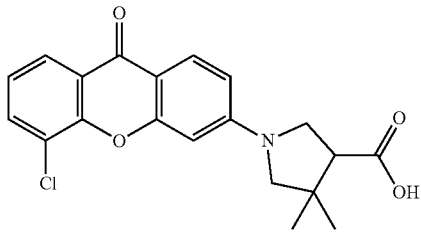

Example 17 was prepared in analogy to the procedure described for the preparation of Example 2 by using 4,4-dimethylpyrrolidine-3-carboxylic acid (CAS #: 261896-35-9) as the starting material instead of pyrrolidine-3-carboxylic acid in Step 1. $^1$H NMR (DMSO-d$_6$, 400 MHz): δ ppm 12.56-12.68 (m, 1H), 8.06-8.12 (m, 1H), 7.92-7.99 (m, 2H), 7.38-7.44 (m, 1H), 6.74-6.78 (m, 1H), 6.49-6.53 (m, 1H), 3.71 (d, J=8.03 Hz, 2H), 3.41 (d, J=10.04 Hz, 1H), 3.29 (s, 1H), 2.99 (t, J=8.03 Hz, 1H), 1.28 (s, 3H), 1.04 (s, 3H). MS obsd. (ESI$^+$) [(M+H)$^+$]: 372.0.

Example 18: (3R,4S)-1-(5-chloro-9-oxo-xanthen-3-yl)-4-(3-pyridyl)pyrrolidine-3-carboxylic Acid

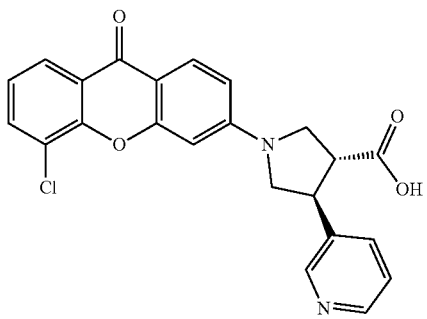

Example 18 was prepared in analogy to the procedure described for the preparation of Example 2 by using (3R,4S)-4-(3-pyridyl)pyrrolidine-3-carboxylic acid (CAS #: 1330830-30-2) as the starting material instead of pyrrolidine-3-carboxylic acid in Step 1. $^1$H NMR (DMSO-d$_6$, 400 MHz): δ ppm 8.78 (br s, 1H), 8.57-8.70 (m, 1H), 8.18 (br d, J=6.8 Hz, 1H), 8.09 (dd, J=8.0, 1.5 Hz, 1H), 7.89-8.02 (m, 2H), 7.67 (br s, 1H), 7.42 (t, J=7.9 Hz, 1H), 6.85 (br d, J=8.8 Hz, 1H), 6.64 (s, 1H), 3.96-4.12 (m, 2H), 3.84-3.95 (m, 1H), 3.74 (brt, J=9.4 Hz, 1H), 3.54-3.66 (m, 2H). MS obsd. (ESI$^+$) [(M+H)$^+$]: 421.1.

Example 19: 1-(5-chloro-9-oxo-xanthen-3-yl)-3-(trifluoromethyl)pyrrolidine-3-carboxylic Acid

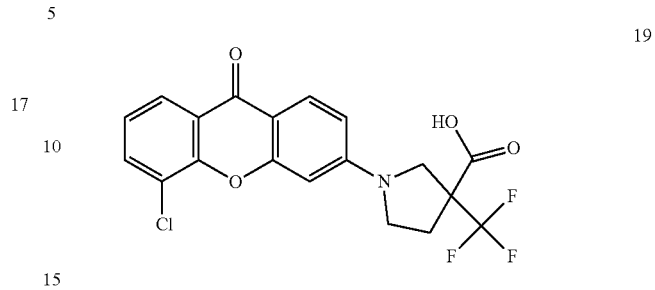

Example 19 was prepared in analogy to the procedure described for the preparation of Example 2 by using 3-(trifluoromethyl)pyrrolidine-3-carboxylic acid (CAS #: 916423-57-9) as the starting material instead of pyrrolidine-3-carboxylic acid in Step 1. $^1$H NMR (DMSO-d$_6$, 400 MHz): δ ppm 14.12 (br s, 1H), 8.07-8.17 (m, 1H), 7.99 (br d, J=9.03 Hz, 2H), 7.42 (s, 1H), 6.82-6.90 (m, 1H), 6.65-6.72 (m, 1H), 4.06-4.16 (m, 1H), 3.86 (m, 1H), 3.64-3.74 (m, 1H), 3.52-3.61 (m, 1H), 2.64-2.72 (m, 1H), 2.40-2.48 (m, 1H). MS obsd. (ESI$^+$) [(M+H)$^+$]: 412.0.

Example 20: (3S,4R)-1-(5-chloro-9-oxo-xanthen-3-yl)-4-(4-chlorophenyl)pyrrolidine-3-carboxylic Acid

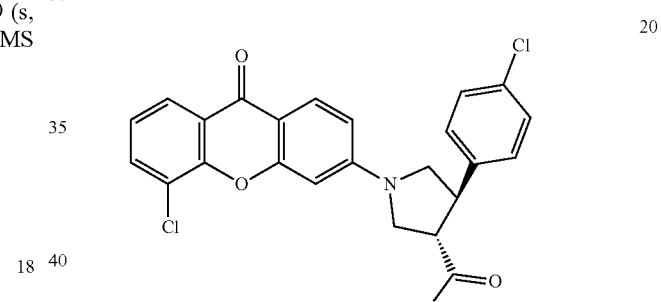

Example 20 was prepared in analogy to the procedure described for the preparation of Example 2 by using (3S,4R)-4-(4-chlorophenyl)pyrrolidine-3-carboxylic acid (CAS #: 1047651-82-0) as the starting material instead of pyrrolidine-3-carboxylic acid in Step 1. $^1$H NMR (DMSO-d$_6$, 400 MHz): δ ppm 12.73 (br s, 1H), 8.09 (dd, J=7.8, 1.5 Hz, 1H), 7.85-8.02 (m, 2H), 7.26-7.57 (m, 5H), 6.76-6.90 (m, 1H), 6.54-6.69 (m, 1H), 3.88-4.09 (m, 2H), 3.61-3.86 (m, 2H), 3.38-3.59 (m, 2H). MS obsd. (ESI$^+$) [(M+H)$^+$]: 455.1.

Example 21: 5-fluoro-3-pyrrolidin-1-yl-xanthen-9-one

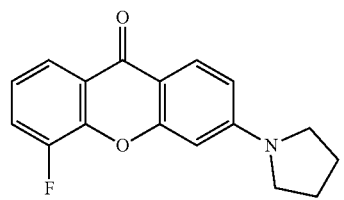

Example 21 was prepared in analogy to the procedure described for the preparation of Example 1 by using 3-bromo-5-fluoro-xanthen-9-one (intermediate 3) as the starting material instead of 3-bromo-5-chloro-xanthen-9-one (intermediate 1) in Step 1. $^1$H NMR (DMSO-$d_6$, 400 MHz): δ ppm 7.96 (d, J=9.03 Hz, 1H), 7.91 (d, J=8.03 Hz, 1H), 7.69-7.78 (m, 1H), 7.37 (td, J=7.91, 4.52 Hz, 1H), 6.75 (dd, J=9.03, 1.76 Hz, 1H), 6.55 (s, 1H), 3.42 (m., 4H), 2.01 (m, 4H). MS obsd. (ESI$^+$) [(M+H)$^+$]: 284.1.

Example 22:
1-chloro-4-fluoro-6-pyrrolidin-1-ylxanthen-9-one

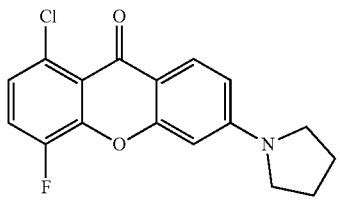

22

Example 22 was prepared in analogy to the procedure described for the preparation of Example 1 by using 6-bromo-1-chloro-4-fluoro-xanthen-9-one (intermediate 9) as the starting material instead of 3-bromo-5-chloro-xanthen-9-one (intermediate 1) in Step 1. $^1$H NMR (DMSO-$d_6$, 400 MHz): δ ppm 8.02-8.09 (m, 1H), 7.24 (s, 1H), 7.17 (br. s., 1H), 6.56 (dd, J=8.9, 2.2 Hz, 1H), 6.33 (d, J=1.9 Hz, 1H), 3.36 (t, J=6.4 Hz, 4H), 1.97-2.07 (m, 4H). MS obsd. (ESI$^+$) [(M+H)$^+$]: 318.1.

Example 23: 1-(5-fluoro-9-oxo-xanthen-3-yl)pyrrolidin-2-one

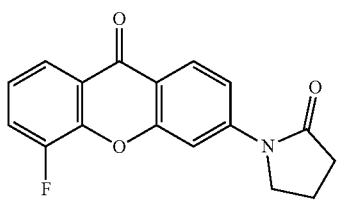

23

Example 23 was prepared in analogy to the procedure described for the preparation of Example 1 by using 3-bromo-5-fluoro-xanthen-9-one (intermediate 3) and pyrrolidin-2-one as the starting materials instead of 3-bromo-5-chloro-xanthen-9-one (intermediate 1) and pyrrolidine in Step 1. $^1$H NMR (DMSO-$d_6$, 400 MHz): δ ppm 8.18-8.16 (d, J=8.8 Hz, 1H), 8.00-7.96 (m, 2H), 7.87-7.80 (m, 2H), 7.47-7.44 (m, 1H), 3.98-3.95 (t, 2H), 2.63-2.59 (t, 2H), 2.14-2.10 (t, 2H) MS obsd. (ESI$^+$) [(M+H)$^+$]: 298.0.

Example 24:
5-fluoro-3-(3-hydroxypyrrolidin-1-yl)xanthen-9-one

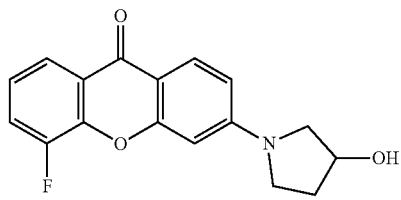

24

Example 24 was prepared in analogy to the procedure described for the preparation of Example 1 by using 3-bromo-5-fluoro-xanthen-9-one (intermediate 3) and pyrrolidin-3-ol as the starting materials instead of 3-bromo-5-chloro-xanthen-9-one (intermediate 1) and pyrrolidine in Step 1. $^1$H NMR (DMSO-$d_6$, 400 MHz): δ ppm 7.98-7.95 (d, J=9.2 Hz, 1H), 7.92-7.90 (d, J=8.4 Hz, 1H), 7.76-7.72 (t, 1H), 7.41-7.37 (m, 1H), 6.76-6.73 (t, 1H), 6.54 (s, 1H), 5.12-5.11 (d, J=4.0 Hz, 1H), 4.46 (s, 1H), 3.57-3.53 (m, 3H), 3.35-3.27 (m, 1H), 2.10-2.05 (m, 1H), 1.99-1.98 (m, 1H). MS obsd. (ESI$^+$) [(M+H)$^+$]: 300.1.

Example 25:
5-fluoro-2-methyl-3-pyrrolidin-1-yl-xanthen-9-one

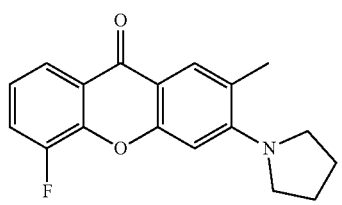

25

Example 25 was prepared in analogy to the procedure described for the preparation of Example 1 by using 3-bromo-5-fluoro-2-methyl-xanthen-9-one (intermediate 2) as the starting material instead of 3-bromo-5-chloro-xanthen-9-one (intermediate 1) in Step 1. $^1$H NMR (DMSO-$d_6$, 400 MHz): δ ppm 8.09 (td, J=1.3, 8.0 Hz, 1H), 7.97 (s, 1H), 7.44 (ddd, J=1.6, 8.0, 10.6 Hz, 1H), 7.28-7.23 (m, 1H), 6.68 (s, 1H), 3.58-3.52 (t, J=8.0 Hz, 4H), 2.52 (s, 3H), 2.05-2.02 (m, 4H). MS obsd. (ESI$^+$) [(M+H)$^+$]: 298.1.

Example 26: 1-(5,8-dichloro-9-oxo-xanthen-3-yl)pyrrolidine-3-carboxylic Acid

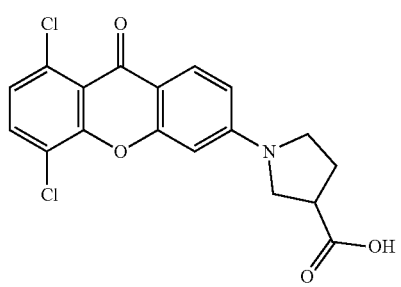

26

Example 26 was prepared in analogy to the procedure described for the preparation of Example 5 by using 6-bromo-1,4-dichloro-xanthen-9-one (intermediate 10) as the starting material instead of 3-bromo-5-fluoro-xanthen-9-one (intermediate 3) in Step 1. $^1$H NMR (DMSO-d$_6$, 400 MHz): δ ppm 14.54-11.04 (m, 1H), 7.93-7.81 (m, 2H), 7.46-7.35 (m, 1H), 6.77-6.68 (m, 1H), 6.42 (s, 1H), 3.72-3.53 (m, 2H), 3.52-3.43 (m, 2H), 3.30-3.20 (m, 1H), 2.38-2.13 (m, 2H). MS obsd. (ESI$^+$) [(M+H)$^+$]: 378.1.

Example 27: 5-chloro-3-[(3S)-3-hydroxypyrrolidin-1-yl]xanthen-9-one

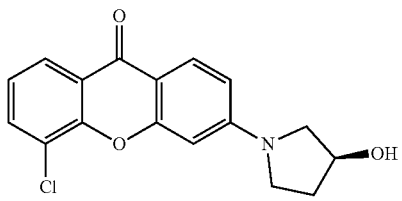

27

Example 27 was prepared in analogy to the procedure described for the preparation of Example 1 by using (3S)-pyrrolidin-3-ol as the starting material instead of pyrrolidine in Step 1. $^1$H NMR (DMSO-d$_6$, 400 MHz): δ ppm 8.09-8.07 (d, J=7.6 Hz, 1H), 7.97-7.93 (t, 2H), 7.42-7.38 (t, 1H), 6.77-6.74 (d, J=8.8 Hz, 1H), 6.49 (s, 1H). 5.11-5.10 (d, J=3.6 Hz, 1H), 4.47 (s, 1H), 3.58-3.49 (m, 3H), 3.31-3.28 (m, 1H), 2.10-1.99 (m, 2H). MS obsd. (ESI$^+$) [(M+H)$^+$]: 316.1.

Example 28: 2,5-difluoro-3-pyrrolidin-1-yl-xanthen-9-one

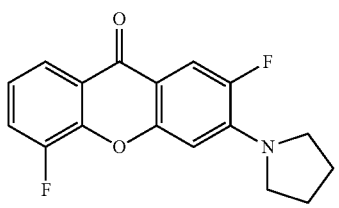

28

Example 28 was prepared in analogy to the procedure described for the preparation of Example 1 by using 3-bromo-2,5-difluoro-xanthen-9-one (intermediate 16) as the starting material instead of 3-bromo-5-chloro-xanthen-9-one (intermediate 1) in Step 1. $^1$H NMR (DMSO-d$_6$, 400 MHz): δ ppm 7.95 (d, J=8.0 Hz, 1H), 7.65 (d, J=14 Hz, 1H), 7.36-7.31 (m, 1H), 7.19-7.14 (m, 1H), 6.41 (d, J=7.0 Hz, 1H), 3.51-3.47 (m, 4H), 1.94 (t, J=6.5 Hz, 4H). MS obsd. (ESI$^+$) [(M+H)$^+$]: 302.1.

Example 29: 5-fluoro-3-morpholino-xanthen-9-one

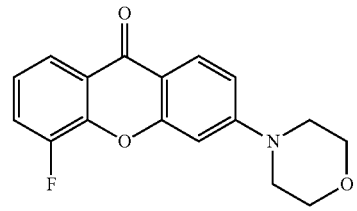

29

Example 29 was prepared in analogy to the procedure described for the preparation of Example 1 by using 3-bromo-5-fluoro-xanthen-9-one (intermediate 3) and morpholine as the starting materials instead of 3-bromo-5-chloro-xanthen-9-one (intermediate 1) and pyrrolidine in Step 1. $^1$H NMR (DMSO-d$_6$, 400 MHz): δ ppm 7.31 (d, J=9.29 Hz, 1H), 7.21 (d, J=8.03 Hz, 1H), 6.75-6.86 (m, 1H), 6.57 (td, J=7.91, 4.52 Hz, 1H), 6.33 (dd, J=9.16, 2.13 Hz, 1H), 6.19 (d, J=2.01 Hz, 1H), 3.01-3.12 (m, 4H), 2.64-2.74 (m, 4H). MS obsd. (ESI$^+$) [(M+H)$^+$]: 300.0.

Example 30: 5-chloro-3-[(3R)-3-hydroxypyrrolidin-1-yl]xanthen-9-one

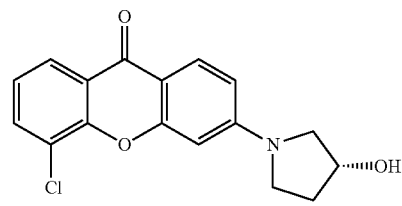

30

Example 30 was prepared in analogy to the procedure described for the preparation of Example 1 by using (3R)-pyrrolidin-3-ol as the starting material instead of pyrrolidine in Step 1. $^1$H NMR (DMSO-d$_6$, 400 MHz): δ ppm 8.09-8.07 (m, 1H), 7.98-7.93 (m, 2H), 7.43-7.39 (t, 1H), 6.77-6.75 (m, 1H), 6.50-6.49 (d, J=2.0 Hz, 1H), 5.11-5.10 (d, J=3.6 Hz, 1H), 4.46 (s, 1H), 3.57-3.49 (m, 3H), 3.31-3.28 (m, 1H), 2.14-1.99 (m, 2H). MS obsd. (ESI$^+$) [(M+H)$^+$]: 316.1.

Example 31: 5-fluoro-3-[(3S)-3-hydroxypyrrolidin-1-yl]xanthen-9-one

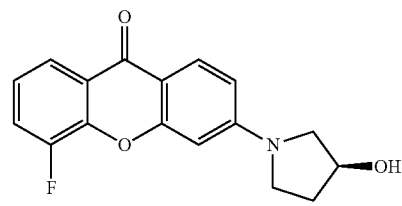

31

Example 31 was prepared in analogy to the procedure described for the preparation of Example 1 by using 3-bromo-5-fluoro-xanthen-9-one (intermediate 3) and (3S)-pyrrolidin-3-ol as the starting materials instead of 3-bromo- 5-chloro-xanthen-9-one (intermediate 1) and pyrrolidine in Step 1. ¹H NMR (DMSO-d₆, 400 MHz): δ ppm 7.98-7.95 (d, J=9.2 Hz, 1H), 7.92-7.90 (d, J=8.4 Hz, 1H), 7.76-7.72 (m, 1H), 7.40-7.37 (m, 1H), 6.75-6.73 (t, 1H), 6.54 (s, 1H), 5.12-5.11 (d, J=4.0 Hz, 1H), 4.46 (s, 1H), 3.57-3.53 (m, 3H), 3.35-3.27 (m, 1H), 2.10-2.05 (m, 1H), 1.99-1.98 (m, 1H). MS obsd. (ESI⁺) [(M+H)⁺]: 300.1.

Example 32: 5-fluoro-3-[(3R)-3-hydroxypyrrolidin-1-yl]xanthen-9-one

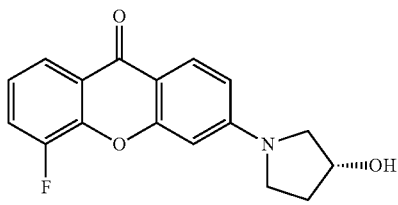

32

Example 32 was prepared in analogy to the procedure described for the preparation of Example 1 by using 3-bromo-5-fluoro-xanthen-9-one (intermediate 3) and (3R)-pyrrolidin-3-ol as the starting materials instead of 3-bromo-5-chloro-xanthen-9-one (intermediate 1) and pyrrolidine in Step 1. ¹H NMR (DMSO-d₆, 400 MHz): δ ppm 7.98-7.95 (d, J=9.2 Hz, 1H), 7.92-7.90 (d, J=8.0 Hz, 1H), 7.76-7.71 (m, 1H), 7.40-7.37 (m, 1H), 6.76-6.74 (d, J=9.2 Hz, 1H), 6.54 (s, 1H), 5.11-5.10 (d, J=5.2 Hz, 1H), 4.46 (s, 1H), 3.57-3.53 (m, 3H), 3.34-3.27 (m, 1H), 2.10-2.06 (m, 1H), 1.99-1.98 (m, 1H). MS obsd. (ESI⁺) [(M+H)⁺]: 300.1.

Example 33: 5-fluoro-3-(3-methoxypyrrolidin-1-yl)xanthen-9-one

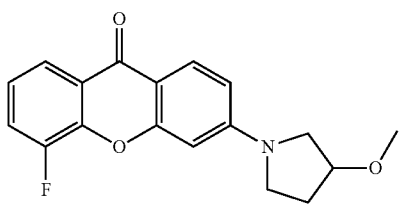

33

Example 33 was prepared in analogy to the procedure described for the preparation of Example 1 by using 3-bromo-5-fluoro-xanthen-9-one (intermediate 3) and 3-methoxypyrrolidine as the starting materials instead of 3-bromo-5-chloro-xanthen-9-one (intermediate 1) and pyrrolidine in Step 1. ¹H NMR (DMSO-d₆, 400 MHz): δ ppm 7.98-7.95 (d, J=9.2 Hz, 1H), 7.92-7.90 (d, J=8.0 Hz, 1H), 7.76-7.71 (m, 1H), 7.40-7.37 (m, 1H), 6.76-6.74 (d, J=9.2 Hz, 1H), 6.54 (s, 1H), 4.45 (s, 1H), 3.56-3.52 (m, 3H), 3.40 (s, 3H), 3.34-3.27 (m, 1H), 2.10-2.06 (m, 1H), 1.99-1.98 (m, 1H). MS obsd. (ESI⁺) [(M+H)⁺]: 314.1.

Example 34: 5-fluoro-3-[3-(4-pyridyl)pyrrolidin-1-yl]xanthen-9-one

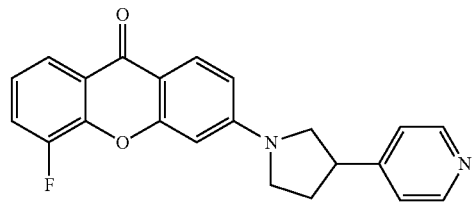

34

Example 34 was prepared in analogy to the procedure described for the preparation of Example 1 by using 3-bromo-5-fluoro-xanthen-9-one (intermediate 3) and 4-pyrrolidin-3-ylpyridine (CAS #: 150281-47-3) as the starting materials instead of 3-bromo-5-chloro-xanthen-9-one (intermediate 1) and pyrrolidine in Step 1. ¹H NMR (DMSO-d₆, 400 MHz): δ ppm 8.74-8.95 (m, 2H), 8.05-8.20 (m, 3H), 7.95-8.02 (m, 1H), 7.54-7.64 (m, 1H), 7.31-7.40 (m, 1H), 6.78-6.89 (m, 1H), 6.65 (br. s., 1H), 3.94-4.14 (m, 2H), 3.63-3.82 (m, 3H), 2.65-2.77 (m, 1H), 2.27-2.44 (m, 1H). MS obsd. (ESI⁺) [(M+H)⁺]: 361.2.

Example 35: 2-chloro-4-fluoro-6-pyrrolidin-1-yl-xanthen-9-one

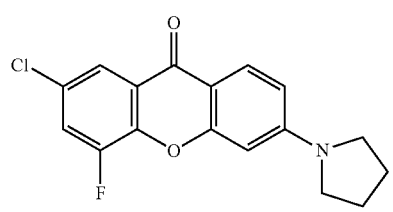

35

Example 35 was prepared in analogy to the procedure described for the preparation of Example 1 by using 6-bromo-2-chloro-4-fluoro-xanthen-9-one (intermediate 6) as the starting material instead of 3-bromo-5-chloro-xanthen-9-one (intermediate 1) in Step 1. ¹H NMR (DMSO-d₆, 400 MHz): δ ppm 8.12 (d, J=9.03 Hz, 1H), 8.01-8.06 (m, 1H), 7.41 (dd, J=9.91, 2.38 Hz, 1H), 6.63 (dd, J=9.03, 2.26 Hz, 1H), 6.43 (d, J=2.01 Hz, 1H), 3.43 (t, J=6.40 Hz, 4H), 2.01-2.18 (m, 4H). MS obsd. (ESI⁺) [(M+H)⁺]: 318.1.

Example 36: 1-(5-chloro-9-oxo-xanthen-3-yl)pyrrolidine-2-carboxylic Acid

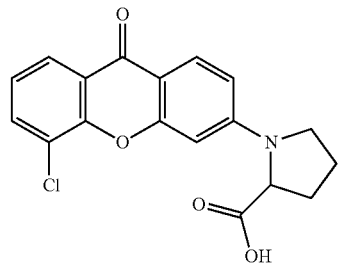

36

Example 36 was prepared in analogy to the procedure described for the preparation of Example 5 by using methyl pyrrolidine-2-carboxylate as the starting material instead of methyl pyrrolidine-3-carboxylate in Step 1. $^1$H NMR (DMSO-$d_6$, 400 MHz): δ ppm 8.04-8.11 (m, 1H), 7.90-8.01 (m, 2H), 7.36-7.45 (m, 1H), 6.64-6.79 (m, 1H), 6.33-6.56 (m, 1H), 4.39-4.54 (m, 1H), 3.56-3.65 (m, 1H), 3.46-3.53 (m, 1H), 2.27-2.38 (m, 1H), 2.08 (m., 3H). MS obsd. (ESI$^+$) [(M+H)$^+$]: 343.9.

Example 37: 1-[9-oxo-5-(trifluoromethyl)xanthen-3-yl]pyrrolidine-3-carboxylic Acid

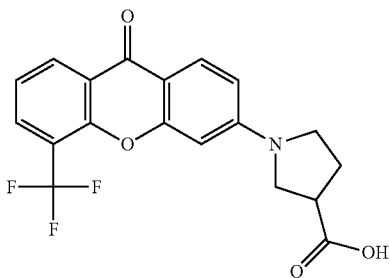

37

Example 37 was prepared in analogy to the procedure described for the preparation of Example 5 by using 3-bromo-5-(trifluoromethyl)xanthen-9-one (intermediate 7) as the starting material instead of 3-bromo-5-fluoro-xanthen-9-one (intermediate 3) in Step 1. $^1$H NMR (DMSO-$d_6$, 400 MHz): δ ppm 8.52 (d, J=7.8 Hz, 1H), 8.16 (d, J=9.0 Hz, 1H), 7.94 (d, J=7.5 Hz, 1H), 7.40 (t, J=7.7 Hz, 1H), 6.65 (dd, J=2.0, 9.0 Hz, 1H), 6.45 (d, J=2.0 Hz, 1H), 3.56-3.76 (m, 2H), 3.42-3.56 (m, 2H), 3.22-3.31 (m, 1H), 2.12-2.40 (m, 2H). MS obsd. (ESI$^+$) [(M+H)$^+$]: 378.1.

Example 38: 5-fluoro-3-(4-methylpiperazin-1-yl)xanthen-9-one

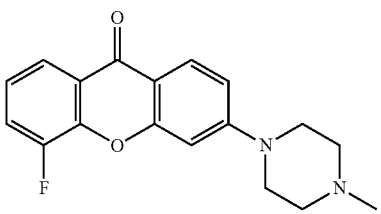

38

Example 34 was prepared in analogy to the procedure described for the preparation of Example 1 by using 3-bromo-5-fluoro-xanthen-9-one (intermediate 3) and 1-methylpiperazine as the starting materials instead of 3-bromo-5-chloro-xanthen-9-one (intermediate 1) and pyrrolidine in Step 1. $^1$H NMR (DMSO-$d_6$, 400 MHz): δ ppm 7.86-8.05 (m, 2H), 7.73 (t, J=8.85 Hz, 1H), 7.38 (m, 1H), 7.11 (d, J=8.29 Hz, 1H), 6.94 (br. s., 1H), 3.46 (m, 4H), 2.43 (m, 4H), 2.22 (br. s., 3H). MS obsd. (ESI$^+$) [(M+H)$^+$]: 313.1.

Example 39: 1-(5-chloro-2-methyl-9-oxo-xanthen-3-yl)pyrrolidine-3-carboxylic Acid

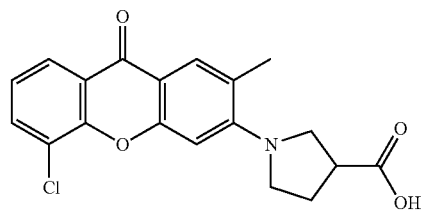

39

Example 39 was prepared in analogy to the procedure described for the preparation of Example 5 by using 3-bromo-5-chloro-2-methyl-xanthen-9-one (intermediate 4) as the starting material instead of 3-bromo-5-fluoro-xanthen-9-one (intermediate 3) in Step 1. $^1$H NMR (DMSO-$d_6$, 400 MHz): δ ppm 8.05-8.10 (m, 1H), 7.94 (d, J=7.5 Hz, 1H), 7.78 (s, 1H), 7.40 (t, J=7.9 Hz, 1H), 6.64 (s, 1H), 3.67-3.77 (m, 2H), 3.52-3.60 (m, 2H), 3.10 (td, J=6.0, 2.0 Hz, 1H), 2.48 (br. s., 3H), 2.10-2.21 (m, 2H). MS obsd. (ESI$^+$) [(M+H)$^+$]: 358.0.

Example 40: 1-(5-chloro-8-methyl-9-oxo-xanthen-3-yl)pyrrolidine-3-carboxylic Acid

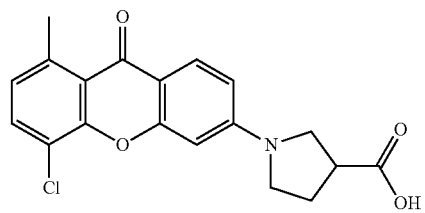

40

Example 40 was prepared in analogy to the procedure described for the preparation of Example 5 by using 6-bromo-4-chloro-1-methyl-xanthen-9-one (intermediate 11) as the starting material instead of 3-bromo-5-fluoro-xanthen-9-one (intermediate 3) in Step 1. $^1$H NMR (DMSO-$d_6$, 400 MHz): δ ppm 12.61 (s, 1H), 7.90-7.88 (d, J=8.8 Hz, 1H), 7.76-7.74 (d, J=8.0 Hz, 1H), 7.14-7.12 (d, J=8.0 Hz, 1H), 6.72-6.70 (d, J=8.4 Hz, 1H), 6.42 (s, 1H), 3.63-3.58 (m, 2H), 3.47-3.43 (m, 2H), 3.36-3.29 (m, 1H), 2.79 (s, 3H), 2.28-2.20 (m, 2H). MS obsd. (ESI$^+$) [(M+H)$^+$]: 358.2.

Example 41: 1-(6-chloro-10-oxo-chromeno[3,2-c]pyridin-3-yl)pyrrolidine-3-carboxylic Acid

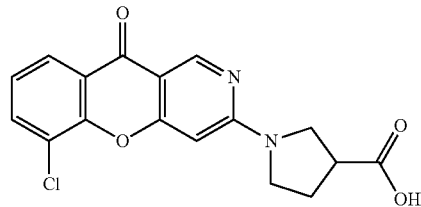

41

Example 41 was prepared in analogy to the procedure described for the preparation of Example 5 by using 3,6-dichlorochromeno[3,2-c]pyridin-10-one (intermediate 12) as the starting material instead of 3-bromo-5-fluoro-xanthen-9-one (intermediate 3) in Step 1. ¹H NMR (DMSO-d₆, 400 MHz): δ ppm 12.58 (br. s., 1H), 8.88 (s, 1H), 8.05 (d, J=7.8 Hz, 1H), 7.95 (d, J=7.5 Hz, 1H), 7.41 (t, J=7.8 Hz, 1H), 6.39 (s, 1H), 3.52-3.86 (m, 4H), 3.14-3.27 (m, 1H), 2.06-2.36 (m, 2H). MS obsd. (ESI⁺) [(M+H)⁺]: 345.2.

Example 42: 1-(5-chloro-2-fluoro-9-oxo-xanthen-3-yl)pyrrolidine-3-carboxylic Acid

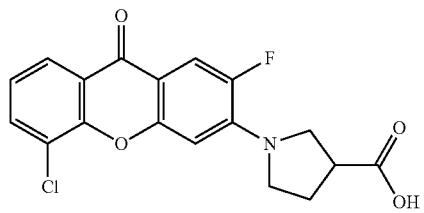

42

Example 42 was prepared in analogy to the procedure described for the preparation of Example 5 by using 3-bromo-5-chloro-2-fluoro-xanthen-9-one (intermediate 13) as the starting material instead of 3-bromo-5-fluoro-xanthen-9-one (intermediate 3) in Step 1. ¹H NMR (DMSO-d₆, 400 MHz): δ ppm 8.12-8.10 (d, J=8.0 Hz, 1H), 8.02-7.99 (d, J=8.0 Hz, 1H), 7.71-7.68 (d, J=6.8 Hz, 1H), 7.45-7.49 (m, 1H), 6.71-6.68 (d, J=6.8 Hz, 1H), 3.83-3.82 (m, 2H), 3.67-3.66 (m, 2H), 3.21-3.19 (m, 1H), 2.26-2.22 (m, 2H). MS obsd. (ESI⁺) [(M+H)⁺]: 362.0.

Example 43: 1-(2,5-dichloro-9-oxo-xanthen-3-yl)pyrrolidine-3-carboxylic Acid

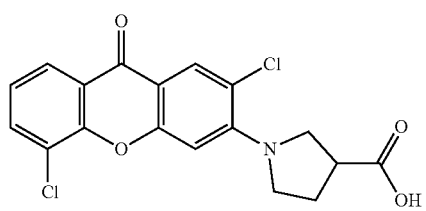

43

Example 43 was prepared in analogy to the procedure described for the preparation of Example 5 by using 3-bromo-2,5-dichloro-xanthen-9-one (intermediate 14) as the starting material instead of 3-bromo-5-fluoro-xanthen-9-one (intermediate 3) in Step 1. ¹H NMR (DMSO-d₆, 400 MHz): δ ppm 7.70-8.10 (m, 3H), 7.33 (m, 1H), 6.60 (m, 1H), 3.80-3.91 (m, J=5.0 Hz, 1H), 3.68-3.77 (m, J=8.3 Hz, 1H), 3.61 (d, J=4.5 Hz, 2H), 2.89 (m, 1H), 1.99-2.24 (m, 2H). MS obsd. (ESI⁺) [(M+H)⁺]: 378.0.

Example 44: 1-(5-chloro-8-cyano-9-oxo-xanthen-3-yl)pyrrolidine-3-carboxylic Acid

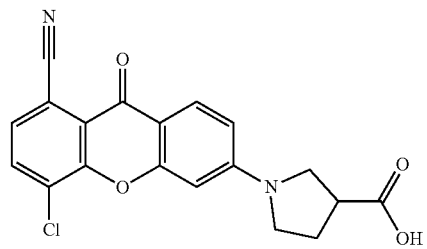

44

Example 44 was prepared in analogy to the procedure described for the preparation of Example 5 by using 6-bromo-4-chloro-9-oxo-xanthene-1-carbonitrile (intermediate 15) as the starting material instead of 3-bromo-5-fluoro-xanthen-9-one (intermediate 3) in Step 1. ¹H NMR (DMSO-d₆, 400 MHz): δ ppm 8.10-8.05 (m, 1H), 7.94-7.85 (m, 2H), 6.81-6.77 (m, 1H), 6.50-6.48 (d, J=9.6 Hz, 1H), 3.64-3.59 (m, 2H), 3.50-3.46 (m, 2H), 3.35-3.27 (m, 1H), 2.33-2.19 (m, 2H). MS obsd. (ESI⁺) [(M+H)⁺]: 369.0.

Example 45: 6-fluoro-3-pyrrolidin-1-yl-chromeno[3,2-c]pyridin-10-one

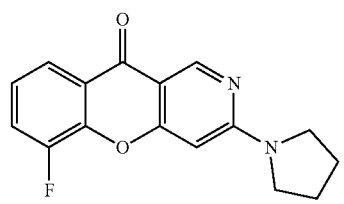

45

Example 45 was prepared in analogy to the procedure described for the preparation of Example 1 by using 2-chloro-9-fluoro-chromeno[2,3-b]pyridin-5-one (intermediate 17) as the starting material instead of 3-bromo-5-chloro-xanthen-9-one (intermediate 1) in Step 1. ¹H NMR (DMSO-d₆, 400 MHz): δ ppm 8.90 (s, 1H), 7.91-7.89 (d, J=8.0 Hz, 1H), 7.80-7.75 (m, 1H), 7.43-7.39 (m, 1H), 6.44 (s, 1H), 3.59 (m, 4H), 1.99 (m, 4H). MS obsd. (ESI⁺) [(M+H)⁺]: 285.1.

Example 46: 1-(5-chloro-9-oxo-xanthen-3-yl)-N,N-dimethyl-pyrrolidine-3-carboxamide

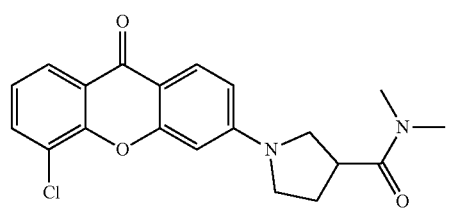

46

To a solution of 1-(5-chloro-9-oxo-xanthen-3-yl)pyrrolidine-3-carboxylic acid (Example 3, 50 mg, 0.145 mmol) in DMF (5 mL) was added dimethylamine hydrochloride (17.8 mg, 218 µmol), HATU (83 mg, 0.218 mmol) and N,N-diisopropylethylamine (56.4 mg, 0.465 mmol) at 25° C. Then the mixture was stirred at room temperature for 1 hour. The resulting mixture was poured into water (30 mL) and extracted with EtOAc (50 mL) for three times. The combined organic phase was washed with brine, dried over anhydrous $Na_2SO_4$, and concentrated under reduced pressure. The residue was purified by preparative HPLC to give 1-(5-chloro-9-oxo-xanthen-3-yl)-N,N-dimethyl-pyrrolidine-3-carboxamide as a solid (28.0 mg, 51.9%). $^1$H NMR (DMSO-$d_6$, 400 MHz): δ ppm 8.08 (dd, J=8.0, 1.5 Hz, 1H), 7.87-8.02 (m, 2H), 7.41 (t, J=7.9 Hz, 1H), 6.78 (dd, J=9.0, 2.3 Hz, 1H), 6.53 (d, J=2.0 Hz, 1H), 3.45-3.74 (m, 5H), 3.11 (s, 3H), 2.87 (s, 3H), 2.20-2.32 (m, 1H), 2.01-2.17 (m, 1H). MS obsd. (ESI$^+$) [(M+H)$^+$]: 371.1.

Example 47: 3-(2,6-diazaspiro[3.4]octan-6-yl)-5-fluoro-xanthen-9-one

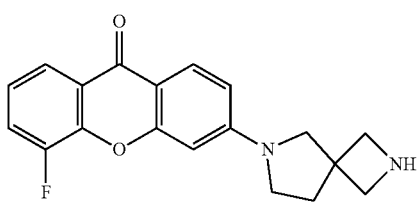

47

Step 1: Preparation of Tert-Butyl 7-(5-fluoro-9-oxo-xanthen-3-yl)-2,7-diazaspiro[3.4]octane-2-carboxylate

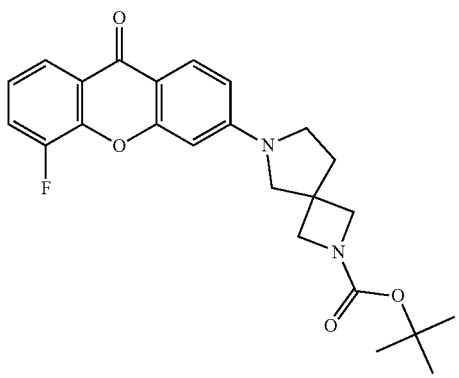

47a

To a mixture of 3-bromo-5-fluoro-xanthen-9-one (0.1 g, 0.341 mmol) in NMP (2 mL) was added tert-butyl 2,6-diazaspiro[3.4]octane-2-carboxylate (86.9 mg, 0.341 mmol, vendor: PharmaBlock (Nanjing) R&D Co. Ltd, CAS #: 885270-84-8, Cat. #: as PB00717) and $K_3PO_4$ (0.145 g, 0.682 mmol) at 25° C. Then the mixture was stirred at 90° C. for 16 hours. The resulting mixture was poured into water (30 mL) and extracted with EtOAc (50 mL) three times. The combined organic layer was washed with brine, dried over anhydrous $Na_2SO_4$, and concentrated under reduced pressure. The residue was purified by column chromatography on silica gel (elution with PE:EtOAc=20:1 to 1:1) to give tert-butyl 7-(5-fluoro-9-oxo-xanthen-3-yl)-2,7-diazaspiro[3.4]octane-2-carboxylate (50.0 mg, 34.5%), MS obsd. (ESI$^+$) [(M+H)$^+$]: 425.1.

Step 2: Preparation of 3-(2,6-diazaspiro[3.4]octan-6-yl)-5-fluoro-xanthen-9-one

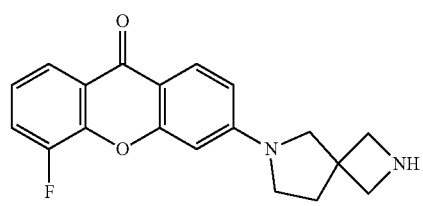

47

Tert-butyl 7-(5-fluoro-9-oxo-xanthen-3-yl)-2,7-diazaspiro[3.4]octane-2-carboxylate (50 mg, 118 µmol) was dissolved in TFA/DCM (1:1) (5 mL) at 0° C. The reaction mixture was warmed to room temperature and stirred for 1 hour. The resulting mixture was concentrated under reduced pressure. The residue was purified by preparative HPLC to give 3-(2,6-diazaspiro[3.4]octan-6-yl)-5-fluoro-xanthen-9-one (20 mg, 39%) as a solid. $^1$H NMR (DMSO-$d_6$, 400 MHz): δ ppm 8.35 (br s, 1H), 7.98 (d, J=8.8 Hz, 1H), 7.87-7.94 (m, 1H), 7.75 (ddd, J=11.0, 8.0, 1.5 Hz, 1H), 7.39 (td, J=8.0, 4.5 Hz, 1H), 6.57 (dd, J=8.8, 2.0 Hz, 1H), 6.46 (d, J=2.0 Hz, 1H), 3.92-4.13 (m, 4H), 3.06 (br t, J=6.9 Hz, 2H), 3.01-3.12 (m, 2H), 2.13 (br t, J=7.0 Hz, 2H). MS obsd. (ESI$^+$) [(M+H)$^+$]: 325.1.

Example 48: 3-(2,7-diazaspiro[4.4]nonan-2-yl)-5-fluoro-xanthen-9-one

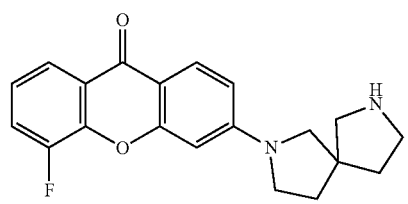

48

Step 1: Preparation of Tert-Butyl 7-(5-fluoro-9-oxo-xanthen-3-yl)-2,7-diazaspiro[4.4]nonane-2-carboxylate

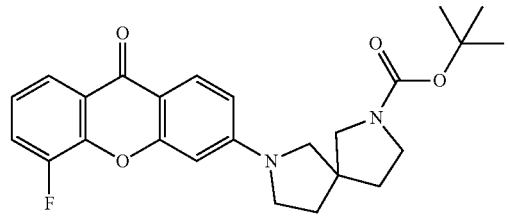

48a

To a mixture of 3-bromo-5-fluoro-xanthen-9-one (0.1 g, 0.341 mmol) in NMP (2 mL) was added tert-butyl 2,7-diazaspiro[4.4]nonane-2-carboxylate (116 mg, 0.512 mmol, vendor: Accela ChemBio Inc., CAS #: 236406-49-8, Cat. #: as SY009380) and K₃PO₄ (0.145 g, 0.682 mmol) at 25° C. Then the mixture was stirred at 90° C. for 16 hours. The resulting mixture was poured into water (30 mL) and extracted with EtOAc (50 mL) three times. The combined organic phase was washed with brine, dried over anhydrous Na₂SO₄, and concentrated under reduced pressure. The residue was purified by column chromatography on silica gel (elution with: PE:EtOAc=20:1 to 1:1) to give tert-butyl 7-(5-fluoro-9-oxo-xanthen-3-yl)-2,7-diazaspiro[4.4]nonane-2-carboxylate (55.0 mg, 36.8%), MS obsd. (ESI⁺) [(M+H)⁺]: 439.1.

Step 2: Preparation of 3-(2,7-diazaspiro[4.4]nonan-2-yl)-5-fluoro-xanthen-9-one

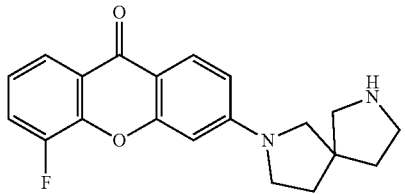

48

Tert-butyl 7-(5-fluoro-9-oxo-xanthen-3-yl)-2,7-diazaspiro[4.4]nonane-2-carboxylate (50.0 mg, 0.114 μmol) was dissolved in TFA/DCM (1:1) (5 mL) at 0° C. The reaction mixture was warmed to room temperature and stirred at room temperature for 1 hour. The resulting mixture was concentrated under reduced pressure The residue was purified by preparative HPLC to give 3-(2,7-diazaspiro[4.4]nonan-2-yl)-5-fluoro-xanthen-9-one (27 mg, 52%) as a solid. ¹H NMR (DMSO-d₆, 400 MHz): δ ppm 8.35 (s, 1H), 7.99 (d, J=8.8 Hz, 1H), 7.92 (d, J=8.0 Hz, 1H), 7.75 (ddd, J=11.0, 8.0, 1.5 Hz, 1H), 7.39 (td, J=8.0, 4.6 Hz, 1H), 6.73 (dd, J=9.0, 2.3 Hz, 1H), 6.54 (d, J=2.0 Hz, 1H), 3.44-3.57 (m, 4H), 3.35-3.43 (m, 2H), 3.16 (br t, J=7.2 Hz, 2H), 1.97-2.13 (m, 2H), 1.83-1.93 ppm (m, 2H). MS obsd. (ESI⁺) [(M+H)⁺]: 338.9.

Example 49: 3-(1,4-diazepan-1-yl)-5-fluoro-xanthen-9-one

49

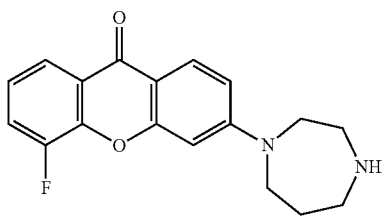

Step 1: Preparation of Tert-Butyl 4-(5-fluoro-9-oxo-xanthen-3-yl)-1,4-diazepane-1-carboxylate 49a

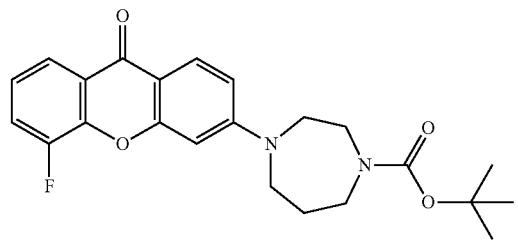

To a mixture of 3-bromo-5-fluoro-xanthen-9-one (0.1 g, 0.341 mmol) in NMP (2 mL) was added tert-butyl 1,4-diazepane-1-carboxylate (0.137 g, 0.682 mmol, vendor Accela ChemBio Inc., CAS #: 112275-50-0, Cat.#: as SY004264) and K₃PO₄ (0.145 g, 0.682 mmol) at 25° C. Then the mixture was stirred at 90° C. for 16 hours. The resulting mixture was poured into water (30 mL) and extracted with EtOAc (50 mL) for three times. The combined organic phase was washed with brine, dried over anhydrous Na₂SO₄, and concentrated under reduced pressure. The residue was purified by column chromatography on silica gel (elution with PE:EtOAc=20:1 to 1:1) to give tert-butyl 4-(5-fluoro-9-oxo-xanthen-3-yl)-1,4-diazepane-1-carboxylate (141.0 mg, 100%), MS obsd. (ESI⁺) [(M+H)⁺]: 413.0.

Step 2: Preparation of 3-(1,4-diazepan-1-yl)-5-fluoro-xanthen-9-one

49

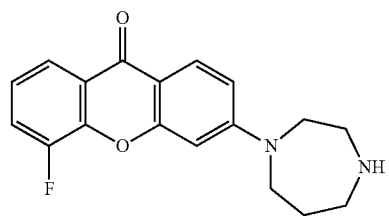

Tert-butyl 4-(5-fluoro-9-oxo-xanthen-3-yl)-1,4-diazepane-1-carboxylate (141.0 mg, 0.342 mmol) was dissolved in TFA/DCM (1:1) (5 mL) at 0° C. The reaction mixture was warmed to room temperature and stirred for 1 hour, the resulting mixture was concentrated under reduced pressure. The residue was purified by preparative HPLC to give 3-(1,4-diazepan-1-yl)-5-fluoro-xanthen-9-one (9 mg, 6.2%) as a solid. ¹H NMR (DMSO-d₆, 400 MHz): δ ppm 8.73 (br s, 1H), 8.02 (d, J=9.0 Hz, 1H), 7.94 (d, J=8.0 Hz, 1H), 7.78 (ddd, J=11.1, 8.1, 1.4 Hz, 1H), 7.41 (td, J=8.0, 4.5 Hz, 1H), 7.04 (dd, J=9.2, 2.4 Hz, 1H), 6.93 (d, J=2.3 Hz, 1H), 3.85-3.93 (m, 2H), 3.70 (t, J=6.0 Hz, 2H), 3.18 (br s, 2H), 2.53 (br d, J=1.8 Hz, 2H), 2.05-2.15 ppm (m, 2H). MS obsd. (ESI⁺) [(M+H)⁺]: 312.9.

Example 50: 3-[(3S)-3-aminopyrrolidin-1-yl]-5-fluoro-xanthen-9-one

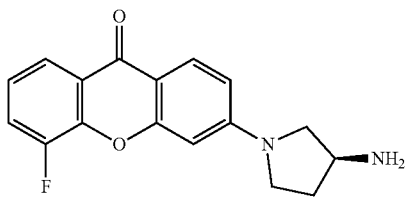

Step 1: Preparation of Tert-Butyl N-[(3S)-1-(5-fluoro-9-oxo-xanthen-3-yl)pyrrolidin-3-yl]carbamate

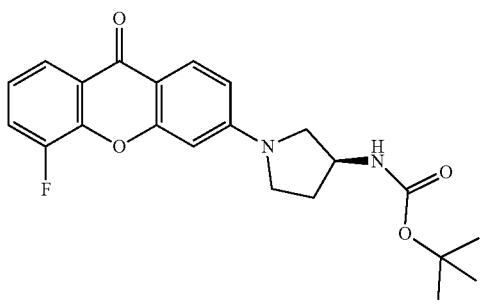

To a mixture of 3-bromo-5-fluoro-xanthen-9-one (0.1 g, 0.342 mmol) in NMP (2 mL) was added K$_3$PO$_4$ (108.9 mg, 0.514 mmol) and tert-butyl N-[(3S)-pyrrolidin-3-yl]carbamate (95.6 mg, 0.514 mmol) at 25° C., After being stirred at 90° C. for 16 hours, the resulting mixture was poured into water (50 mL) and extracted with EtOAc (200 mL). The organic phase was dried over anhydrous Na$_2$SO$_4$ and concentrated under reduced pressure. The residue was purified by column chromatography on silica gel (elution with PE:EtOAc=20:1 to 1:1) to give the tert-butyl N-[(3S)-1-(5-fluoro-9-oxo-xanthen-3-yl)pyrrolidin-3-yl]carbamate (0.09 g, 66.2%) as a yellow solid, MS obsd. (ESI$^+$) [(M+H)$^+$]: 399.2.

Step 2: Preparation of 3-[(3S)-3-aminopyrrolidin-1-yl]-5-fluoro-xanthen-9-one

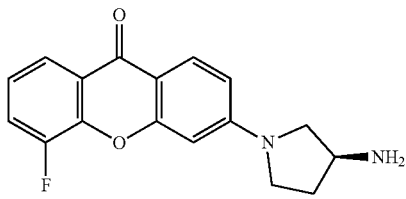

A solution of tert-butyl N-[(3S)-1-(5-fluoro-9-oxo-xanthen-3-yl)pyrrolidin-3-yl]carbamate (0.09 g, 0.226 mmol) in hydrogen chloride solution (4M in EtOAc, 3.0 mL) was stirred at 25° C. for 16 hours. Then resulted suspension was filtered and the solid was washed with EtOAc (10 mL) twice. The solid was then collected to give 3-[(3S)-3-aminopyrrolidin-1-yl]-5-fluoro-xanthen-9-one (35.0 mg, 46.1%) as a yellow solid. $^1$H NMR (DMSO-d$_6$, 400 MHz): δ ppm 8.45 (s, 2H), 8.02-7.99 (d, J=8.8 Hz, 1H), 7.93-7.91 (d, J=8.0 Hz, 1H), 7.78-7.73 (t, 1H), 7.41-7.39 (t, 1H), 6.79-6.76 (m, 1H), 6.61-6.61 (d, J=2.0 Hz, 1H), 4.01 (s, 1H), 3.74-3.71 (m, 1H), 3.66-3.64 (m, 1H), 3.55-3.52 (m, 2H), 2.38-2.35 (m, 1H), 2.21-2.18 (m, 1H). MS obsd. (ESI$^+$) [(M+H)$^+$]: 299.2.

Example 51: 3-[(3R)-3-aminopyrrolidin-1-yl]-5-fluoro-xanthen-9-one

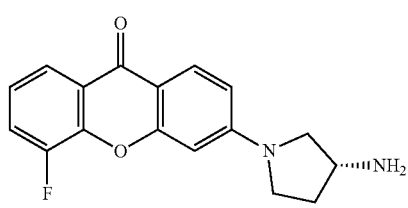

Step 1: Preparation of Tert-Butyl N-[(3R)-1-(5-fluoro-9-oxo-xanthen-3-yl)pyrrolidin-3-yl]carbamate

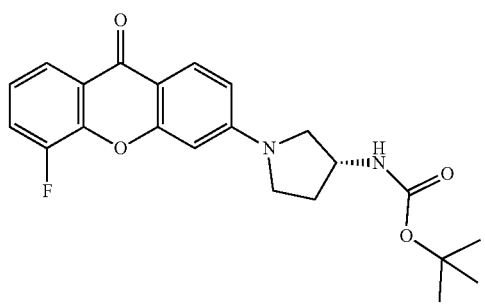

To a mixture of 3-bromo-5-fluoro-xanthen-9-one (300.0 mg, 1.02 mmol) in NMP (10 mL) was added K$_3$PO$_4$ (326.0 mg, 1.54 mmol) and tert-butyl N-[(3R)-pyrrolidin-3-yl]carbamate (229.0 mg, 1.23 mmol) at 25° C. Then the mixture was stirred at 100° C. for 16 hours. The resulting mixture was poured into water (20 mL) and extracted with EtOAc (40 mL) three times. The combined organic phase was dried over anhydrous Na$_2$SO$_4$ and concentrated under reduced pressure. The residue was purified by column chromatography on silica gel (elution with PE:EtOAc=1:1) to afford tert-butyl N-[(3R)-1-(5-fluoro-9-oxo-xanthen-3-yl)pyrrolidin-3-yl]carbamate (282.0 mg, 69.15%) as a yellow solid. MS obsd. (ESI$^+$) [(M+H)$^+$]: 399.2.

Step 2: Preparation of 3-[(3R)-3-aminopyrrolidin-1-yl]-5-fluoro-xanthen-9-one

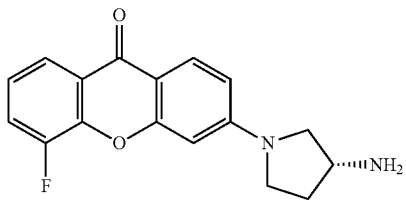

51

To a solution of tert-butyl N-[(3R)-1-(5-fluoro-9-oxo-xanthen-3-yl)pyrrolidin-3-yl]carbamate (270.0 mg, 0.678 mmol) in DCM (15.0 mL) was added hydrogen chloride solution (4M in EtOAc, 4 mL) dropwise at 0° C. After being stirred at 20° C. for 15 hours, the reaction mixture was concentrated under reduce pressure to afford 3-[(3R)-3-aminopyrrolidin-1-yl]-5-fluoro-xanthen-9-one (45.0 mg, 19.8%) as a brown solid. $^1$H NMR (DMSO-$d_6$, 400 MHz): δ ppm 8.11 (d, J=9.2 Hz, 1H), 8.01 (d, J=8.0 Hz, 1H), 7.64-7.59 (m, 1H), 7.35 (dt, J=4.4, 8.0 Hz, 1H), 6.84 (dd, J=2.3, 9.0 Hz, 1H), 6.66 (d, J=2.1 Hz, 1H), 4.15 (br. s., 1H), 3.85 (dd, J=6.2, 11.5 Hz, 1H), 3.87-3.73 (m, 1H), 3.63-3.59 (m, 2H), 2.60-2.55 (m, 1H), 2.28 (tdd, J=4.2, 8.4, 13.0 Hz, 1H). MS obsd. (ESI$^+$) [(M+H)$^+$]: 299.0.

Example 52: 1-(5'-fluorospiro[tetrahydrofuran-2,9'-xanthene]-3'-yl)pyrrolidine

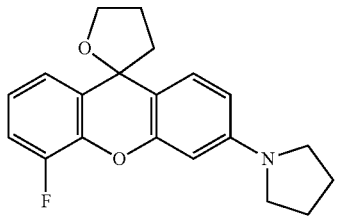

52

To a cooled solution of 3-chloropropan-1-ol (80.1 mg, 0.85 mmol) in anhydrous THF (5 mL) was added isopropylmagnesium chloride solution (0.5 M in THF, 0.8 mL, 0.4 mmol) dropwise at −30° C. After the addition was complete, the reaction mixture was stirred at −30° C. for 30 mins. Then the resulting mixture was added dropwise into a cooled solution of 5-fluoro-3-pyrrolidin-1-yl-xanthen-9-one (120 mg, 0.4 μmol) in THF at −30° C. After the addition was complete, the resulting mixture was stirred at room temperature for 2 hours, then diluted with a saturated NH$_4$Cl solution (15 mL) and extracted by EtOAc (20 mL) three times. The combined organic layer was washed with brine, dried over anhydrous Na$_2$SO$_4$, and concentrated under reduce pressure. The residue was purified by preparative HPLC to give 1-(5'-fluorospiro[tetrahydrofuran-2,9'-xanthene]-3'-yl)pyrrolidine (2.0 mg, 1.2%) as a white solid. $^1$H NMR (CD$_3$Cl, 400 MHz): δ ppm 8.09 (br d, J=9.3 Hz, 1H), 7.98-8.06 (m, 1H), 7.18-7.26 (m, 1H), 6.91 (br d, J=9.0 Hz, 1H), 6.65 (br dd, J=8.9, 2.4 Hz, 1H), 6.50 (br d, J=2.3 Hz, 1H), 3.76 (br t, J=6.5 Hz, 2H), 3.37-3.51 (m, 2H), 1.94-2.17 (m, 5H), 1.31-1.40 ppm (m, 5H). MS obsd. (ESI$^+$) [(M+H)$^+$]: 325.9.

Example 53: 1-(5-chloro-8-hydroxy-9-oxo-xanthen-3-yl)pyrrolidine-3-carboxylic Acid

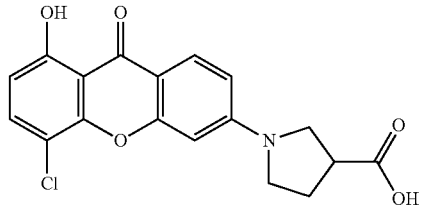

53

Example 53 was prepared according to Scheme 8.

Scheme 8

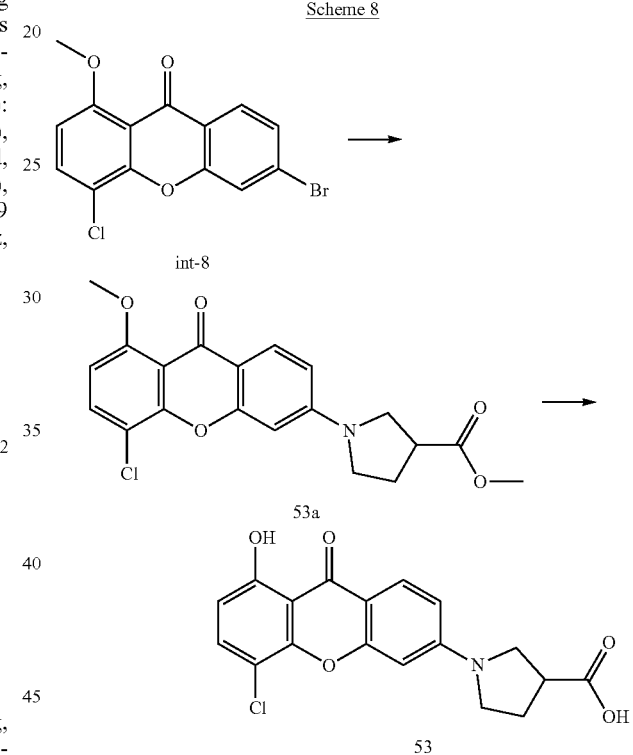

Step 1: Preparation of Methyl 1-(5-chloro-8-methoxy-9-oxo-xanthen-3-yl)pyrrolidine-3-carboxylate

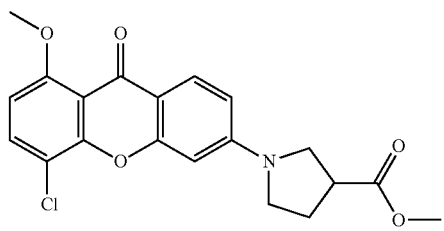

53a

To a mixture of 6-bromo-4-chloro-1-methoxy-xanthen-9-one (0.3 g, 0.915 mmol) in DMSO (8.0 mL) was added methyl pyrrolidine-3-carboxylate (0.23 g, 1.372 mmol) and DBU (0.34 g, 1.732 mmol) at 25° C. Then the mixture was stirred at 90° C. for 16 hours. The resulting solution was poured into water (100 mL) and extracted with EtOAc (150 mL) three times. The organic phase was dried over anhydrous Na$_2$SO$_4$ and concentrated under reduced pressure to give the crude of methyl 1-(5-chloro-8-methoxy-9-oxo-xanthen-3-yl)pyrrolidine-3-carboxylate (0.35 g, 15% purity) as a light yellow solid which was used in the next step without further purification. MS obsd. (ESI$^+$) [(M+H)$^+$]: 388.1.

Step 2: Preparation of 1-(5-chloro-8-hydroxy-9-oxo-xanthen-3-yl)pyrrolidine-3-carboxylic Acid

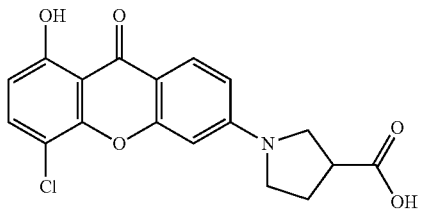

53

To a mixture of methyl 1-(5-chloro-8-methoxy-9-oxo-xanthen-3-yl)pyrrolidine-3-carboxylate (0.23 g, crude, prepared above) and DCM (8 mL) was added BBr$_3$ (0.74 g, 2.95 mmol) at room temperature and the mixture was then stirred at room temperature for 16 hours. The mixture was then concentrated under reduced pressure and the residue was purified by preparative HPLC to give 1-(5-chloro-8-hydroxy-9-oxo-xanthen-3-yl)pyrrolidine-3-carboxylic acid (0.07 g, 21.5% over 2 steps) as a yellow solid. $^1$H NMR (DMSO-d$_6$, 400 MHz): δ 13.239 (s, 1H), 7.927-7.904 (d, J=9.2 Hz, 1H), 7.754-7.732 (d, J=8.8 Hz, 1H), 6.786-6.748 (m, 2H), 6.488 (s, 1H), 3.659-3.609 (m, 2H), 3.501-3.485 (m, 2H), 3.274-3.257 (m, 1H), 2.269-2.211 (m, 2H). MS obsd. (ESI$^+$) [(M+H)$^+$]: 360.1.

Example 54:
1-(5-chloro-9-methyl-9H-xanthen-3-yl)pyrrolidine

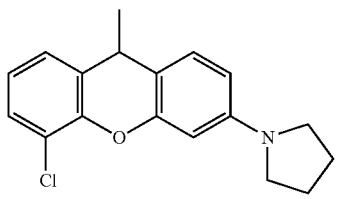

54

Step 1: Preparation of 1-(5-chloro-9-methylene-xanthen-3-yl)pyrrolidine

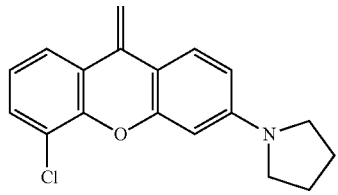

54a

To a cooled solution of 5-chloro-3-pyrrolidin-1-yl-xanthen-9-one (460 mg, 1.53 mmol) in THF (3 mL) was added methyllithium (1M in hexane, 1.84 mL, 1.84 mmol) dropwise at −78° C. After the addition was complete, the reaction mixture was warmed to room temperature and stirred for 3 hours. The reaction was then quenched by NH$_4$Cl solution (3 mL) and the resulting mixture was extracted by EtOAc (10 mL) three times. The combined organic layer was concentrated under reduced pressure to give a crude product of 1-(5-chloro-9-methylene-xanthen-3-yl)pyrrolidine (300 mg, 65.6%), which was used in the next step without further purification. MS obsd. (ESI$^+$) [(M+H)$^+$]: 298.1

Step 2: Preparation of 1-(5-chloro-9-methyl-9H-xanthen-3-yl)pyrrolidine

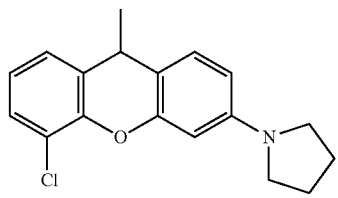

54

To a solution of 1-(5-chloro-9-methylene-xanthen-3-yl)pyrrolidine (120 mg, 403 μmol) in EtOAc (5 mL) was added Pd/C (20 mg). The resulting mixture was hydrogenated under H$_2$ atmosphere at room temperature overnight. After the reaction was complete, the mixture was filtered through silica gel pad and the filtrate was concentrated under reduced pressure. The residue was purified by preparative HPLC to give 1-(5-chloro-9-methyl-9H-xanthen-3-yl)pyrrolidine (5 mg, 4%) as a white solid. $^1$H NMR (DMSO-d$_6$, 400 MHz): δ ppm 7.37 (dd, J=8.0, 1.3 Hz, 1H), 7.31 (d, J=7.5 Hz, 1H), 7.14 (d, J=8.3 Hz, 1H), 7.04-7.11 (m, 1H), 6.38 (dd, J=8.4, 2.4 Hz, 1H), 6.22 (d, J=2.5 Hz, 1H), 4.07 (q, J=6.9 Hz, 1H), 3.24 (br t, J=6.7 Hz, 4H), 1.90-1.99 (m, 4H), 1.36 ppm (d, J=7.0 Hz, 3H). MS obsd. (ESI$^+$) [(M+H)$^+$]: 300.0.

Example 55: 1-(5-chloro-9H-xanthen-3-yl)pyrrolidine

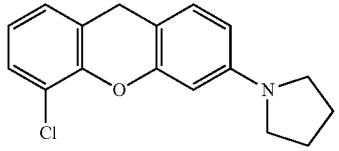

To a solution of 5-chloro-3-pyrrolidin-1-yl-xanthen-9-one (800 mg, 2.67 mmol) in THF (10 mL) was added BH$_3$.Me$_2$S (2M in THF, 10.7 mL, 21.4 mmol), the mixture was then stirred at 60° C. for 12 hours. After the reaction was complete, the mixture was then concentrated under reduced pressure and the residue was purified by column chromatography on silica gel (elution with PE:EtOAc=10:1 to 1:2) to give 1-(5-chloro-9H-xanthen-3-yl)pyrrolidine (650 mg, 81%) as a white solid. 1H NMR (400 MHz, CDCl3): δ ppm 7.23-7.28 (m, 1H), 6.89-7.11 (m, 3H), 6.30-6.43 (m, 2H), 3.93-4.03 (m, 2H), 3.31 (s, 4H), 1.97-2.08 (m, 4H). MS obsd. (ESI$^+$) [(M+H)$^+$]: 287.4.

Example 56: 1-(2,4,5-trichloro-9H-xanthen-3-yl)pyrrolidine

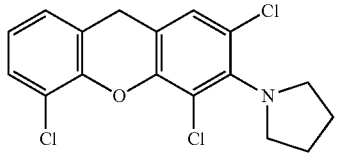

To a solution of 1-(5-chloro-9H-xanthen-3-yl)pyrrolidine (20 mg, 70 μmol) in DCM (3 mL) was added NCS (27.9 mg, 210 μmol). After being stirred at room temperature for 2 hours, the resulting mixture was concentrated under reduced pressure and the residue was purified by column chromatography on silica gel (elution with PE:EtOAc=10:1 to 1:2) to give 1-(2,4,5-trichloro-9H-xanthen-3-yl)pyrrolidine (15 mg, 60.4%) as a solid. $^1$H NMR (400 MHz, CDCl$_3$): δ ppm 7.30-7.34 (m, 1H), 7.14 (m, 1H), 7.07-7.11 (m, 1H), 7.01 (s, 1H), 4.04 (s, 2H), 3.35 (t, J=6.40 Hz, 4H), 2.00-2.06 (m, 4H). MS obsd. (ESI$^+$) [(M+H)$^+$]: 356.2.

Example 57: 1-[5-chloro-9-(oxetan-3-yl)-9H-xanthen-3-yl]pyrrolidine

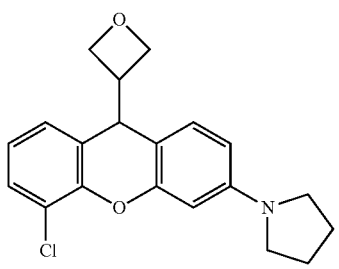

To a solution of 1-(5-chloro-9H-xanthen-3-yl)pyrrolidine (70 mg, 245 μmol) and NaH (60% in mineral oil) (100 mg, 2.5 mmol) in a mixed solvent of THF (2 mL) and DMSO (2 mL) was added 3-bromooxetane (268 mg, 1.96 mmol), the mixture was then stirred at 65° C. for 48 hours. The reaction was quenched with a saturated aqueous NaCl solution (20 mL) and the resulting mixture was extracted by EtOAc (30 mL) three times. The combined organic layer was concentrated under reduced pressure and the residue was purified by preparative HPLC to give 1-[5-chloro-9-(oxetan-3-yl)-9H-xanthen-3-yl]pyrrolidine (8.4 mg, 9.3%) as a white solid. $^1$H NMR (400 MHz, CDCl$_3$): δ ppm 7.32 (d, J=8.03 Hz, 1H), 7.12 (d, J=7.53 Hz, 1H), 7.06 (d, J=8.28 Hz, 1H), 6.99 (s, 1H), 6.45 (s, 1H), 6.33-6.39 (m, 1H), 4.63-4.71 (m, 2H), 4.54 (q, J=7.53 Hz, 2H), 4.10 (d, J=9.03 Hz, 1H), 3.27-3.36 (m, 4H), 3.17 (dd, J=7.53, 15.81 Hz, 1H), 2.00-2.08 (m, 4H). MS obsd. (ESI$^+$) [(M+H)$^+$]: 342.1.

Example 58: [(2-chloro-3-fluoro-phenyl)-(5-chloro-3-pyrrolidin-1-yl-9H-xanthen-9-yl)methyl]acetate

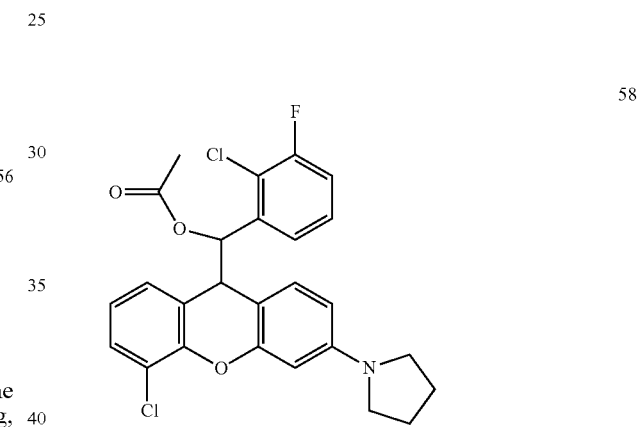

To a cooled solution of 1-(5-chloro-9H-xanthen-3-yl)pyrrolidine (50 mg, 175 μmol) in THF (15 mL) was added n-BuLi (2.4 M in heptane, 1.1 mL, 2.64 mmol) dropwise at −78° C. while keeping the temperature below −60° C. After the reaction mixture was stirred at −78° C. for 15 minutes, to the solution was added 2-chloro-3-fluorobenzaldehyde (277 mg, 1.75 mmol, dissolved in 1 mL THF) and the resulting reaction mixture was stirred at −78° C. for another 2 hours. Then to the reaction mixture was further added acetic anhydride (2.6 g, 175 μmol) and TEA (3.5 g, 175 μmol). The resulting mixture was stirred further at room temperature for 12 hours, then washed with brine, dried over anhydrous Na$_2$SO$_4$, and concentrated under reduced pressure. The residue was purified by column chromatography on silica gel (elution with PE:EtOAc=100:1 to 2:1) to give [(2-chloro-3-fluoro-phenyl)-(5-chloro-3-pyrrolidin-1-yl-9H-xanthen-9-yl)methyl]acetate (4.0 mg, 4%) as a white powder. $^1$H NMR (400 MHz, DMSO-d$_6$): δ ppm 7.43 (dd, J=1.51, 7.78 Hz, 1H), 7.34-7.40 (m, 1H), 7.27-7.34 (m, 1H), 6.90-7.05 (m, 2H), 6.72-6.89 (m, 2H), 6.22-6.33 (m, 2H), 6.04-6.08 (m, 1H), 4.47 (dd, J=5.40, 10.67 Hz, 1H), 3.23 (m, 4H), 1.92-2.00 (m, 7H). MS obsd. (ESI$^+$) [(M+H)$^+$]: 486.1.

Example 59: 5-chloro-3-pyrrolidin-1-yl-9-(trifluoromethyl)xanthen-9-ol

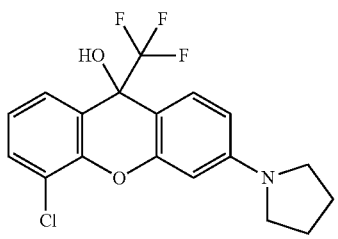

59

To a solution of 5-chloro-3-pyrrolidin-1-yl-xanthen-9-one (100 mg, 334 µmol) in THF (2 mL) was added trimethyl(trifluoromethyl)silane (285 mg, 2 mmol), TBAF (1 M in THF, 3.34 mL, 3.34 mmol), the mixture was then stirred at room temperature for 48 hours. The reaction mixture was then concentrated under reduced pressure and the residue was purified by preparative HPLC to give 5-chloro-3-pyrrolidin-1-yl-9-(trifluoromethyl)xanthen-9-ol (7.8 mg, 6.2%) as a white powder. $^1$H NMR (400 MHz, CDCl$_3$): δ ppm 7.84-7.90 (m, 1H), 7.67-7.73 (m, 1H), 7.42-7.47 (m, 1H), 7.11 (s, 1H), 6.44-6.49 (m, 1H), 6.38-6.42 (m, 1H), 3.33-3.38 (m, 4H), 1.99-2.07 (m, 4H). MS obsd. (ESI$^+$) [(M+H)$^+$]: 370.0.

Example 60: 1-[5-chloro-9-methoxy-9-(trifluoromethyl)xanthen-3-yl]pyrrolidine

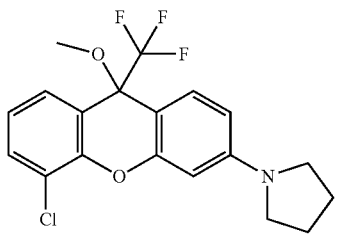

60

To a solution of 5-chloro-3-pyrrolidin-1-yl-9-(trifluoromethyl)xanthen-9-ol (50 mg, 135 µmol) and DMAP (120 mg, 984 µmol) in DCM (5 mL) was added trifluoroacetic anhydride (120 mg, 426 µmol). The resulting mixture was stirred at room temperature for 20 hours and then to the reaction was added MeOH (10 mL). The mixture was stirred at room temperature for another 30 min and then concentrated under reduced pressure. The residue was purified by column chromatography on silica gel (elution with PE:EtOAc=100:1 to 2:1) to give 1-[5-chloro-9-methoxy-9-(trifluoromethyl)xanthen-3-yl]pyrrolidine (20 mg, 32.8%) as an oil. $^1$H NMR (400 MHz, CDCl$_3$): δ ppm 7.59-7.65 (m, 1H), 7.50-7.54 (m, 1H), 7.44-7.48 (m, 1H), 7.15 (s, 1H), 6.50-6.55 (m, 1H), 6.43-6.46 (m, 1H), 3.38 (br t, J=6.65 Hz, 4H), 3.10 (s, 3H), 2.06 (td, J=3.26, 6.53 Hz, 4H). MS obsd. (ESI$^+$) [(M+H)$^+$]: 384.0.

Example 61: 1-[5-chloro-9-(trifluoromethyl)-9H-xanthen-3-yl]pyrrolidine

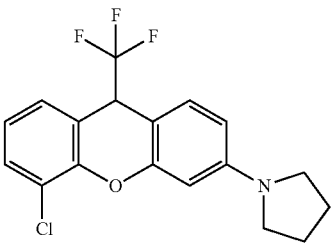

61

To a solution of 5-chloro-3-pyrrolidin-1-yl-9-(trifluoromethyl)xanthen-9-ol (50 mg, 135 µmol) in DCM (5 mL) was added triethylsilane (300 mg, 412 µL, 2.58 mmol) and BF$_3$.OEt$_2$ (280 mg, 250 µL, 1.97 mmol), the resulting mixture was then stirred at room temperature overnight. After the reaction was complete, the mixture was concentrated under reduced pressure and the residue was purified by preparative HPLC to give 1-[5-chloro-9-(trifluoromethyl)-9H-xanthen-3-yl]pyrrolidine (6.0 mg, 11.9%) as a white solid. $^1$H NMR (400 MHz, DMSO-d$_6$): δ ppm 7.59 (dd, J=1.38, 7.91 Hz, 1H), 7.44 (s, 1H), 7.18-7.28 (m, 2H), 6.44-6.51 (m, 1H), 6.34 (d, J=2.51 Hz, 1H), 5.15 (br d, J=9.03 Hz, 1H), 3.28 (br t, J=6.53 Hz, 4H), 1.97 (td, J=3.39, 6.27 Hz, 4H). MS obsd. (ESI$^+$) [(M+H)$^+$]: 354.1.

Example 62: 1-(5-fluoro-9H-xanthen-3-yl)pyrrolidine

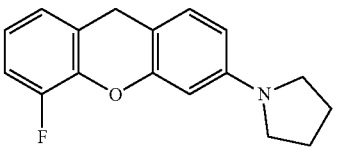

62

To a solution of 5-fluoro-3-pyrrolidin-1-yl-xanthen-9-one (700 mg, 2.1 mmol) in THF (10 mL) was added BH$_3$.Me$_2$S (2M in THF, 5 mL, 10.0 mmol), the mixture was then stirred at 60° C. for 12 hours. After the reaction was complete, the mixture was then concentrated under reduced pressure and the residue was purified by column chromatography on silica gel (elution with PE:EtOAc=10:1 to 1:2) to give 1-(5-fluoro-9H-xanthen-3-yl)pyrrolidine (250 mg, 44.2%) as a white solid. $^1$H NMR (400 MHz, CDCl3): δ ppm 6.87-7.06 (m, 4H), 6.37 (s, 2H), 3.98 (s, 2H), 3.29 (t, J=6.65 Hz, 4H), 2.02 (td, J=3.29, 6.71 Hz, 4H). MS obsd. (ESI$^+$) [(M+H)$^+$]: 270.2.

Example 63: 9-fluoro-2-pyrrolidin-1-yl-chromeno[2,3-b]pyridin-5-one

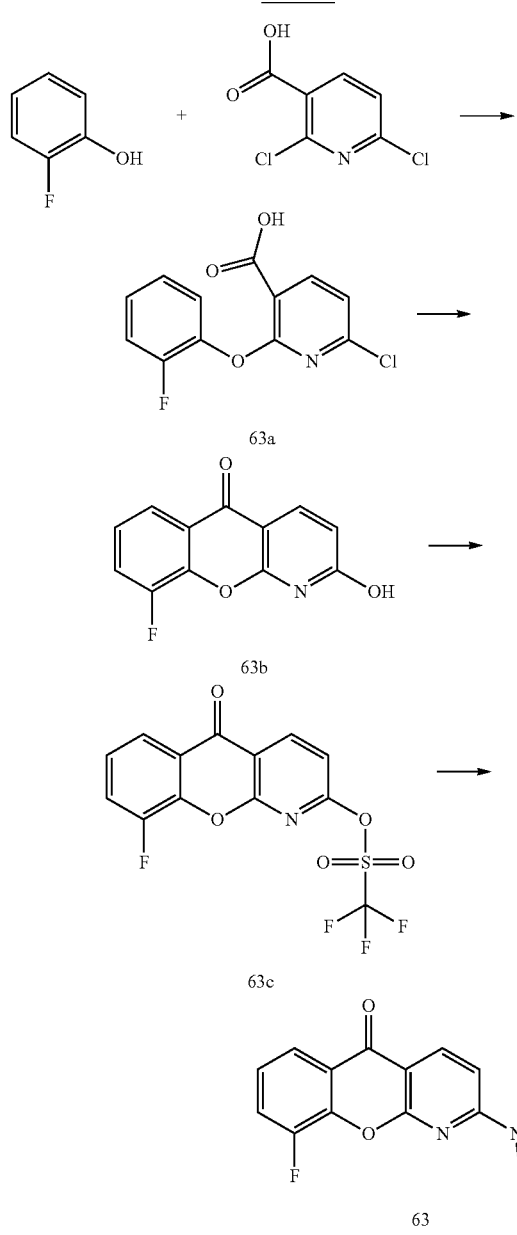

Example 63 was prepared according to Scheme 9.

Step 1: Preparation of 6-chloro-2-(2-fluorophenoxy)pyridine-3-carboxylic Acid

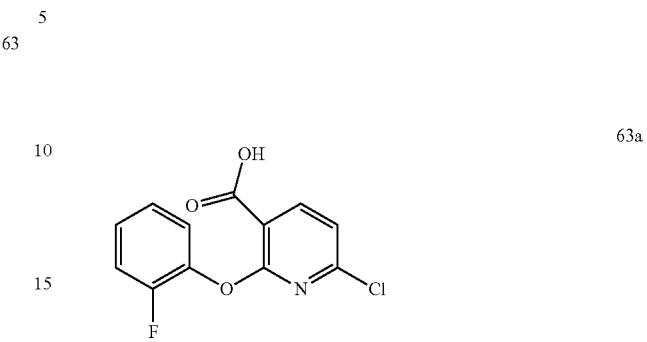

A mixture of 2,6-dichloropyridine-3-carboxylic acid (6.68 g, 31.8 mmol), 2-fluorophenol (3.0 g, 26.8 mmol), $K_2CO_3$ (7.4 g, 53.6 mmol) and Cu (10.2 g, 160.6 mmol) in dry DMF (60 mL) was stirred at 100° C. for 16 hours. The resulting mixture was then filtered and the filtrate was poured into water (500 mL) and adjusted to pH-5 with 2N HCl. The resulting mixture was extracted with EtOAc (300 mL) three times. The combined organic layer was washed with brine, dried over anhydrous $Na_2SO_4$ and concentrated under reduced pressure to give the crude product of 6-chloro-2-(2-fluorophenoxy)pyridine-3-carboxylic acid (crude, 7.0 g, 76.8% purity), which was used in the next step without further purification. MS obsd. (ESI$^+$) [(M+H)$^+$]: 268.1

Step 2: 9-fluoro-2-hydroxy-chromeno[2,3-b]pyridin-5-one

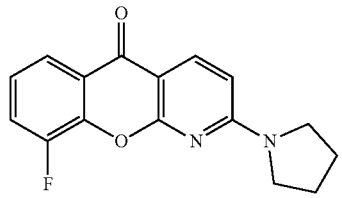

A mixture of 6-chloro-2-(2-fluorophenoxy)pyridine-3-carboxylic acid (1.5 g, 5.6 mmol, crude prepared above) in concentrated $H_2SO_4$ (20.0 mL) was stirred at 90° C. for 16 hours. The resulting mixture was poured into ice (100 g) and stirred for 15 minutes to yield a white suspension. The resulting suspension was filtered and the solid was dried in vacuo to afford 9-fluoro-2-hydroxy-chromeno[2,3-b]pyridin-5-one (0.8 g, 61.5%) as a pale solid. MS obsd. (ESI$^+$) [(M+H)$^+$]: 231.9.

Step 3: (9-fluoro-5-oxo-chromeno[2,3-b]pyridin-2-yl) Trifluoromethanesulfonate

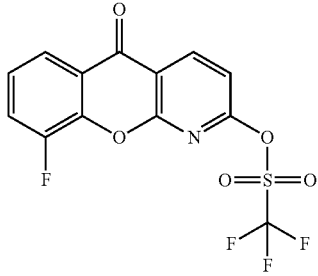

63c

To a mixture of 9-fluoro-2-hydroxy-chromeno[2,3-b] pyridin-5-one (180.0 mg, 0.779 mmol) in DCM (10 mL) was added TEA (197.0 mg, 1.95 mmol) and trifluoromethane-sulfonic anhydride (330.0 mg, 1.17 mmol) at 0° C. The mixture was stirred at room temperature for 2 hours. Then the reaction was quenched with water (20 mL) and the resulting mixture was extracted with DCM (20 mL) three times. The combined organic layer was dried over anhydrous $Na_2SO_4$ and concentrated under reduce pressure to afford the crude of (9-fluoro-5-oxo-chromeno[2,3-b]pyridin-2-yl) trifluoromethanesulfonate (207.0 mg, 73.20%) as a pale-white solid, which was used in the next step without further purification. MS obsd. (ESI$^+$) [(M+H)$^+$]: 364.0.

Step 4: Preparation of 9-fluoro-2-pyrrolidin-1-yl-chromeno[2,3-b]pyridin-5-one

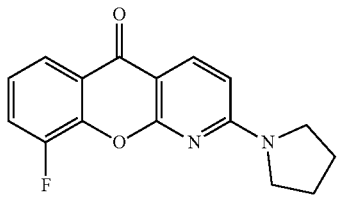

63

A mixture of (9-fluoro-5-oxo-chromeno[2,3-b]pyridin-2-yl) trifluoromethanesulfonate (200.0 mg, 0.551 mmol) in pyrrolidine (10.0 mL) was stirred at 60° C. for 15 hours. Then the mixture was concentrated under reduced pressure and the residue was purified by preparative HPLC to give 9-fluoro-2-pyrrolidin-1-yl-chromeno[2,3-b]pyridin-5-one (35.0 mg, 22.36%) as a light yellow solid. $^1$H NMR (400 MHz, CDCl$_3$): δ ppm 8.36 (d, J=8.8 Hz, 1H), 8.06-8.04 (m, 1H), 7.47 (ddd, J=1.5, 8.2, 10.1 Hz, 1H), 7.33-7.28 (m, 1H), 6.50 (d, J=8.8 Hz, 1H), 3.75-3.90 (m, 2H), 3.48-3.59 (m, 2H), 1.97-2.10 (m, 4H). MS obsd. (ESI$^+$) [(M+H)$^+$]: 285.0.

Example 64: 9-chloro-2-pyrrolidin-1-yl-chromeno [2,3-b]pyridin-5-one

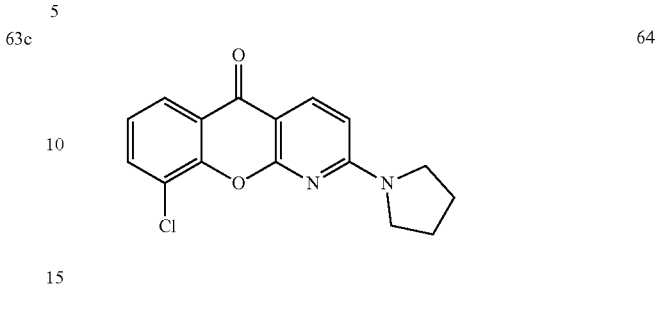

64

9-chloro-2-pyrrolidin-1-yl-chromeno[2,3-b]pyridin-5-one was prepared in analogy to the procedure described for the preparation of Example 63 by using 2-chlorophenol as the starting material instead of 2-fluorophenol in Step 1. $^1$H NMR (400 MHz, MeOD-d$_4$): δ ppm 8.29-8.27 (d, J=8.8 Hz, 1H), 8.15-8.13 (d, J=8.0 Hz, 1H), 7.89-7.87 (t, 1H), 7.43-7.39 (t, 1H), 6.71-6.69 (d, J=8.8 Hz, 1H), 3.77 (m, 2H), 3.57 (m, 2H), 2.14-2.09 (m, 4H). MS obsd. (ESI$^+$) [(M+H)$^+$]: 301.1.

Example 65: 5-chloro-3-[3-(morpholine-4-carbonyl) pyrrolidin-1-yl]xanthen-9-one

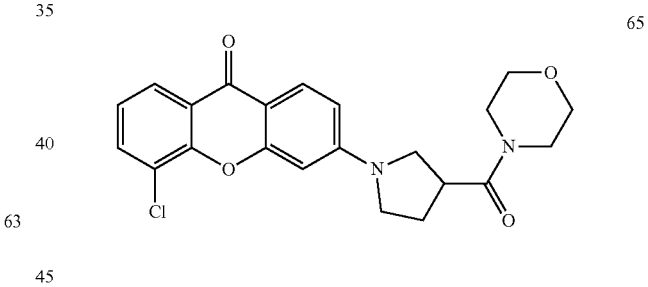

65

To a solution of 1-(5-chloro-9-oxo-xanthen-3-yl)pyrrolidine-3-carboxylic acid (Example 3, 0.50 g, 0.145 mmol) in DMF (2 mL) was added morpholine (12.7 mg, 0.145 mmol), HATU (55.3 g, 0.145 mmol) and N,N-diisopropylethylamine (18.8 mg, 0.145 mmol) at 25° C. After being stirred at room temperature for 1 hour, the resulting mixture was poured into water (30 mL) and extracted with EtOAc (50 mL) for three times. The combined organic phase was washed with brine, dried over anhydrous $Na_2SO_4$, and concentrated under reduced pressure. The residue was purified by Preparative HPLC to give 5-chloro-3-[3-(morpholine-4-carbonyl)pyrrolidin-1-yl]xanthen-9-one as a solid (13.0 mg, 21.6%). $^1$H NMR (DMSO-d$_6$, 400 MHz): δ ppm 8.07-8.11 (m, 1H), 7.93-7.99 (m, 2H), 7.38-7.44 (m, 1H), 6.76-6.82 (m, 1H), 6.54 (d, J=2.26 Hz, 1H), 3.53-3.74 (m, 8H), 3.44-3.52 (m, 5H), 2.11-2.28 (m, 2H). MS obsd. (ESI$^+$) [(M+H)$^+$]: 413.1.

Example 66: 1-(5-chloro-8-fluoro-9-oxo-xanthen-3-yl)pyrrolidine-3-carboxylic Acid

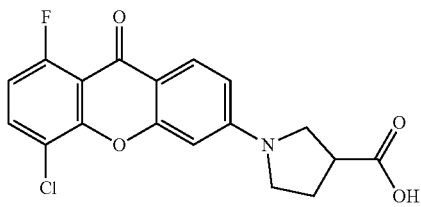

Example 66 was prepared according to Scheme 10.

Scheme 10

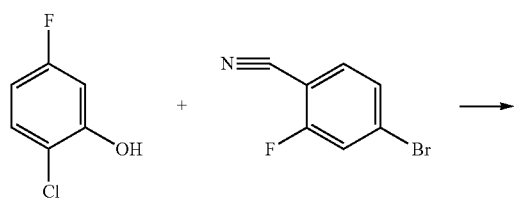

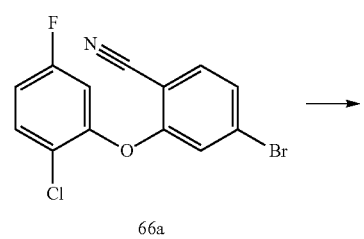

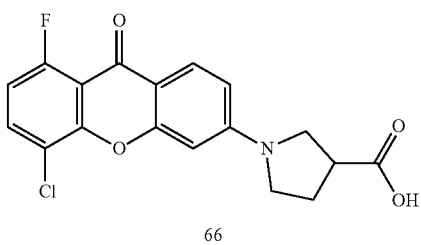

Step 1: Preparation of 4-bromo-2-(2-chloro-5-fluoro-phenoxy)benzonitrile

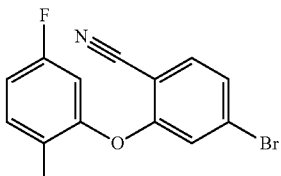

To a solution of 4-bromo-2-fluoro-benzonitrile (4.9 g, 24.7 mmol), 2-chloro-5-fluoro-phenol (3.0 g, 2.6 mmol) in DMF (50 mL) was added $K_2CO_3$ (1.7 g, 12.0 mmol), Cu powder (7.9 g, 123.3 mmol) at 25° C. and the mixture was then stirred at 120° C. for 16 hours. The reaction mixture was cooled to 20° C. and poured into water (100 mL). The resulting mixture was adjusted to pH=4-5 by addition of 1N HCl dropwise and then extracted by EtOAc (250 mL) twice. The combined organic layer was washed with brine (100 mL), dried over anhydrous $Na_2SO_4$ and concentrated under reduced pressure to give the crude of 4-bromo-2-(2-chloro-5-fluoro-phenoxy)benzonitrile (5.0 g, 65.3% purity) as a yellow solid, which was used in the next step directly without further purification. MS obsd. (ESI$^+$) [(M+H)$^+$]: 357.9.

Step 2: Preparation of 1-[3-(2-chloro-5-fluoro-phenoxy)-4-cyano-phenyl]pyrrolidine-3-carboxylic Acid

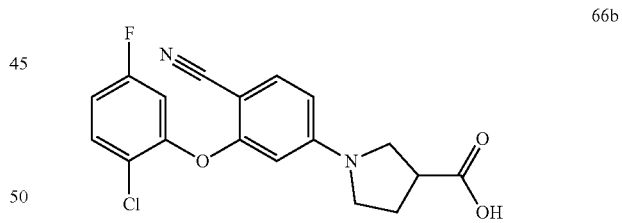

To a solution of 4-bromo-2-(2-chloro-5-fluoro-phenoxy)benzonitrile (2.5 g, 7.6 mmol, prepared above) in DMF (20 mL) was added methyl pyrrolidine-3-carboxylate (1.5 g, 11.5 mmol) and $K_2CO_3$ (3.1 g, 22.8 mmol), then the mixture was stirred at 110° C. for 12 hours. The reaction mixture was then diluted by water (50 mL) and the resulting suspension was filtered. The filter cake was collected and purified by preparative HPLC to give 1-[3-(2-chloro-5-fluoro-phenoxy)-4-cyano-phenyl]pyrrolidine-3-carboxylic acid (0.5 g, 18.2%) as a yellow solid. MS obsd. (ESI$^+$) [(M+H)$^+$]: 361.0.

Step 3: Preparation of 1-(5-chloro-8-fluoro-9-oxo-xanthen-3-yl)pyrrolidine-3-carboxylic Acid

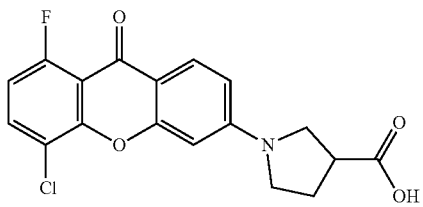

66

A solution of 1-[3-(2-chloro-5-fluoro-phenoxy)-4-cyano-phenyl]pyrrolidine-3-carboxylic acid (150 mg, 0.41 mmol) in polyphosphoric acid (2 mL) was stirred at 150° C. for 2 hours under N₂ atmosphere. The reaction mixture was cooled to room temperature and diluted with water (10 mL). The resulting suspension was filtered and the filter cake was purified by preparative HPLC to give 1-(5-chloro-8-fluoro-9-oxo-xanthen-3-yl)pyrrolidine-3-carboxylic acid (20 mg, 13.3%) as a yellow solid. $^1$H NMR (DMSO-$d_6$, 400 MHz): δ ppm 12.64 (s, 1H), 7.91-7.83 (m, 2H), 7.19-7.16 (m, 1H), 6.69-6.66 (m, 1H), 6.38 (s, 1H), 3.60-3.56 (m, 2H), 3.55-3.44 (m, 2H), 3.26-3.24 (m, 1H), 2.25-2.19 (m, 2H). MS obsd. (ESI$^+$) [(M+H)$^+$]: 362.0.

Example 67: 1-[5-chloro-9-oxo-8-(trifluoromethyl)xanthen-3-yl]pyrrolidine-3-carboxylic Acid

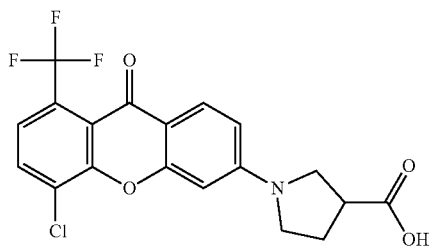

67

Example 67 was prepared in analogy to the procedure described for the preparation of Example 5 by using 6-bromo-4-chloro-1-(trifluoromethyl)xanthen-9-one (intermediate 18) as the starting material instead of 3-bromo-5-fluoro-xanthen-9-one (intermediate 3) in Step 1. $^1$H NMR (DMSO-$d_6$, 400 MHz): δ ppm 12.66 (s, 1H), 8.12-8.10 (d, J=8.4 Hz, 1H), 7.96-7.93 (d, J=8.8 Hz, 1H), 7.81-7.79 (d, J=8.4, 1H), 6.82-6.79 (d, J=8.8, 1H), 6.52 (s, 1H), 3.67-3.64 (m, 2H), 3.63-3.61 (m, 2H), 3.29-3.27 (m, 1H), 2.28-2.20 (m, 2H). MS obsd. (ESI$^+$) [(M+H)$^+$]: 412.0.

Example 68: 2-chloro-5-fluoro-3-pyrrolidin-1-yl-xanthen-9-one

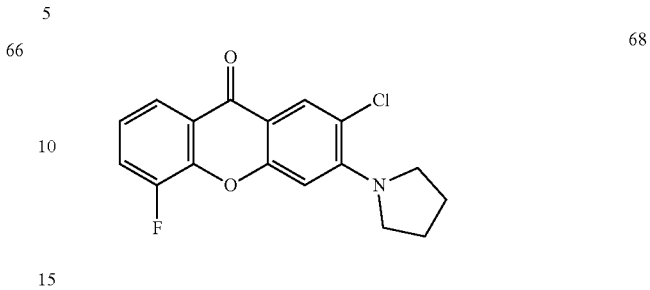

68

Example 68 was prepared in analogy to the procedure described for the preparation of Example 1 by using 3-bromo-2-chloro-5-fluoro-xanthen-9-one (intermediate 19) as the starting material instead of 3-bromo-5-chloro-xanthen-9-one (intermediate 1) in Step 1. $^1$H NMR (CDCl₃, 400 MHz): δ ppm 8.09 (s, 1H), 7.97 (d, J=8.0 Hz, 1H), 7.38-7.33 (m, 1H), 7.20-7.16 (m, 1H), 6.60 (s, 1H), 3.59 (t, J=6.4 Hz, 4H), 1.96-1.92 (m, 4H). MS obsd. (ESI$^+$) [(M+H)$^+$]: 318.0.

Example 69: (3R)-1-(5,8-dichloro-9-oxo-xanthen-3-yl)pyrrolidine-3-carboxylic Acid

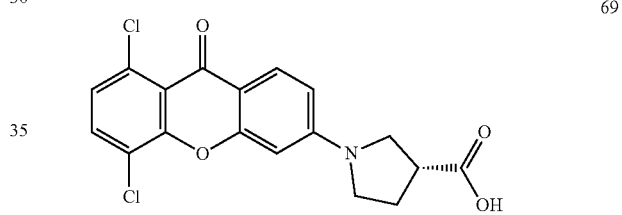

69

Example 69 was prepared in analogy to the procedure described for the preparation of Example 5 by using 6-bromo-1,4-dichloro-xanthen-9-one (intermediate 10) and methyl (3R)-pyrrolidine-3-carboxylate as the starting materials instead of 3-bromo-5-fluoro-xanthen-9-one (intermediate 3) and methyl pyrrolidine-3-carboxylate in Step 1. $^1$H NMR (DMSO-$d_6$, 400 MHz): δ ppm 7.97-7.79 (m, 2H), 7.34-7.32 (d, J=8.0 Hz, 1H), 6.66-6.64 (d, J=8.0 Hz, 1H), 6.29 (s, 1H), 3.48-3.16 (m, 4H), 2.99-2.89 (m, 1H), 2.20-2.14 (m, 2H). MS obsd. (ESI$^+$) [(M+H)$^+$]: 377.8.

Example 70: 1-(5,7-dichloro-9-oxo-xanthen-3-yl)pyrrolidine-3-carboxylic Acid

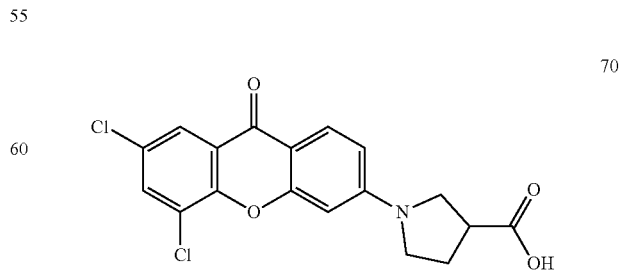

70

Example 70 was prepared according to Scheme 11.

Scheme 11

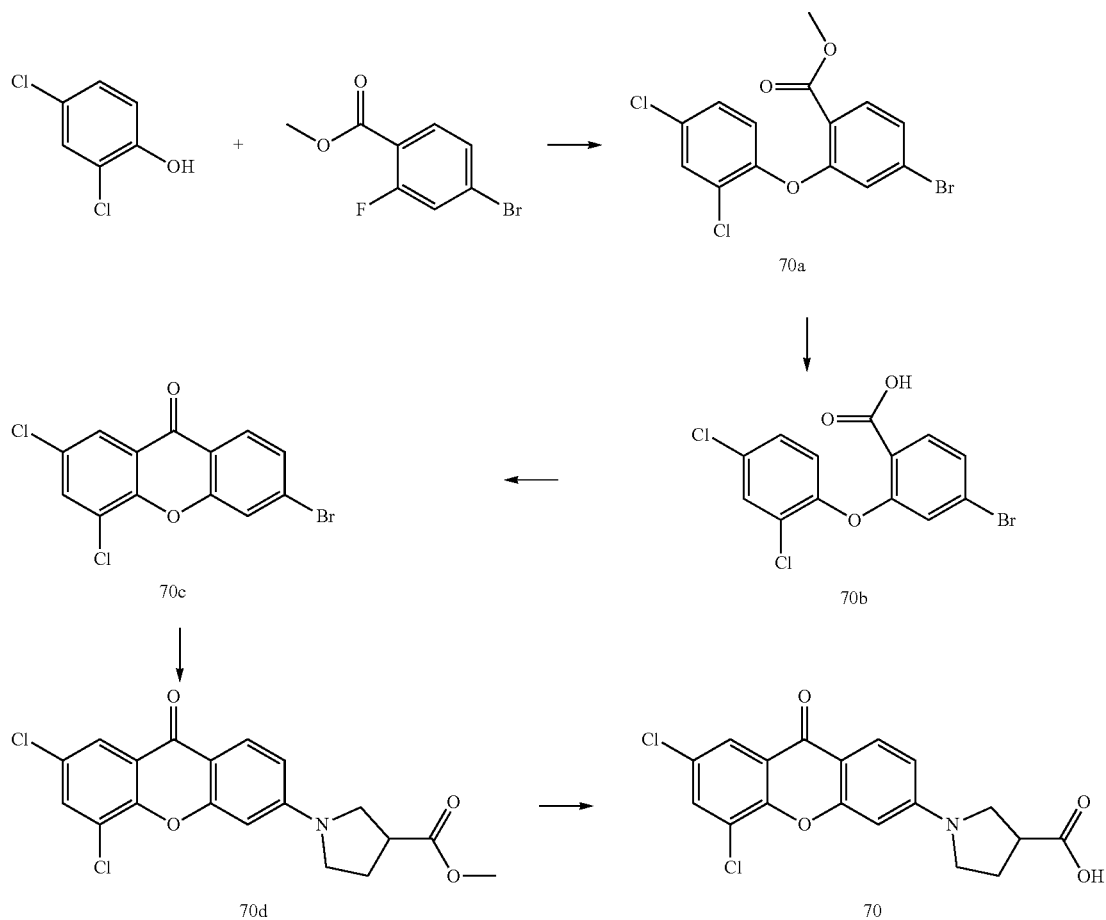

Step 1: Preparation of Methyl 4-bromo-2-(2,4-dichlorophenoxy)benzoate

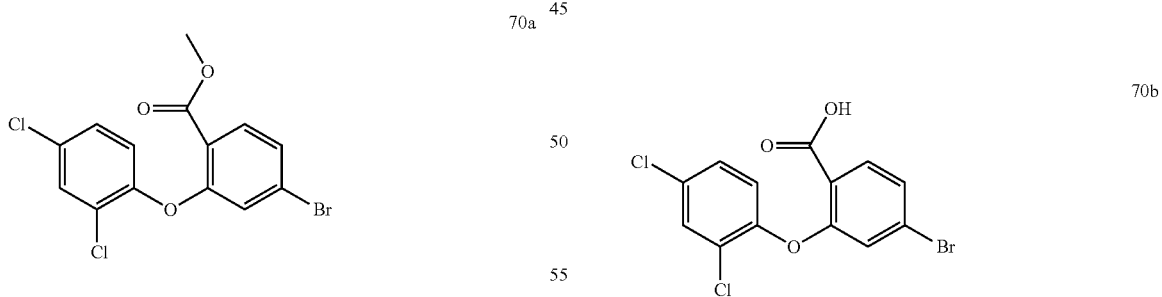

A mixture of methyl 4-bromo-2-fluoro-benzoate (3.0 g, 12.9 mmol), 2,4-dichlorophenol (2.1 g, 12.9 mmol), K$_2$CO$_3$ (3.6 g, 25.7 mmol) and Cu (4.9 g, 77.2 mmol) in dry DMF (20 mL) was stirred at 100° C. for 16 hours. The resulting mixture was then filtered and the filtrate was partitioned between EtOAc (300 mL) and water (300 mL). The organic layer was separated and the aqueous phase was extracted with EtOAc (300 mL) three times. The combined organic layer was washed with brine, dried over anhydrous Na$_2$SO$_4$ and concentrated under reduced pressure to give methyl 4-bromo-2-(2,4-dichlorophenoxy)benzoate (crude, 4.5 g) as a yellow oil, which was used in the next step without further purification. MS obsd. (ESI$^+$) [(M+H)$^+$]: 376.9.

Step 2: Preparation of 4-bromo-2-(2,4-dichlorophenoxy)benzoic Acid

A mixture of methyl 4-bromo-2-(2,4-dichlorophenoxy) benzoate (4.5 g, 12.0 mmol, crude prepared above), NaOH (1.4 g, 35.9 mmol) in a mixed solvent of methanol (100 mL) and water (20 mL) was stirred at 60° C. for 4 hours. The resulting mixture was adjusted to pH=4 with concentrated HCl to yield a suspension. The solid was collected by filtration and dried under reduced pressure to give 4-bromo-2-(2,4-dichlorophenoxy)benzoic acid (crude, 2.4 g) as a white solid, which was used in the next step without further purification. MS obsd. (ESI$^+$) [(M+H)$^+$]: 362.9.

Step 3: Preparation of 6-bromo-2,4-dichloro-xanthen-9-one

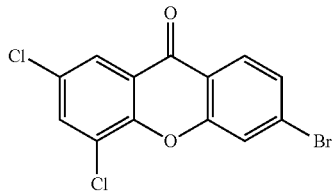

70c

A mixture of 4-bromo-2-(2,4-dichlorophenoxy)benzoic acid (2.4 g, 6.7 mmol, crude prepared above) and H₂SO₄ (50.0 mL) was stirred at 100° C. for 16 hours. The mixture was poured into ice (100 g) and extracted with EtOAc (400 mL) three times. The combined organic layer was washed with brine, dried over anhydrous Na₂SO₄ and concentrated under reduced pressure to give 6-bromo-2,4-dichloro-xanthen-9-one (1.5 g, crude) as a white solid, which was used in the next step without further purification. MS obsd. (ESI⁺) [(M+H)⁺]: 342.8.

Step 4: Preparation of Methyl 1-(5,7-dichloro-9-oxo-xanthen-3-yl)pyrrolidine-3-carboxylate

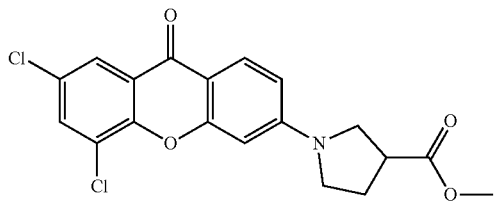

70d

A mixture of 6-bromo-2,4-dichloro-xanthen-9-one (0.5 g, 1.4 mmol, crude prepared above), methyl pyrrolidine-3-carboxylate hydrochloride (0.24 g, 1.4 mmol), 1,8-diazabicyclo[5.4.0]undec-7-ene (0.73 g, 2.9 mmol) in DMSO (10 mL) was stirred at 100° C. for hours. The mixture was cooled and partitioned between ethyl acetate (150 mL) and water (80 mL). The organic phase was separated and the aqueous phase was extracted with EtOAc (150 mL) twice. The combined organic layer was washed with brine, dried over anhydrous Na₂SO₄ and concentrated under reduced pressure to give the crude of methyl 1-(5,7-dichloro-9-oxo-xanthen-3-yl)pyrrolidine-3-carboxylate (0.45 g) as a brown oil, which was used in the next step without further purification. MS obsd. (ESI⁺) [(M+H)⁺]: 392.0.

Step 5: Preparation of 1-(5,7-dichloro-9-oxo-xanthen-3-yl)pyrrolidine-3-carboxylic Acid

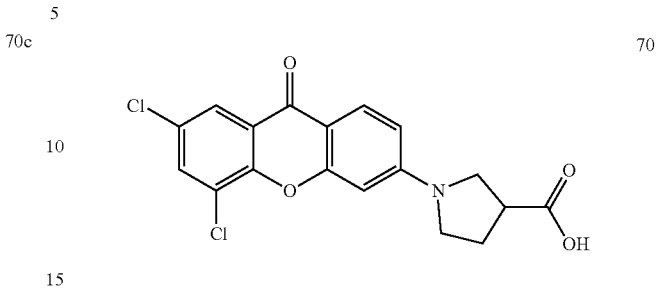

70

A mixture of methyl 1-(5,7-dichloro-9-oxo-xanthen-3-yl)pyrrolidine-3-carboxylate (0.45 g, 1.1 mmol, crude, prepared above), lithium hydroxide monohydrate (0.14 g, 3.44 mmol) in a mixed solvent of THF (2 mL), MeOH (2 mL) and water (0.5 mL) was stirred at 50° C. for 3 hours. The resulting mixture was adjusted to pH around 4 with 2N HCl and then extracted with EtOAc (25 mL). The organic layer was washed with brine, dried over anhydrous Na₂SO₄ and concentrated under reduced pressure to give the crude of 1-(5,7-dichloro-9-oxo-xanthen-3-yl)pyrrolidine-3-carboxylic acid, which was purified by preparative HPLC to give 1-(5,7-dichloro-9-oxo-xanthen-3-yl)pyrrolidine-3-carboxylic acid (57.0 mg, 13.7%) as a yellow solid. ¹H NMR (DMSO-d₆, 400 MHz): δ ppm 12.64 (s, 1H), 8.09 (s, 1H), 8.09 (s, 1H), 7.92-7.90 (d, J=9.2 Hz, 1H), 6.74-6.72 (d, J=9.2 Hz, 1H), 6.47 (s, 1H), 3.64-3.59 (m, 2H), 3.48-3.46 (m, 2H), 3.46-3.34 (m, 1H), 2.28-2.08 (m, 2H). MS obsd. (ESI⁺) [(M+H)⁺]: 378.0.

Example 71: 1-(5-chloro-7-fluoro-9-oxo-xanthen-3-yl)pyrrolidine-3-carboxylic Acid

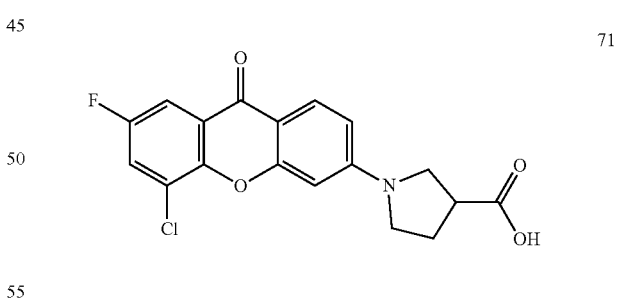

71

Example 71 was prepared in analogy to the procedure described for the preparation of Example 70 by using 2-chloro-4-fluoro-phenol as the starting materials instead of 2-chloro-4-fluoro-phenol in Step 1. ¹H NMR (DMSO-d₆, 400 MHz): δ ppm 8.03 (dd, J=8.2, 3.1 Hz, 1H), 7.95 (d, J=8.8 Hz, 1H), 7.77 (dd, J=8.3, 3.0 Hz, 1H), 6.79 (dd, J=9.0, 2.0 Hz, 1H), 6.52 (d, J=1.8 Hz, 1H), 3.60-3.69 (m, 2H), 3.46-3.49 (m, 2H), 3.22-3.33 (m, 1H), 2.19-2.30 (m, 2H). MS obsd. (ESI⁺) [(M+H)⁺]: 362.0.

Example 72: (3S)-1-(5-chloro-9-oxo-thioxanthen-3-yl)pyrrolidine-3-carboxylic Acid

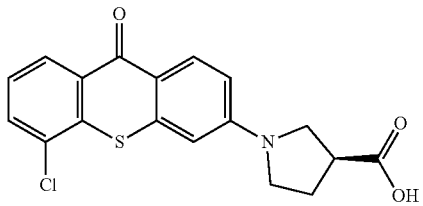

72

Example 72 was prepared in analogy to the procedure described for the preparation of Example 4 by using 3-bromo-5-chloro-thioxanthen-9-one (compound 6c) instead of 3-bromo-5-chloro-xanthen-9-one (intermediate 1). $^1$H NMR (DMSO-d$_6$, 400 MHz): δ ppm 12.60 (br s, 1H), 8.31-8.54 (m, 1H), 8.14-8.30 (m, 1H), 7.83-7.97 (m, 1H), 7.43-7.65 (m, 1H), 6.76-6.97 (m, 2H), 3.55-3.68 (m, 2H), 3.40-3.53 (m, 2H), 3.21-3.29 (m, 1H), 2.15-2.32 (m, 2H). MS obsd. (ESI$^+$) [(M+H)$^+$]: 359.8.

Example 73: (3R)-1-(5-chloro-9-oxo-thioxanthen-3-yl)pyrrolidine-3-carboxylic Acid

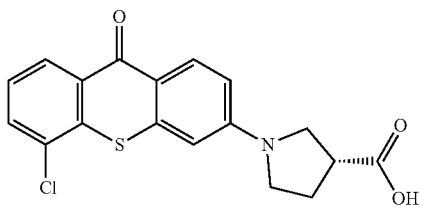

73

Example 73 was prepared in analogy to the procedure described for the preparation of Example 3 by using 3-bromo-5-chloro-thioxanthen-9-one (compound 6c) instead of 3-bromo-5-chloro-xanthen-9-one (intermediate 1). $^1$H NMR (DMSO-d$_6$, 400 MHz): δ ppm 12.60 (br s, 1H), 8.31-8.54 (m, 1H), 8.14-8.30 (m, 1H), 7.83-7.97 (m, 1H), 7.43-7.65 (m, 1H), 6.76-6.97 (m, 2H), 3.55-3.68 (m, 2H), 3.40-3.53 (m, 2H), 3.21-3.29 (m, 1H), 2.15-2.32 (m, 2H). MS obsd. (ESI$^+$) [(M+H)$^+$]: 359.8.

Example 74: (3R)-1-(5-chloro-2-methyl-9-oxo-xanthen-3-yl)pyrrolidine-3-carboxylic Acid

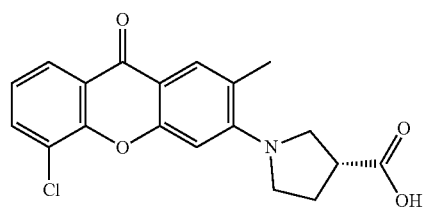

74

Example 74 was prepared in analogy to the procedure described for the preparation of Example 3 by using 3-bromo-5-chloro-2-methyl-xanthen-9-one (intermediate 4) as the starting materials instead of 3-bromo-5-chloro-xanthen-9-one (intermediate 1). $^1$H NMR (DMSO-d$_6$, 400 MHz): δ ppm 8.10-8.08 (m, 1H), 7.96-7.94 (m, 1H), 7.79 (m, 1H), 7.39-7.43 (m, 1H), 6.65-6.67 (m, 1H), 3.72-3.74 (m, 2H), 3.57-3.61 (m, 2H), 3.16-3.20 (m, 1H), 2.14-2.30 (m, 2H), 1.35 (s, 3H). MS obsd. (ESI$^+$) [(M+H)$^+$]: 358.1.

Example 75: 1-(5-chloro-9-methyl-9H-xanthen-3-yl)pyrrolidine-3-carboxylic Acid

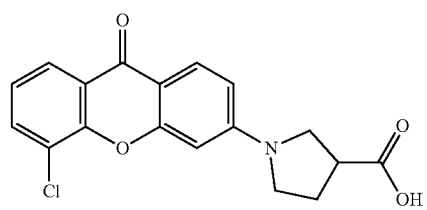

75

Example 75 was prepared according to Scheme 12.

Scheme 12

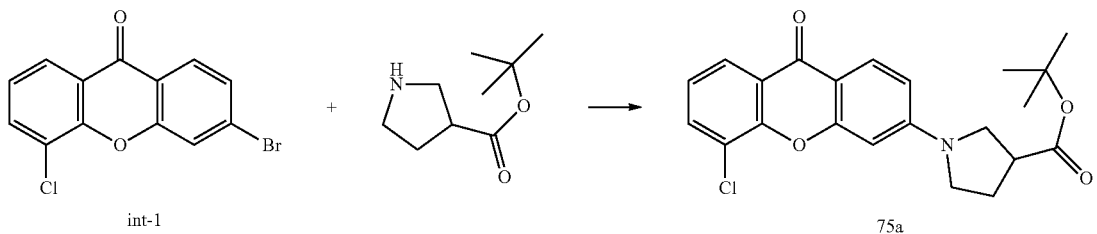

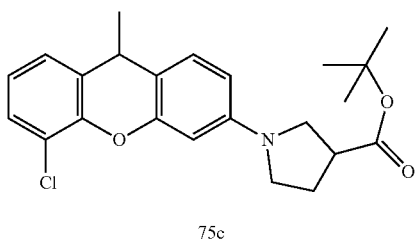

75c

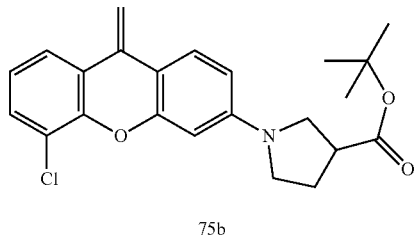

75b

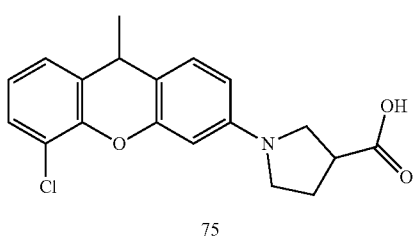

75

Step 1: Preparation of Tert-Butyl 1-(5-chloro-9-oxo-xanthen-3-yl)pyrrolidine-3-carboxylate Step 2: Preparation of Tert-Butyl 1-(5-chloro-9-methylene-xanthen-3-yl)pyrrolidine-3-carboxylate

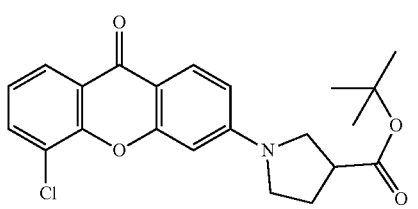

75a

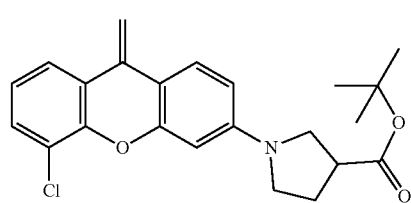

75b

A mixture of 3-bromo-5-chloro-xanthen-9-one (intermediate 1, 309 mg, 1.0 mmol), tert-butyl pyrrolidine-3-carboxylate (256 mg, 1.5 mmol), $K_3PO_4$ (0.14 g, 0.650 mmol) (424 mg, 2.0 mmol) in DMF (10 mL) was stirred at 100° C. for 10 hours. The mixture was cooled and partitioned between ethyl acetate (100 mL) and water (50 mL). The organic phase was separated out and the aqueous phase was extracted with EtOAc (100 mL) twice. The combined organic layer was washed with brine, dried over anhydrous $Na_2SO_4$ and concentrated under reduced pressure to give the crude of tert-butyl 1-(5-chloro-9-oxo-xanthen-3-yl)pyrrolidine-3-carboxylate (300 mg) as a yellow solid, which was used in the next step without further purification. MS obsd. (ESI$^+$) [(M+H)$^+$]: 400.1.

To a cooled solution of tert-butyl 1-(5-chloro-9-oxo-xanthen-3-yl)pyrrolidine-3-carboxylate (300 mg, 0.75 mmol, crude prepared above) in THF (4 mL) was added methyllithium (1M in hexane, 1.5 mL, 1.5 mmol) dropwise at −78° C. After the addition was complete, the reaction mixture was warmed to room temperature and stirred at for 3 hours. The reaction was then quenched by $NH_4Cl$ solution (3 mL) and the resulting mixture was extracted by EtOAc (10 mL) three times. The combined organic layer was concentrated under reduced pressure to give a crude product of tert-butyl 1-(5-chloro-9-methylene-xanthen-3-yl)pyrrolidine-3-carboxylate (290 mg, 97.5%), which was used in the next step without further purification. MS obsd. (ESI$^+$) [(M+H)$^+$]: 398.1

Step 3: Preparation of Tert-Butyl 1-(5-chloro-9-methyl-9H-xanthen-3-yl)pyrrolidine-3-carboxylate

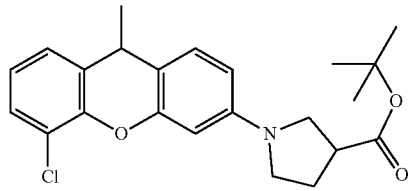
75c

To a solution of tert-butyl 1-(5-chloro-9-methylene-xanthen-3-yl)pyrrolidine-3-carboxylate (200 mg, 0.5 mmol) in MeOH (5 mL) was added Pd/C (20 mg). The resulting mixture was hydrogenated under $H_2$ atmosphere at room temperature overnight. After the reaction was complete, the reaction was filtered through silica gel pad and the filtrate was concentrated under reduced pressure to give the crude of tert-butyl 1-(5-chloro-9-methyl-9H-xanthen-3-yl)pyrrolidine-3-carboxylate (200 mg), which was used in the next step without further purification. MS obsd. (ESI$^+$) [(M+H)$^+$]: 400.1.

Step 5: Preparation of 1-(5-chloro-9-methyl-9H-xanthen-3-yl)pyrrolidine-3-carboxylic Acid

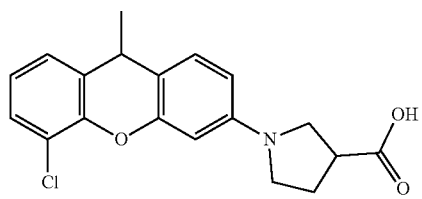
75

The suspension of tert-butyl 1-(5-chloro-9-methyl-9H-xanthen-3-yl)pyrrolidine-3-carboxylate (200 mg) in concentrated hydrochloric acid (5 mL) was stirred under reflux for 2 hours. After the reaction was complete, the mixture was concentrated under reduced pressure. The residue was purified by preparative HPLC to give 1-(5-chloro-9-methyl-9H-xanthen-3-yl)pyrrolidine-3-carboxylic acid (11.0 mg, 6.4%) as a yellow solid. $^1$H NMR (DMSO-d$_6$, 400 MHz): δ ppm 7.36 (dd, J=7.8, 1.5 Hz, 1H), 7.31 (dd, J=7.9, 1.1 Hz, 1H), 7.14 (d, J=8.3 Hz, 1H), 7.07 (t, J=7.8 Hz, 1H), 6.39 (dd, J=8.4, 2.3 Hz, 1H), 6.23 (d, J=2.4 Hz, 1H), 4.07 (q, J=7.0 Hz, 1H), 3.38-3.54 (m, 2H), 3.24-3.37 (m, 2H), 3.11-3.23 (m, 1H), 2.08-2.29 (m, 2H), 1.35 (d, J=6.8 Hz, 3H). MS obsd. (ESI$^+$) [(M+H)$^+$]: 344.1.

Reference Compound: 5,8-dihydroxy-3-methoxy-1-[(2S,3R,4S,5S,6R)-3,4,5-trihydroxy-6-(hydroxymethyl)tetrahydropyran-2-yl]oxy-xanthen-9-one (Swertianolin)

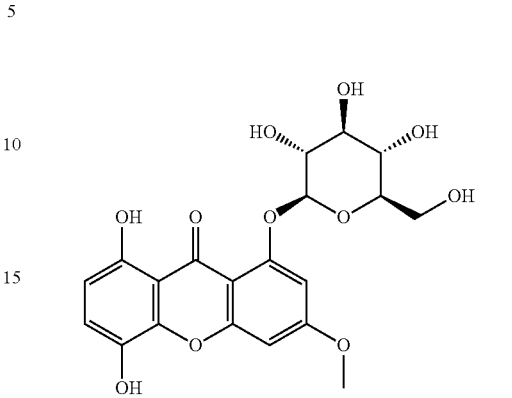

Swertianolin disclosed in CN104370871 (A) was used as the reference compound.

BIOLOGICAL EXAMPLES

Example 76: HepDES19 Primary Screen Assay

The assay was employed to primarily screen for novel cccDNA inhibitors. HepDES19 is an engineered cell line which contains a 1.1 unit length HBV genome, and pgRNA transcription from the transgene is controlled by Tetracycline (Tet). In the absence of Tet, pgRNA transcription will be induced, but HBV e antigen (HBeAg) could not be produced from this pgRNA due to the fact that the very short leader sequence before the HBeAg start codondisrupted the start codon. Only after cccDNA is formed, the missing leader sequence and start codon mutation would be restored from the 3'-terminal redundancy of pgRNA, and then HBeAg could be synthesized. Therefore, HBeAg could be used as a surrogate marker for cccDNA (Zhou, T. et al., Antiviral Res(2006), 72(2), 116-124; Guo, H. et al., J. Virol (2007), 81(22), 12472-12484).

HepDES19 cells were seeded at $2×10^6$ cells per T150 flask and cultured with the culture medium (Dulbecco's Modified Eagle Medium: Nutrient Mixture F-12 (DMEM:F12, Gibco Cat. 11320-82), 10% Fetal Bovine Serum (FBS, Clontech Cat. 631101), 0.1 mM Non-Essential Amino Acids Solution (NEAA, Gibco Cat. 11140-050), 50 μg/mL Penicillin-Streptomycin (PS, Invitrogen Cat. 15140-163), 500 μg/mL Geneticin (G418, Invitrogen Cat. 10131-027) containing 3 μg/mL Tet (Sigma, Cat. 87128) for 5 days. Cells were then seeded at $4×10^6$ cells per T150 in the same culture medium as described above in the absence of Tet for 8 days. Cells were then harvested and frozen at density of $2×10^6$ cells per mL. For compound testing, the frozen cells were thawed and seeded into 96-well plates at a density of $6×10^4$ cells per well. At 24 hrs after seeding, half log serial dilutions of compounds made with Dimethyl sulfoxide (DMSO, Sigma, Cat. D2650) were further diluted with the same culture medium as described above before they were added to the cells to reach desired final compound concentrations and 1% DMSO concentration. Plates were then incubated at 37° C. for another 5 days before measurement of HBeAg level and cell viability. Extracellular HBeAg level were measured with enzyme-linked immunosorbent assay (ELISA) kit (Shanghai Kehua Diagnostic Medical Products Co., Ltd). Cell viability was assessed using Cell Counting Kit-8 (Donjindo, Cat. CK04-20). $IC_{50}$ values were derived from the dose-response curve using 4 parameter logistic curve fit method.

The compounds of the present invention were tested for their capacity to inhibit extracellular HBeAg level as described herein. The compounds of this invention were found to have $IC_{50}$ below 50 μM. Particular compounds of formula I were found to have $IC_{50}$ below 5.0 μM. Results of HepDES19 primary screen assay are given in Table 1.

TABLE 1

Activity data in HepDES19 primary screen assay

| Example No. | $IC_{50}$ (μM) |
|---|---|
| Swertianolin | >100 |
| 1 | 0.23 |
| 2 | 2.18 |
| 3 | 1.24 |
| 4 | 2.18 |
| 5 | 3.33 |
| 6 | 4.94 |
| 7 | 3.56 |
| 8 | 7.53 |
| 9 | 0.98 |
| 10 | 1.13 |
| 11 | 1.17 |
| 12 | 2.88 |
| 13 | 5.49 |
| 14 | 5.79 |
| 15 | 7.39 |
| 16 | 11.2 |
| 17 | 12.7 |
| 18 | 16.6 |
| 19 | 27.0 |
| 20 | 46.6 |
| 21 | 0.27 |
| 22 | 0.74 |
| 23 | 0.83 |
| 24 | 1.05 |
| 25 | 1.52 |
| 26 | 2.36 |
| 27 | 1.95 |
| 28 | 1.86 |
| 29 | 2.13 |
| 30 | 2.63 |
| 31 | 2.71 |
| 32 | 2.72 |
| 33 | 4.06 |
| 34 | 6.15 |
| 35 | 16.7 |
| 36 | 11.5 |
| 37 | 13.4 |
| 38 | 16.1 |
| 39 | 1.08 |
| 40 | 1.31 |
| 41 | 4.04 |
| 42 | 1.17 |
| 43 | 1.11 |
| 44 | 1.10 |
| 45 | 0.51 |
| 46 | 4.30 |
| 47 | 4.77 |
| 48 | 5.48 |
| 49 | 7.56 |
| 50 | 3.12 |
| 51 | 4.85 |
| 52 | 14.5 |
| 53 | 3.43 |
| 54 | 1.60 |
| 55 | 1.11 |
| 56 | 6.28 |
| 57 | 7.33 |
| 58 | 11.7 |
| 59 | 19.2 |
| 60 | 22.2 |
| 61 | 31.0 |
| 62 | 3.99 |
| 63 | 19.2 |
| 64 | 35.0 |
| 65 | 3.89 |
| 66 | 1.91 |
| 67 | 0.39 |
| 68 | 1.18 |
| 69 | 0.96 |
| 70 | 5.9 |
| 71 | 13 |
| 72 | 3.6 |
| 73 | 2.6 |
| 74 | 2.6 |
| 75 | 10.1 |

Example 77: cccDNA Southern Blot Assay

HepDES19 cells were seeded at $4 \times 10^6$ cells per T150 in the culture medium (Dulbecco's Modified Eagle Medium: Nutrient Mixture F-12 (DMEM:F12, Gibco Cat. 11320-82), 10% Fetal Bovine Serum (FBS, Clontech Cat. 631101), 0.1 mM Non-Essential Amino Acids Solution (NEAA, Gibco Cat. 11140-050), 50 g/mL Penicillin-Streptomycin (PS, Invitrogen Cat. 15140-163), 500 μg/mL Geneticin (G418, Invitrogen Cat. 10131-027) in the absence of Tet for 8 days. These cells were seeded at the density of $1 \times 10^6$ cells per well in 6-well plate. At 24 hrs after seeding, serial dilutions of compounds made with DMSO (Sigma, Cat. D2650) were further diluted with the same culture medium as described above before they were added to the cells to reach desired final compound concentrations and 1% DMSO concentration. After 5 days' compound treatment, the cells growing in one well from 6-well plate were re-suspended with 500 μL re-suspension buffer (50 mM tris[hydroxymethyl]aminomethane pH 7.5), 10 mM ethylenediaminetetraacetic acid (EDTA), 50 μg/mL RNase A (Qiagen, Cat. 158922). 500 μL of 1.2% sodium dodecyl sulfate (SDS) was then added into the re-suspended cells to lyse the cells. After 15 minutes' incubation, 700 μL precipitation buffer (3M cesium chloride, 1M potassium acetate, 0.67M acetic acid) was added and the lysate was incubated at 4° C. for 2 h. The lysate was centrifuged at 15000 revolutions per minute (RPM) at 4° C. for 15 minutes. The supernatant was collected and loaded onto Qiagen miniprep columns (QIAprep spin Mini prep kit, Cat. No. 27016). After centrifugation for 1 minute at 15000 RPM, the column was washed once with 750 L wash buffer PE from QIAprep spin Mini prep kit. 80 μL of double distilled water was loaded to the columns to elute Hirt DNA.

Hirt DNA of each sample was loaded into 1.2% 1x tris-acetate electrophoresis (TAE) agarose gel and separated at 90 voltages for 3 hours. The gel was then treated in 50 mM NaAc—HAc, pH4.2 for 30 min at room temperature (RT), and then denatured by soaking in denaturation buffer (0.5 M sodium hydroxide, 1.5 M sodium chloride) at RT for 30-45 min. The gel was then treated with neutralization buffer (1M tris[hydroxymethyl]aminomethane pH7.4 and 1.5M NaCl) at RT for 30 to 45 min.

The gel was transferred onto a pre-wet Nylon membrane (GE life science, Hybond N+) by capillary transfer method overnight, followed by UV crosslinking. The membrane was transferred into a hybridization tube, then rinsed with double distilled water at 60° C. for 5 mins. 10 mL of hybridization buffer (Lab kits, China) was added, the resulting sample was rotated in hybridization oven at 60° C. for 1 hour. Digoxigenin (DIG)-labelled HBV probe (SEQ ID NO: 1) was denatured at 95° C. for 10 minutes, and then 7 μL of denatured probe was added to the hybridization tube, which was rotated in hybridization oven at 60° C. overnight.

On the second day, the membrane was washed according to the procedure of DIG wash and block buffer set kit (Roche, Cat. 11 585 762 001), and then incubated with 50 mL antibody solution (Antibody anti-Digoxigenin-AP Fab fragment (Roche Cat. 11093274910) diluted in fresh 1× blocking buffer at 1:10,000) for 1 hour. The membrane was washed with 50 mL washing buffer (1× Maleic buffer with 0.3% Tween-20) for 15 minutes twice, and equilibrated with 20 mL detection buffer (0.1M tris[hydroxymethyl]aminomethane pH9.5, 0.1M sodium chloride) for 5 minutes. CDP-Star substrate (Roche, Cat. 12041677001) was added to the membrane for 5 minutes, and then the membrane was scanned by Bio-Rad Visualize Image System (Biorad, ChemiDoc-MP, Serial No. 731BR00916).

Results of cccDNA Southern Blot assay are given in FIGS. 1-6. The results indicate that the compounds of this invention dose-dependently reduced cccDNA level in HepDES19 cells.

Example 78: Cryopreserved Primary Human Hepatocytes (PHH) Assay

Cryopreserved PHH (BioreclamationIVT, Lot YJM) was thawed at 37° C. and gently transferred into pre-warmed InVitroGRO HT medium (BioreclamationIVT, Cat. S03317). The mixture was centrifuged at 70 relative centrifugal force (RCF) for 3 minutes at RT, and the supernatant was discarded. Pre-warmed InVitroGRO CP medium (BioreclamationIVT, Cat # S03316) was added to the cell pellet to gently re-suspend cells. The cells were seeded at the density of $5.8 \times 10^4$ cells per well to collagen I coated 96-well plate (Gibco, Cat. A1142803) with the InVitroGRO CP medium. All plates were incubated at 37° C. with 5% $CO_2$ and 85% humidity.

At 20 hours after plating, the medium was changed to PHH culture medium (Dulbecco's Modified Eagle Medium (DMEM)/F12 (1:1) (Gibco, Cat. 11320-033), 10% fetal bovine serum (Gibco Cat. 10099141), 100 U/mL penicillin, 100 μg/mL streptomycin (Gibco, Cat. 151401-122), 5 ng/mL human epidermal growth factor (Invitrogen Cat. PHG0311L), 20 ng/mL dexamethasone (Sigma, Cat. D4902) and 250 ng/mL human recombinant insulin (Gibco, Cat. 12585-014)). And the cells were incubated at 37° C. with 5% $CO_2$ and 85% humidity for 4 hours. The medium was then changed to pre-warmed PHH culture medium containing 4% polyethylene glycol (PEG) MW8000 (Sigma, Cat. P1458-50ML) and 1% DMSO (Sigma, Cat. D2650). $5.8 \times 10^6$ genomic equivalents of HBV were added into the medium.

At 24 hours post-infection, the cells were gently washed with PBS and refreshed with PHH culture medium supplemented with 1% DMSO, and 0.25 mg/mL Matrix gel (Corning, Cat. 356237) at 200 μL per well. All plates were immediately placed in at 37° C. $CO_2$ incubator.

24 hours later, serial dilutions of compounds made with DMSO were further diluted with the same culture medium (PHH culture medium supplemented with 1% DMSO and 0.25 mg/mL Matrix gel as described above) before they were added to the cells to reach desired final compound concentrations and 1% DMSO concentration. The medium containing the compounds were refreshed every three days.

At 9 days post-compound treatment, extracellular HBsAg level were measured with Chemiluminescence Immuno Assay (CLIA) kit (Autobio, HBsAg Quantitative CLIA). Extracellular HBV DNA was extracted by MagNA Pure 96 system (Roche) and then determined by quantitative PCR with the following primers and probe: HBV-Forward Primer (SEQ ID NO:2): AAGAAAAACCCCGCCTGTAA (5' to 3'); HBV-Reverse Primer (SEQ ID NO:3): CCTGTTCT-GACTACTGCCTCTCC(5' to 3'); HBV-Probe: 5'+tetramethylrhodamine+SEQ ID NO:4+black hole quencher 2-3', wherein SEQ ID NO:4 is CCTGATGTGATGTTCTCCAT-GTTCAGC.

HBsAg $IC_{50}$ and HBV DNA $IC_{50}$ values were derived from the dose-response curve using 4 parameter logistic curve fit method. Results of Cryopreserved PHH assay are given in Table 2 and Table 3.

TABLE 2

HBsAg $IC_{50}$ data in Cryopreserved PHH assay

| Example No. | HBsAg $IC_{50}$ (μM) |
|---|---|
| Swertianolin | >100 |
| 2 | 1.33 |
| 3 | 1.64 |
| 4 | 1.58 |
| 5 | 17.8 |
| 6 | 5.06 |
| 26 | 1.17 |
| 39 | 3.18 |
| 40 | 1.69 |
| 41 | 8.08 |
| 42 | 7.74 |
| 43 | 8.22 |
| 44 | 12.4 |
| 53 | 8.12 |
| 66 | 8.48 |
| 67 | 1.29 |

TABLE 3

HBV DNA $IC_{50}$ in Cryopreserved PHH assay

| Example No. | $IC_{50}$ (μM) |
|---|---|
| 2 | 2.30 |
| 3 | 1.61 |
| 4 | 1.93 |
| 5 | 9.62 |

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

The invention claimed is:
1. A compound of formula I,

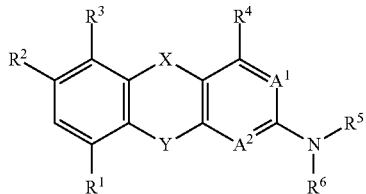

wherein:
$R^1$ is halogen or halo$C_{1-6}$alkyl;
$R^2$ is hydrogen or halogen;
$R^3$ is hydrogen, halogen, $C_{1-6}$alkyl, halo$_{1-6}$alkyl, cyano or hydroxy;
$R^4$ is hydrogen;
$R^5$ and $R^6$ together with nitrogen to which they are attached form pyrrolidinyl, oxopyrrolidinyl, azepanyl, diazepanyl, piperidinyl, hydroxypiperidinyl, carboxypiperidinyl, $C_{1-6}$alkylpiperazinyl, morpholinyl, 2,6-diazaspiro[3.4]octan-6-yl or 2,7-diazaspiro[4.4]nonan-2-yl, wherein pyrrolidinyl is unsubstituted or substituted with one, two or three substituents independently selected from: $C_{1-6}$alkyl, $C_{1-6}$alkoxy, hydroxy, carboxy, carboxy$C_{1-6}$alkyl, hydroxy$C_{1-6}$alky, amino, $C_{1-6}$alkoxycarbonyl, halophenyl, pyridinyl, (di$C_{1-6}$alkylamino)carbonyl and morpholinylcarbonyl;
X is —C(=O)— or —C($R^9$)($R^{10}$)—, wherein
$R^9$ and $R^{10}$ are independently selected from hydrogen, $C_{1-6}$alkyl, halo$C_{1-6}$alkyl, $C_{1-6}$alkoxy, hydroxy, oxetanyl and halophenyl-CH(—O-carbonyl $C_{1-6}$alkyl)-; or
$R^9$ and $R^{10}$ together with carbon to which they are attached form

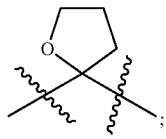 [SMILES: *C1(*)CCCO1]

$A^1$ is N or $CR^7$, wherein $R^7$ is hydrogen, halogen or $C_{1-6}$alkyl;
$A^2$ is N or $CR^8$, wherein $R^8$ is hydrogen or halogen; and
Y is O or S;
with the proviso that 1-[5-fluoro-9-(oxetan-3-yl)-9H-xanthen-3-yl]pyrrolidine is excluded;
or a pharmaceutically acceptable salt, enantiomer, or diastereomer thereof.

2. A compound according to claim 1, wherein:
$R^1$ is halogen or halo$C_{1-6}$alkyl;
$R^2$ is hydrogen or halogen;
$R^3$ is hydrogen, halogen, $C_{1-6}$alkyl, halo$C_{1-6}$alkyl, cyano or hydroxy;
$R^4$ is hydrogen;
$R^5$ and $R^6$ together with nitrogen to which they are attached form pyrrolidinyl, oxopyrrolidinyl, azepanyl, diazepanyl, piperidinyl, hydroxypiperidinyl, carboxypiperidinyl, $C_{1-6}$alkylpiperazinyl, morpholinyl, 2,6-diazaspiro[3.4]octan-6-yl or 2,7-diazaspiro[4.4]nonan-2-yl, wherein pyrrolidinyl is unsubstituted or substituted with one, two or three substituents independently selected from $C_{1-6}$alkyl, $C_{1-6}$alkoxy, hydroxy, carboxy, halo$C_{1-6}$alkyl, carboxy$C_{1-6}$alkyl, hydroxy $C_{1-6}$alky, amino, $C_{1-6}$alkoxycarbonyl, halophenyl, pyridinyl, (di$C_{1-6}$alkylamino)carbonyl and morpholinylcarbonyl;
X is —C(=O)—;
$A^1$ is N or $CR^7$, wherein $R^7$ is hydrogen, halogen or $C_{1-6}$alkyl;
$A^2$ is N or CH; and
Y is O;
or a pharmaceutically acceptable salt, enantiomer, or diastereomer thereof.

3. A compound according to claim 2, wherein:
$R^1$ is halogen or halo$C_{1-6}$alkyl;
$R^2$ is hydrogen or halogen;
$R^3$ is hydrogen, halogen, $C_{1-6}$alkyl, halo$C_{1-6}$alkyl, cyano or hydroxy;
$R^4$ is hydrogen;
$R^5$ and $R^6$ together with nitrogen to which they are attached form pyrrolidinyl unsubstituted or substituted with one, two or three substituents independently selected from: $C_{1-6}$alkyl, $C_{1-6}$alkoxy, hydroxy, carboxy, halo$C_{1-6}$alkyl, carboxy$C_{1-6}$alkyl, hydroxy$C_{1-6}$alky, amino, $C_{1-6}$alkoxycarbonyl, halophenyl, pyridinyl, (di$C_{1-6}$alkylamino)carbonyl and morpholinylcarbonyl;
X is —C(=O)—;
$A^1$ is N or $CR^7$, wherein $R^7$ is hydrogen, halogen or $C_{1-6}$alkyl;
$A^2$ is N or CH; and
Y is O;
or a pharmaceutically acceptable salt, enantiomer, or diastereomer thereof.

4. A compound according to claim 3, wherein:
$R^1$ is halogen or halo$C_{1-6}$alkyl;
$R^2$ is hydrogen or halogen;
$R^3$ is hydrogen, halogen, $C_{1-6}$alkyl, cyano or hydroxy;
$R^4$ is hydrogen;
$R^5$ and $R^6$ together with nitrogen to which they are attached form pyrrolidinyl, hydroxypyrrolidinyl, $C_{1-6}$alkoxypyrrolidinyl, carboxypyrrolidinyl or $C_{1-6}$alkoxycarbonylpyrrolidinyl;
X is —C(=O)—;
$A^1$ is $CR^7$, wherein $R^7$ is hydrogen, halogen or $C_{1-6}$alkyl;
$A^2$ is CH; and
Y is O;
or a pharmaceutically acceptable salt, or enantiomer, or diastereomer thereof.

5. A compound according to claim 4, wherein:
$R^1$ is fluoro, chloro, bromo or trifluoromethyl;
$R^2$ is hydrogen, fluoro or chloro;
$R^3$ is hydrogen, fluoro, chloro, methyl, trifluoromethyl, cyano or hydroxy;
$R^4$ is hydrogen;
$R^5$ and $R^6$ together with nitrogen to which they are attached form pyrrolidinyl, hydroxypyrrolidinyl, methoxyprrolidinyl, carboxypyrrolidinyl or methoxycarbonylpyrrolidinyl;
X is —C(=O)—;
$A^1$ is $CR^7$, wherein $R^7$ is hydrogen, fluoro, chloro or methyl;
$A^2$ is CH; and
Y is O;
or a pharmaceutically acceptable salt, enantiomer, or diastereomer thereof.

6. A compound according to claim 4, or a pharmaceutically acceptable salt, enantiomer, or diastereomer thereof, wherein $R^1$ is fluoro or chloro.

7. A compound according to claim 4, or a pharmaceutically acceptable salt, enantiomer, or diastereomer thereof, wherein, $R^2$ is hydrogen.

8. A compound according to claim 4, or pharmaceutically acceptable salt, enantiomer, or diastereomer thereof, wherein, $R^3$ is hydrogen, fluoro, chloro or trifluoromethyl.

9. A compound according to claim 4, or a pharmaceutically acceptable salt, enantiomer, or diastereomer thereof, wherein, $R^5$ and $R^6$ together with nitrogen to which they are attached form pyrrolidinyl or carboxypyrrolidinyl.

10. A compound according to claim 4, or a pharmaceutically acceptable salt, enantiomer, or diastereomer thereof, wherein, $A^1$ is CH.

11. A compound according to claim 4, wherein:
$R^1$ is halogen;
$R^2$ is hydrogen;
$R^3$ is hydrogen, halogen or haloC$_{1-6}$alkyl;
$R^4$ is hydrogen;
$R^5$ and $R^6$ together with nitrogen to which they are attached form pyrrolidinyl or carboxypyrrolidinyl;
X is-C(=O)—;
$A^1$ is CH;
$A^2$ is CH; and
Y is O;
or a pharmaceutically acceptable salt, enantiomer, or diastereomer thereof.

12. A compound according to claim 11, wherein:
$R^1$ is fluoro or chloro;
$R^2$ is hydrogen;
$R^3$ is hydrogen, fluoro, chloro or trifluoromethyl;
$R^4$ is hydrogen;
$R^5$ and $R^6$ together with nitrogen to which they are attached form pyrrolidinyl or carboxypyrrolidinyl;
X is-C(=O)—;
$A^1$ is CH;
$A^2$ is CH; and
Y is O;
or a pharmaceutically acceptable salt, enantiomer, or diastereomer thereof.

13. A compound according to claim 4, selected from:
5-chloro-3-pyrrolidin-1-yl-xanthen-9-one;
1-(5-chloro-9-oxo-xanthen-3-yl)pyrrolidine-3-carboxylic acid;
(3R)-1-(5-chloro-9-oxo-xanthen-3-yl)pyrrolidine-3-carboxylic acid;
(3S)-1-(5-chloro-9-oxo-xanthen-3-yl)pyrrolidine-3-carboxylic acid;
1-(5-fluoro-9-oxo-xanthen-3-yl)pyrrolidine-3-carboxylic acid;
1-(5-bromo-9-oxo-xanthen-3-yl)pyrrolidine-3-carboxylic acid;
methyl 1-(5-chloro-9-oxo-xanthen-3-yl)pyrrolidine-3-carboxylate;
5-fluoro-3-pyrrolidin-1-yl-xanthen-9-one;
1-chloro-4-fluoro-6-pyrrolidin-1-yl-xanthen-9-one;
5-fluoro-3-(3-hydroxypyrrolidin-1-yl)xanthen-9-one;
5-fluoro-2-methyl-3-pyrrolidin-1-yl-xanthen-9-one;
1-(5,8-dichloro-9-oxo-xanthen-3-yl)pyrrolidine-3-carboxylic acid;
5-chloro-3-[(3S)-3-hydroxypyrrolidin-1-yl]xanthen-9-one;
2,5-difluoro-3-pyrrolidin-1-yl-xanthen-9-one;
5-chloro-3-[(3R)-3-hydroxypyrrolidin-1-yl]xanthen-9-one;
5-fluoro-3-[(3S)-3-hydroxypyrrolidin-1-yl]xanthen-9-one;
5-fluoro-3-[(3R)-3-hydroxypyrrolidin-1-yl]xanthen-9-one;
5-fluoro-3-(3-methoxypyrrolidin-1-yl)xanthen-9-one;
2-chloro-4-fluoro-6-pyrrolidin-1-yl-xanthen-9-one;
1-(5-chloro-9-oxo-xanthen-3-yl)pyrrolidine-2-carboxylic acid;
1-[9-oxo-5-(trifluoromethyl)xanthen-3-yl]pyrrolidine-3-carboxylic acid;
1-(5-chloro-2-methyl-9-oxo-xanthen-3-yl)pyrrolidine-3-carboxylic acid;
1-(5-chloro-8-methyl-9-oxo-xanthen-3-yl)pyrrolidine-3-carboxylic acid;
1-(5-chloro-2-fluoro-9-oxo-xanthen-3-yl)pyrrolidine-3-carboxylic acid;
1-(2,5-dichloro-9-oxo-xanthen-3-yl)pyrrolidine-3-carboxylic acid;
1-(5-chloro-8-cyano-9-oxo-xanthen-3-yl)pyrrolidine-3-carboxylic acid;
1-(5-chloro-8-hydroxy-9-oxo-xanthen-3-yl)pyrrolidine-3-carboxylic acid;
1-(5-chloro-8-fluoro-9-oxo-xanthen-3-yl)pyrrolidine-3-carboxylic acid;
1-[5-chloro-9-oxo-8-(trifluoromethyl)xanthen-3-yl]pyrrolidine-3-carboxylic acid;
2-chloro-5-fluoro-3-pyrrolidin-1-yl-xanthen-9-one;
(3R)-1-(5,8-dichloro-9-oxo-xanthen-3-yl)pyrrolidine-3-carboxylic acid;
1-(5,7-dichloro-9-oxo-xanthen-3-yl)pyrrolidine-3-carboxylic acid;
1-(5-chloro-7-fluoro-9-oxo-xanthen-3-yl)pyrrolidine-3-carboxylic acid; and
(3R)-1-(5-chloro-2-methyl-9-oxo-xanthen-3-yl)pyrrolidine-3-carboxylic acid;
or a pharmaceutically acceptable salt, enantiomer, or diastereomer thereof.

14. A compound according to claim 4, selected from:
5-chloro-3-pyrrolidin-1-yl-xanthen-9-one;
1-(5-chloro-9-oxo-xanthen-3-yl)pyrrolidine-3-carboxylic acid;
(3R)-1-(5-chloro-9-oxo-xanthen-3-yl)pyrrolidine-3-carboxylic acid;
(3 S)-1-(5-chloro-9-oxo-xanthen-3-yl)pyrrolidine-3-carboxylic acid;
5-fluoro-3-pyrrolidin-1-yl-xanthen-9-one;
1-(5-chloro-8-fluoro-9-oxo-xanthen-3-yl)pyrrolidine-3-carboxylic acid;
1-[5-chloro-9-oxo-8-(trifluoromethyl)xanthen-3-yl]pyrrolidine-3-carboxylic acid;
1-(5,8-dichloro-9-oxo-xanthen-3-yl)pyrrolidine-3-carboxylic acid; and
(3R)-1-(5,8-dichloro-9-oxo-xanthen-3-yl)pyrrolidine-3-carboxylic acid;
or a pharmaceutically acceptable salt, enantiomer, or diastereomer thereof.

15. A compound according to claim 3, or a pharmaceutically acceptable salt, enantiomer, or diastereomer thereof, wherein $R^5$ and $R^6$ together with the nitrogen to which they are attached form aminopyrrolidinyl, carboxy(methyl)pyrrolidinyl, carboxy(dimethyl)pyrrolidinyl, carboxy(trifluoromethyl)pyrrolidinyl, carboxy(fluorophenyl)pyrrolidinyl, carboxy(chlorophenyl)pyrrolidinyl, carboxy(pyridinyl)pyrrolidinyl, carboxymethylpyrrolidinyl, dimethylaminocarbonylprrolidinyl, hydroxymethylpyrrolidinyl, morpholinylcarbonylpyrrolidinyl or pyridinylpyrrolidinyl.

16. A compound according to claim 15, selected from:
2-[1-(5-chloro-9-oxo-xanthen-3-yl)pyrrolidin-3-yl]acetic acid;

5-chloro-3-[3-(hydroxymethyl)pyrrolidin-1-yl]xanthen-9-one;
(3R,4S)-1-(5-chloro-9-oxo-xanthen-3-yl)-4-(4-fluorophenyl)pyrrolidine-3-carboxylic acid;
1-(5-chloro-9-oxo-xanthen-3-yl)-3-methyl-pyrrolidine-3-carboxylic acid;
1-(5-chloro-9-oxo-xanthen-3-yl)-4,4-dimethyl-pyrrolidine-3-carboxylic acid;
(3R,4S)-1-(5-chloro-9-oxo-xanthen-3-yl)-4-(3-pyridyl)pyrrolidine-3-carboxylic acid;
1-(5-chloro-9-oxo-xanthen-3-yl)-3-(trifluoromethyl)pyrrolidine-3-carboxylic acid;
(3S,4R)-1-(5-chloro-9-oxo-xanthen-3-yl)-4-(4-chlorophenyl)pyrrolidine-3-carboxylic acid;
5-fluoro-3-[3-(4-pyridyl)pyrrolidin-1-yl]xanthen-9-one;
1-(5-chloro-9-oxo-xanthen-3-yl)-N,N-dimethyl-pyrrolidine-3-carboxamide;
3-[(3S)-3-aminopyrrolidin-1-yl]-5-fluoro-xanthen-9-one;
3-[(3R)-3-aminopyrrolidin-1-yl]-5-fluoro-xanthen-9-one; and
5-chloro-3-[3-(morpholine-4-carbonyl)pyrrolidin-1-yl]xanthen-9-one;
or a pharmaceutically acceptable salt, enantiomer, or diastereomer thereof.

17. A compound according to claim 3, or a pharmaceutically acceptable salt, enantiomer, or diastereomer thereof, wherein one of $A^1$ and $A^2$ is N, and the other one is CH.

18. A compound according to claim 17, selected from:
1-(6-chloro-10-oxo-chromeno[3,2-c]pyridin-3-yl)pyrrolidine-3-carboxylic acid;
6-fluoro-3-pyrrolidin-1-yl-chromeno[3,2-c]pyridin-10-one;
9-chloro-2-pyrrolidin-1-yl-chromeno[2,3-b]pyridin-5-one; and
5-chloro-3-[3-(morpholine-4-carbonyl)pyrrolidin-1-yl]xanthen-9-one;
or a pharmaceutically acceptable salt, enantiomer, or diastereomer thereof.

19. A compound according to claim 2, or a pharmaceutically acceptable salt, enantiomer, or diastereomer thereof, wherein $R^5$ and $R^6$ together with the nitrogen to which they are attached form oxopyrrolidinyl, azepanyl, diazepanyl, piperidinyl, hydroxypiperidinyl, carboxypiperidinyl, $C_{1-6}$alkylpiperazinyl, morpholinyl, 2,6-diazaspiro[3.4]octan-6-yl or 2,7-diazaspiro[4.4]nonan-2-yl.

20. A compound according to claim 19, selected from:
5-fluoro-3-(1-piperidyl)xanthen-9-one;
5-chloro-3-(3-hydroxy-1-piperidyl)xanthen-9-one;
3-(azepan-1-yl)-5-fluoro-xanthen-9-one;
1-(5-chloro-9-oxo-xanthen-3-yl)piperidine-3-carboxylic acid;
1-(5-fluoro-9-oxo-xanthen-3-yl)pyrrolidin-2-one;
5-fluoro-3-morpholino-xanthen-9-one;
5-fluoro-3-(4-methylpiperazin-1-yl)xanthen-9-one;
3-(2,6-diazaspiro[3.4]octan-6-yl)-5-fluoro-xanthen-9-one;
3-(2,7-diazaspiro[4.4]nonan-2-yl)-5-fluoro-xanthen-9-one; and
3-(1,4-diazepan-1-yl)-5-fluoro-xanthen-9-one;
or a pharmaceutically acceptable salt, enantiomer, or diastereomer thereof.

21. A compound according to claim 1, wherein:
$R^1$ is halogen;
$R^2$, $R^3$ and $R^4$ are hydrogen;
$R^5$ and $R^6$ together with nitrogen to which they are attached form pyrrolidinyl or 3-carboxy-pyrrolidinyl;
X is —C($R^9$)($R^{10}$)—, wherein
$R^9$ and $R^{10}$ are independently selected from: hydrogen, $C_{1-6}$alkyl, halo$C_{1-6}$alkyl, $C_{1-6}$alkoxy, hydroxy, oxetanyl and halophenyl-CH(—O-carbonyl$C_{1-6}$alkyl)-; or
$R^9$ and $R^{10}$ together with carbon to which they are attached form

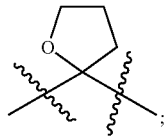 [SMILES: *C1(*)CCCO1]

$A^1$ is $CR^7$, wherein $R^7$ is hydrogen or halogen;
$A^2$ is $CR^8$, wherein $R^8$ is hydrogen or halogen; and
Y is O;
or a pharmaceutically acceptable salt, enantiomers, or diastereomer thereof.

22. A compound according to claim 21, wherein:
$R^1$ is fluoro or chloro;
$R^2$, $R^3$ and $R^4$ are hydrogen;
$R^5$ and $R^6$ together with nitrogen to which they are attached form pyrrolidinyl or 3-carboxy-pyrrolidinyl;
X is —C($R^9$)($R^{10}$)—, wherein
$R^9$ and $R^{10}$ are independently selected from: hydrogen, methyl, trifluoromethyl, methoxy, hydroxy, oxetanyl and fluorochlorophenyl-CH(—O-carbonylmethyl)-; or
$R^9$ and $R^{10}$ together with carbon to which they are attached form

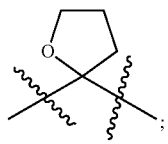 [SMILES: *C1(*)CCCO1]

$A^1$ is $CR^7$, wherein $R^7$ is hydrogen or chloro;
$A^2$ is $CR^8$, wherein $R^8$ is hydrogen or chloro; and
Y is O;
or a pharmaceutically acceptable salt, enantiomers or diastereomer thereof.

23. A compound according to claim 21, selected from:
1-(5'-fluorospiro[tetrahydrofuran-2,9'-xanthene]-3'-yl)pyrrolidine;
1-(5-chloro-9-methyl-9H-xanthen-3-yl)pyrrolidine;
1-(5-chloro-9H-xanthen-3-yl)pyrrolidine;
1-(2,4,5-trichloro-9H-xanthen-3-yl)pyrrolidine;
1-[5-chloro-9-(oxetan-3-yl)-9H-xanthen-3-yl]pyrrolidine;
[(2-chloro-3-fluoro-phenyl)-(5-chloro-3-pyrrolidin-1-yl-9H-xanthen-9-yl)methyl]acetate;
5-chloro-3-pyrrolidin-1-yl-9-(trifluoromethyl)xanthen-9-ol;
1-[5-chloro-9-m ethoxy-9-(trifluoromethyl)xanthen-3-yl]pyrrolidine;
1-[5-chloro-9-(trifluoromethyl)-9H-xanthen-3-yl]pyrrolidine;
1-(5-fluoro-9H-xanthen-3-yl)pyrrolidine; and
1-(5-chloro-9-methyl-9H-xanthen-3-yl)pyrrolidine-3-carboxylic acid;
or a pharmaceutically acceptable salt, enantiomer, or diastereomer thereof.

24. A compound according to claim 1, selected from:
1-(5-chloro-9-oxo-thioxanthen-3-yl)pyrrolidine-3-carboxylic acid;
(3S)-1-(5-chloro-9-oxo-thioxanthen-3-yl)pyrrolidine-3-carboxylic acid; and
(3R)-1-(5-chloro-9-oxo-thioxanthen-3-yl)pyrrolidine-3-carboxylic acid;
or a pharmaceutically acceptable salt, enantiomer, or diastereomer thereof.

25. A process for preparing a compound according to claim 2, or a pharmaceutically acceptable salt, enantiomer, or diastereomer thereof, the process comprising:
(a) coupling a compound of formula (A)

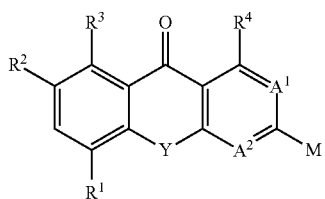

with a compound of formula (B)

in the presence of a catalyst, a ligand and a base; wherein M is F, Cl, Br or I.

26. A pharmaceutical composition comprising a compound according to claim 1, or a pharmaceutically acceptable salt, enantiomer, or diastereomer thereof, and a therapeutically inert carrier.

27. A method for the treatment of HBV infection, which method comprises administering to a patient in need thereof an effective amount of a compound according to according to claim 1, or a pharmaceutically acceptable salt, enantiomer, or diastereomer thereof.

28. A method for the inhibition of cccDNA, which method comprises administering to a patient in need thereof an effective amount of a compound according to claim 1, or a pharmaceutically acceptable salt, enantiomer, or diastereomer thereof.

29. A method for the inhibition of HBeAg, which method comprises administering to a patient in need thereof an effective amount of a compound according to claim 1, or a pharmaceutically acceptable salt, enantiomer, or diastereomer thereof.

30. A method for the inhibition of HBsAg, which method comprises administering to a patient in need thereof an effective amount of a compound according to claim 1, or a pharmaceutically acceptable salt, enantiomer, or diastereomer thereof.

31. A method for the inhibition of HBV DNA which method comprises administering to a patient in need thereof an effective amount of a compound according to claim 1, or a pharmaceutically acceptable salt, enantiomer, or diastereomer thereof.

* * * * *